US011160515B2

(12) United States Patent
Yoshimura et al.

(10) Patent No.: US 11,160,515 B2
(45) Date of Patent: Nov. 2, 2021

(54) X-RAY CT SCANNER, X-RAY IMAGE PROCESSOR, AND X-RAY IMAGE DISPLAY

(71) Applicant: J. MORITA MFG. CORP., Kyoto (JP)

(72) Inventors: Takahiro Yoshimura, Kyoto (JP); Tomoyuki Sadakane, Kyoto (JP)

(73) Assignee: J. Morita Mfg. Corp., Kyoto (JP)

(*) Notice: Subject to any disclaimer, the term of this patent is extended or adjusted under 35 U.S.C. 154(b) by 44 days.

(21) Appl. No.: 16/573,346

(22) Filed: Sep. 17, 2019

(65) Prior Publication Data

US 2020/0008761 A1 Jan. 9, 2020

Related U.S. Application Data

(63) Continuation of application No. PCT/JP2018/010631, filed on Mar. 16, 2018.

(30) Foreign Application Priority Data

Mar. 17, 2017 (JP) ................................ 2017-053743

(51) Int. Cl.
*A61B 6/00* (2006.01)
*A61B 6/03* (2006.01)
(Continued)

(52) U.S. Cl.
CPC ................ *A61B 6/035* (2013.01); *A61B 6/04* (2013.01); *A61B 6/4435* (2013.01); *A61B 6/54* (2013.01); *A61B 6/587* (2013.01); *G03B 42/026* (2013.01)

(58) Field of Classification Search
CPC ....... A61B 6/032; A61B 6/4441; A61B 6/587; A61B 6/035; A61B 6/14; A61B 6/025;
(Continued)

(56) References Cited

U.S. PATENT DOCUMENTS 4,304,999 A 12/1981 Richey et al.
5,016,264 A * 5/1991 Hyttinen ................. A61B 6/14 378/177

(Continued)

FOREIGN PATENT DOCUMENTS

EP 2210559 A1 7/2010
JP 2-261434 A 10/1990

(Continued)

OTHER PUBLICATIONS

Timo Kiljunen et al., "Dental cone beam CT: A review", Physica Medica, Acta Medica Edizioni E Congressi, Rome, IT, vol. 31, No. 8, Oct. 23, 2015, pp. 844-860.

(Continued)

*Primary Examiner* — Irakli Kiknadze
(74) *Attorney, Agent, or Firm* — Capitol City TechLaw, PLLC; Samuel P. Burkholder

(57) ABSTRACT

An X-ray CT scanner generates CT imaging information on an imaging region, and has a revolution arm positioning an X-ray generator and an X-ray detector to face one another with a subject therebetween, directing the revolution arm to move so X-ray beam radiation is offset from the center of the imaging region. An axial direction changing mechanism changes an imaging target from a first imaging region to a second imaging region in an axial direction of the imaging central axis, and a controller controls offset CT imaging, and an X-ray imaging information generator to generate first and second CT imaging information based on projection data of the first and second imaging region and to generate a stitch imaging information comprising the first and second CT imaging information.

18 Claims, 33 Drawing Sheets

(51) Int. Cl.
*A61B 6/04* (2006.01)
*G03B 42/02* (2021.01)

(58) Field of Classification Search
CPC ....... A61B 6/04; A61B 6/4085; A61B 6/4417; A61B 6/4435; A61B 6/463; A61B 6/5205; A61B 6/5241; A61B 6/54; A61B 6/547; A61B 6/00; A61B 6/03; A61B 6/0487; A61B 6/4452; A61B 6/541; A61B 6/488; A61B 6/06; A61B 6/12; A61B 6/4405; A61B 6/486; A61B 2576/00; A61B 6/0407; A61B 6/465; G01N 2223/419; G01N 23/046; G01N 2223/505; G01N 2223/108; G01N 23/2255; G01N 2223/612; G01T 1/2018; G01T 1/22; G01T 1/24; G01T 1/2985; G06T 11/005; G06T 2211/412; G06T 11/008; G06T 2207/10081; G06T 2210/41; G06T 2211/404; G06T 2211/424; G06T 2211/428; G06T 2207/20212; G06T 2207/30004; G06T 11/60; G06T 15/08; G06T 2207/10124; G06T 2207/20221; G06T 3/20; G06T 3/4053; G06T 7/0016; G06T 7/33; A61N 2005/1061; A61N 5/1049; A61N 5/1067; A61N 2005/1085; A61N 2005/1091; A61N 2005/1095; A61N 5/1042; A61N 5/107; A61N 5/1071; A61N 5/1081; A61N 5/1082; A61N 2005/1055; A61N 5/1037; A61N 5/1045; G16H 30/20; G16H 30/40; G16H 40/60; G16H 50/50; G21K 1/02; G21K 1/025; H01J 2235/062; H01J 2235/068; H01J 2235/086; H01J 35/04; H01J 35/045; H01J 35/065; H01J 35/10; H01J 35/13; H01J 35/14; H01J 35/147; H01J 35/153; H01J 35/24; H05G 1/70; H05G 1/58; H05G 1/60; G03B 42/026; A61C 9/0053; G01V 5/0041; G01V 5/005; G01R 33/4808; G01R 33/4824; G01R 33/4833; G01R 33/5608; G01R 33/56308; G01R 33/56325; G01R 33/56509; G01R 33/567; H04N 7/18
USPC ........................................................ 378/4–19
See application file for complete search history.

(56) References Cited

U.S. PATENT DOCUMENTS

| | | | | |
|---|---|---|---|---|
| 11,051,774 | B2 * | 7/2021 | Bothorel | A61B 6/035 |
| 2010/0246755 | A1 * | 9/2010 | Suzuki | A61B 6/4441 378/11 |
| 2012/0039435 | A1 * | 2/2012 | Arai | A61B 6/542 378/11 |
| 2012/0176406 | A1 * | 7/2012 | Elenbaas | A61B 6/5241 345/629 |
| 2012/0189096 | A1 * | 7/2012 | Erhardt | A61B 6/032 378/22 |
| 2013/0136226 | A1 * | 5/2013 | Tomoe | A61B 6/14 378/4 |
| 2014/0126687 | A1 * | 5/2014 | Yoshikawa | A61B 6/4476 378/16 |
| 2015/0213633 | A1 | 7/2015 | Change et al. | |

FOREIGN PATENT DOCUMENTS

| | | | |
|---|---|---|---|
| JP | 3378401 | B2 | 2/2003 |
| JP | 2006-175278 | A | 7/2006 |
| JP | 2006314774 | A | 11/2006 |
| JP | 2008-167804 | A | 7/2008 |
| JP | 2009033392 | A | 2/2009 |
| JP | 2010214091 | A | 9/2010 |
| JP | 2010240387 | A | 10/2010 |
| JP | 2011-025012 | A | 2/2011 |
| JP | 2011-217947 | A | 11/2011 |
| JP | 2013-505802 | A | 2/2013 |
| JP | 2014-094091 | A | 5/2014 |
| JP | 2014180538 | A | 9/2014 |
| WO | 2009063974 | A1 | 5/2009 |
| WO | 2011039672 | A1 | 4/2011 |
| WO | 2016142818 | A1 | 9/2016 |

OTHER PUBLICATIONS

Office Action conducted by Japan Patent Office for Japan Patent Application 2020-054570 drafted Mar. 3, 2021. Japanese 4 pages, English 4 pages).

* cited by examiner

X-RAY CT SCANNER, X-RAY IMAGE PROCESSOR, AND X-RAY IMAGE DISPLAY

This application is a continuation application of International Application No. PCT/JP2018/010631 filed Mar. 16, 2018, the entire content of which is incorporated herein by reference.

This application claims priority under 35 USC § 119 (a)-(d) to JP Patent Application No. 2017-053743 filed Mar. 17, 2017, the entire content of which is incorporated herein by reference.

TECHNICAL FIELD

The present invention relates to an X-ray CT scanner generating, for example, X-ray imaging information on an imaging region of a subject processed by X-ray CT imaging, and an X-ray image processor.

BACKGROUND ART

Conventionally, in the field of medicine and the like, X-ray CT imaging is performed, by which an X-ray beam is directed toward a subject to collect projection data, and the acquired projection data is reconstructed on a computer to generate a computerized tomography image (computerized tomographic image, volume rendering image, etc.).

Such X-ray imaging s performed as follows. A subject is located between an X-ray generator and an X-ray detector. In this state, the X-ray generator and the X-ray detector are revolved around the subject while a cone-like X-ray beam (X-ray cone beam) is directed from the X-ray generator toward the subject. The detection results (projection data) detected by the X-ray detector collected, and X-ray imaging information is generated from the collected detected results (projection data) to reconstruct three-dimensional image data. A device performing such X-ray CT imaging is disclosed in, for example, Patent Document 1.

The X-ray CT scanner described in Patent Document 1 is capable of performing offset X-ray CT imaging, by which the position to which the X-ray cone beam is directed is offset from the center of the imaging region of the subject, so that part of the imaging region is always irradiated with the X-ray cone beam. With such offset X-ray CT imaging, X-ray CT imaging can be performed on a larger area with a smaller X-ray detection surface. Therefore, X-ray imaging information on a large area can be generated.

However, with the X-ray CT scanner in Patent Document 1, the X-ray detection surface is configured to be small in a revolution axis direction, in which the X-ray generator and the X-ray detector revolve. Therefore, in the revolution axis direction, the imaging region of the subject does not fall within the range of the X-ray cone beam. For this reason, there is an undesirable possibility that X-ray imaging information on a desired imaging region may not be acquired.

CITATION LIST

Patent Literature

Patent Document 1: Japanese Patent. No. 3378401

SUMMARY OF INTENTION

Technical Problem

Thus, the present invention has an object of providing an X-ray CT scanner capable of generating, with certainty, X-ray imaging information on a large imaging region in a revolution axis direction even with an X-ray detector configured to have a small X-ray detection surface, and an X-ray image processor.

Solution to Problem

The present invention is directed to an X-ray CT scanner performing X-ray CT imaging of an imaging region in a subject to generate an X-ray imaging information of said imaging region by detecting an X-ray cone beam irradiated from an X-ray generator with an X-ray detector. The X-ray CT scanner includes a supporter locating the X-ray generator and the X-ray detector such that the X-ray generator and the X-ray detector face each other while having she subject therebetween; an offset mechanism relatively moving an irradiation direction of the X-ray cone beam irradiated from the X-ray generator, with respect to a center of the imaging region such that the irradiation direction is offset from the center of the imaging region in a reference plane vertical to an imaging central axis of the imaging region; an axial direction changing mechanism changing as the imaging region from a first imaging region to which the X-ray CT imaging is executed first by the X-ray generator and the X-ray detector to a second imaging region to which the X-ray CT imaging is executed after the first imaging region in an axial direction of the imaging central axis, said imaging region comprising the first imaging region and the second imaging region; an imaging controller controlling the X-ray CT imaging to revolve the supporter with respect to the subject no generate the X-ray imaging information; and an image information generator generating stitch image information acquired as a result of joining first X-ray imaging information on the first imaging region and second X-ray imaging information on the second imaging region in the axial direction, the first X-ray imaging information and the second X-ray imaging information partially overlapping each other in the axial direction.

The X-ray CT scanner is configured to be capable of executing: control on offset CT imaging of controlling the offset mechanism such that the X-ray cone beam is always directed toward a part of the imaging region throughout the imaging, and control on the axial direction changing mechanism to generate the first X-ray imaging information and the second X-ray imaging information partially overlapping each other in the axial direction. At least one of the first. X-ray imaging information and the second X-ray imaging information being offset CT imaging information acquired by the offset CT imaging.

The present invention is also directed to an X-ray image processor generating X-ray imaging information on an imaging region of a subject to which X-ray CT imaging is executed. The X-ray image processor includes an image information generator generating stitch image information by joining first X-ray imaging information on a first imaging region to which the X-ray CT imaging is executed first and second X-ray imaging information on a second imaging region to which the X-ray CT imaging is executed after the first imaging region, the first imaging region and the second imaging region being partially overlapping each other along an axial direction of an imaging central axis of the imaging region. At least one of the first X-ray imaging information and the second X-ray imaging information, based on which the stitch imaging information is generated, being offset CT imaging information on the imaging region to which the offset CT imaging is executed.

The imaging central axis passes an imaging center of a CT imaging region processed by the X-ray CT imaging performed by revolving, in a direction crossing a revolution direction, the supporter that supports the X-ray generator and the X-ray detector. For example, the imaging central axis may match a mechanical revolution shaft that revolves while supporting the revolution of the supporter; may, in the case where the supporter is annular, match the center of the annular body, may be a central axis of a revolution axis moving track that is formed by movement of a revolution shaft moving mechanism, that horizontally moves the mechanical revolution shaft of the supporter in a plane crossing the revolution shaft, and the revolution of the mechanical revolution shaft of the support, in association with each other; or may be a central axis of an imaging region that is formed by relative movement of the subject with respect to the supporter while the revolution shaft merely revolves but does not move.

The first imaging region and the second imaging region refer to two regions acquired by dividing the imaging region along the imaging central axis. Namely, the first imaging region and the second imaging region may refer to two regions acquired by dividing the imaging region into two, or two selected regions acquired by dividing the imaging region into a plurality of regions.

The first imaging region and the second imaging region may be regions processed by the X-ray CT imaging continuously, or may be two regions processed by the imaging non-continuously.

The "moving the irradiation direction with respect to the center of the imaging region" described above may refer to, for example, a case where the supporter is revolved while the position of the revolution shaft of the supporter is moved with respect to the center of the imaging region; a case ere the irradiation direction of the X-ray cone beam irradiated from the X-ray generator in the state where the supporter and the subject are secured; a case where the irradiation direction of the X-ray cone beam irradiated from the X-ray generator is changed while at least one of the supporter and the subject is moved; a case where the secured supporter is revolved while the subject is moved by a moving mechanism; a case where both of the supporter and the subject are moved; and the like.

The "X-ray CT imaging generating the X-ray imaging information by revolving the supporter with respect to the subject" described above is a concept encompassing the entirety of a series of processes in the X-ray CT imaging; and may specifically encompass an instant in an imaging process of detecting, by the X-ray detector, the X-ray cone beam irradiated from the X-ray generator, and also a time period in which the supporter is revolved while the imaging process is stopped.

The axial direction changing mechanism may encompass, for example, a mechanism that moves, in the axial direction, the supporter supporting the X-ray generator and the X-ray detector; a mechanism that moves the X-ray generator and the X-ray detector in the axial direction; a mechanism that includes a collimator changing the irradiation direction or the irradiation position of the X-ray cone beam irradiated from the X-ray generator; a mechanism that moves the subject in the axial direction; a combination thereof; and the like.

The "first X-ray imaging information and the second X-ray imaging information partially overlapping in the axial direction" described above refers to a case where the first X-ray imaging information and the second X-ray imaging information, which are generated by the X-ray CT imaging performed while the supporter is revolved and are generally cylindrical have the same radius as each other, and a case where the first X-ray imaging information and the second X-ray imaging information have different radii from each other.

With the above-described invention, X-ray imaging information on a large imaging region may be generated with certainty even with an X-ray detector configured to have a small X-ray detection surface.

This will be described in more detail. The imaging region may be processed by the offset CT imaging under the control on the rotation center moving mechanism by the imaging controller. Therefore, an imaging region that is long in a width direction crossing the axial direction may be processed by X-ray CT imaging even with the X-ray detector configured to have a small X-ray detection surface. Therefore, offset X-ray imaging information including information on the region that is long in the width direction may be generated.

In addition, the imaging controller controls the axial direction changing mechanism and includes an image information generator. Therefore, the imaging region may be changed in the axial direction such that the first X-ray imaging information and the second X-ray imaging information partially overlapping each other may be generated during the X-ray CT imaging. Moreover, stitch image information may be generated by joining the first X-ray imaging information and the second X-ray imaging information generated by the X-ray CT imaging.

As described above, in the direction crossing the axial direction, the offset X-ray CT imaging information including information on a large region may be generated. In the axial direction, pieces of X-ray imaging information acquired by the imaging performed with the X-ray imaging region being divided into a plurality of regions may be joined with each other. Therefore, X-ray CT imaging information on the entirety of the large imaging region may be generated with certainty even with the X-ray detector configured to have a small X-ray detection surface. Thus, for example, the X-ray CT scanner may be made lightweight, and the cost may be decreased.

In an embodiment of the present invention, the offset mechanism may include a rotation center moving mechanism moving a revolution center of the supporter in a circular track about a central axis of the imaging region in the reference plane.

According to the present invention, the offset X-ray imaging information may be generated without moving or rotating the subject. Therefore, the load on the subject may be alleviated. The subject may be secured without being moved. Therefore, the subject may be prevented from unintentionally moving by, for example, the vibration at the start of the movement or at the finish of the imaging. For these reasons, accurate offset CT imaging may be performed, and the offset X-ray imaging information and the X-ray imaging information may be joined with each other with more certainty.

In an embodiment of the present invention, the axial direction changing mechanism may be configured to move at least one of the supporter and the subject in a revolution center direction along a revolution axis center of the supporter with respect to the other of the supporter and the subject.

According to the present invention, the target of irradiation may be changed from the first X-ray imaging region to the second X-ray imaging region in the axial direction with a simple structure. Therefore, the X-ray CT scanner does not need to have a complicated structure, and the productivity may be improved.

A range of the imaging region in which a plurality of pieces of CT imaging information overlap each other in the axial direction may be found by an amount of movement, in the axial direction, of at least one of the supporter and the subject with respect to the other of the supporter and the subject. Therefore, the amount of movement in the axial direction in a process of joining the plurality of pieces of X-ray imaging information may be used as a parameter value. For this reason, the computation load may be alleviated, and the stitch image information may be generated at a higher speed.

In an embodiment of the present invention, the axial direction changing mechanism may change the position of the supporter in a direction away from the subject after the X-ray CT imaging of the first imaging region is performed.

According to the present invention, during the change to the second imaging region after the imaging of the first imaging region under the control of the axial direction changing mechanism, the position of the supporter may be changed in the direction away from the subject. Therefore, the supporter may be prevented from approaching and interfering with the subject and thus the X-ray CT imaging may be performed safely. The supporter does not approach the subject too closely, and therefore, may be prevented from imposing any oppressive feeling on the subject.

In an embodiment of the present invention, the axial direction changing mechanism may include an axial direction irradiation angle adjusting mechanism changing the irradiation direct on of the X-ray cone beam in the axial direction with respect to the supporter.

According to the present invention, the target of irradiation may be changed from the first imaging region to the second imaging region by moving the irradiation direction of the X-ray cone beam irradiated from the X-ray generator, without moving the supporter supporting the X-ray generator and the X-ray detector. Therefore, the CT imaging may be performed without imposing any oppressive feeling on a patient, who is the subject.

In an embodiment of the present invention, the imaging controller may include an adjustment controller adjusting an overlapping amount of the first imaging region and the second imaging region.

According to the present invention, the overlapping amount adjusted between the first imaging information and the second imaging information may be prepared in advance. Therefore, the precision of the stitch image information generated by joining the first imaging information and the second imaging information may be improved.

In an embodiment of the present invention, an imaging mode in which the center of the imaging region matches a revolution center of the supporter during revolution and the X-ray cone beam always passing the entirety of the imaging region on the reference plane throughout the imaging may be set as a normal imaging mode. An imaging mode in which the offset CT imaging is performed may be set as an offset imaging mode. An imaging mode in at least one offset CT imaging information and an X-ray imaging information of an imaging region that is different from the imaging region to which the X-ray CT imaging is executed for said offset CT imaging information are combined and integrated may be set as an offset stitch imaging mode. The X-ray CT scanner may include an imaging mode selector selecting any one of these imaging modes.

The offset imaging mode refers to an imaging mode in which the offset. CT imaging is performed, according to which the X-ray cone beam always passes a part of the imaging region on the reference plane throughout the imaging.

The imaging mode selector may be, for example, an imaging mode in which offset imaging information and offset imaging information are combined and integrated, or may include an imaging mode selector that selects an imaging mode in which the offset imaging information and normal imaging information are combined and integrated.

Alternatively, the positions, the radii and the heights of the imaging regions to be processed by the offset imaging may be set and selected.

According to the present invention, the imaging mode suitable to the size of the imaging region may be appropriately selected. Therefore, the X-ray CT imaging of the imaging region may be performed appropriately. Thus, the amount of the X-ray to which the subject is exposed may be suppressed.

In an embodiment of the present invention, the X-ray CT scanner may include a display displaying a stitch image based on the stitch image information generated by the image information generator.

According to the present invention, the stick image corresponding to the imaging region may be displayed, and a CT image of the imaging region may be observed with a human eye.

In an embodiment of the present invention, the X-ray CT scanner may include a determiner determining whether the X-ray CT imaging of the imaging region changed in the axial direction under the control of the axial direction changing mechanism is possible or not; and a notifier performing notification based on determination results of the determiner.

According to the present invention, the determination results of the determiner may be notified by the notifier. Therefore, the X-ray CT imaging may be performed more safely.

The "determining whether the X-ray CT imaging is possible or not" described above may refer to a case where it is determined whether the X-ray CT imaging is physically possible or not because there may be a case where the supporter and the subject possibly physically contact each other; a case where the imaging region possibly includes a high sensitivity portion that is highly sensitive to the X-ray; a case where it is determined whether the X-ray CT imaging is possible or not because, for example, the high sensitivity site is included in an overlapping portion of the pieces of the X-ray imaging information; and the like.

In an embodiment of the present invention, the image controller may execute continuously first imaging control of controlling the X-ray CT imaging of the first imaging region and second imaging control of controlling the X-ray CT imaging of the second imaging region.

According to the present invention, the plurality of pieces of X-ray imaging information may be generated by a series of processes. Therefore, it is not needed to perform position alignment or the like before the imaging each time the plurality of pieces of X-ray imaging information are generated. Thus, the degree of alignment among the plurality of pieces of X-ray imaging information may be improved.

In an embodiment of the present invention, the X-ray CT scanner may include an X-ray restrictor forming the X-ray cone beam directed toward the imaging region; an imaging mechanism driver revolving the supporter around the subject; and a panorama imaging controller controlling at least the X-ray restrictor and the imaging mechanism driver. A direction perpendicular to the axial direction may be set as a lateral direction. The X-ray restrictor may include a lateral direction X-ray blocker blocking an irradiation range in the lateral direction of the X-ray cone beam to the imaging region such that the X-ray cone beam is allowed to be changed to an X-ray thin beam. The panorama imaging controller may be configured to direct the X-ray thin beam formed by changing a restriction range restricted by the X-ray restrictor, to revolve the supporter, thus to control the imaging mechanism driver such that the directed X-ray thin beam forms a panorama X-ray imaging track locus, and to perform a panorama imaging with the X-ray thin beam.

According to the present invention, the X-ray CT imaging and also the panorama imaging may be performed. Therefore, the X-ray imaging suitable to the purpose of treatment may be performed.

In an embodiment of the present invention, the first X-ray aging information and the second ray imaging information, based on which the stitch imaging information is generated, may each consist of the offset CT imaging information, and a distance of offset from a center of the imaging region in a reference plane vertical to the imaging central axis in each of said first and second X-ray imaging information may be different from other.

According to the present invention, stitch image information in which pieces of offset. X-ray imaging information having different radii are joined with each other may be generated.

In an embodiment of the present invention, one of the first X-ray imaging information or the second X-ray imaging information, based on which the stitch imaging information Is generated, may consist of X-ray imaging information on an imaging region having a radius, on a reference plane, different from that of an imaging region of other X-ray imaging information.

According to the present invention, the pieces of the X-ray imaging information acquired by the X-ray CT imaging performed in accordance with the imaging regions may be generated as the stitch image information.

This will be described in more detail. Stitch image information in which offset X-ray imaging information acquired by the imaging performed on a large imaging region and cylindrical X-ray imaging information having a different radius from that of the offset X-ray imaging information are joined with each other may be generated.

In the case where, for example, the imaging region represented by the X-ray imaging information other than the offset X-ray imaging information includes a high sensitivity site, the normal X-ray imaging may be performed on only a predetermined range avoiding the high sensitivity site. The X-ray imaging information generated in this manner and the offset X-ray imaging information may be joined with each other to generate the stitch image information. In this manner, stitch image information in accordance with the X-ray CT imaging performed in accordance with the imaging region of the subject may be generated.

In an embodiment of the present invention, an overlapping portion, in the stitch image information, of the first X-ray imaging information and the second X-ray imaging information joined with each other may be averaged.

The averaging process may refer to, for example, a case where the X-ray imaging information is weighted in accordance with the position, in the axial direction, in the X-ray imaging information acquired the joining performed in the axial direction; and a case where the averaging is simply performed with no consideration of the position of the overlapping position.

According to the present invention, the overlapping portion of two joined pieces of CT imaging information may be averaged. Therefore, stitch image information in which the overlapping portion of the X-ray imaging information is adjusted may be generated.

The X-ray imaging information is weighted and thus averaged in accordance with the position, in the axial direction, of the two joined pieces of the CT image information. Thus, stitch image information that does not clearly show the border between the different pieces of the CT image information overlapping each other may be generated.

In an embodiment of the present invention, the X-ray image processor may include an X-ray image generator generating, based on the first X-ray imaging information and the second X-ray imaging information, an X-ray-captured image of each of the imaging regions.

According to the present invention, the stitch image based on the stitch image information, and the X-ray image in accordance with the region of each of the first X-ray imaging information and the second X-ray imaging information, may be displayed separately. Therefore, it is not needed to construct any individual X-ray image from the stitch image information, and the data capacity may be decreased. In addition, for example, the X-ray image may be observed in the state where the pieces of the information do not overlap each other.

In an embodiment of the present invention, the X-ray image display may include a designation operation interface designating a desired position on three dimensional axes perpendicular to each other on the image display; and a sectional image information processor generating sectional image information corresponding the position designated by the designation operation interface.

According to the present invention, a desired cross-sectional view may be displayed. Therefore, an internal structure of a tooth, for example, the shape of a root canal as a target of the treatment, may be grasped.

Advantageous Effects of Invention

The present invention provides an X-ray CT scanner capable of generating, with certainty, X-ray imaging information on a large imaging region, and an X-ray image processor.

DESCRIPTION OF EMBODIMENTS

Hereinafter, an X-ray CT scanner 1 according to the present invention will be described with reference to FIG. 1 through FIG. 9.

Figure 1:
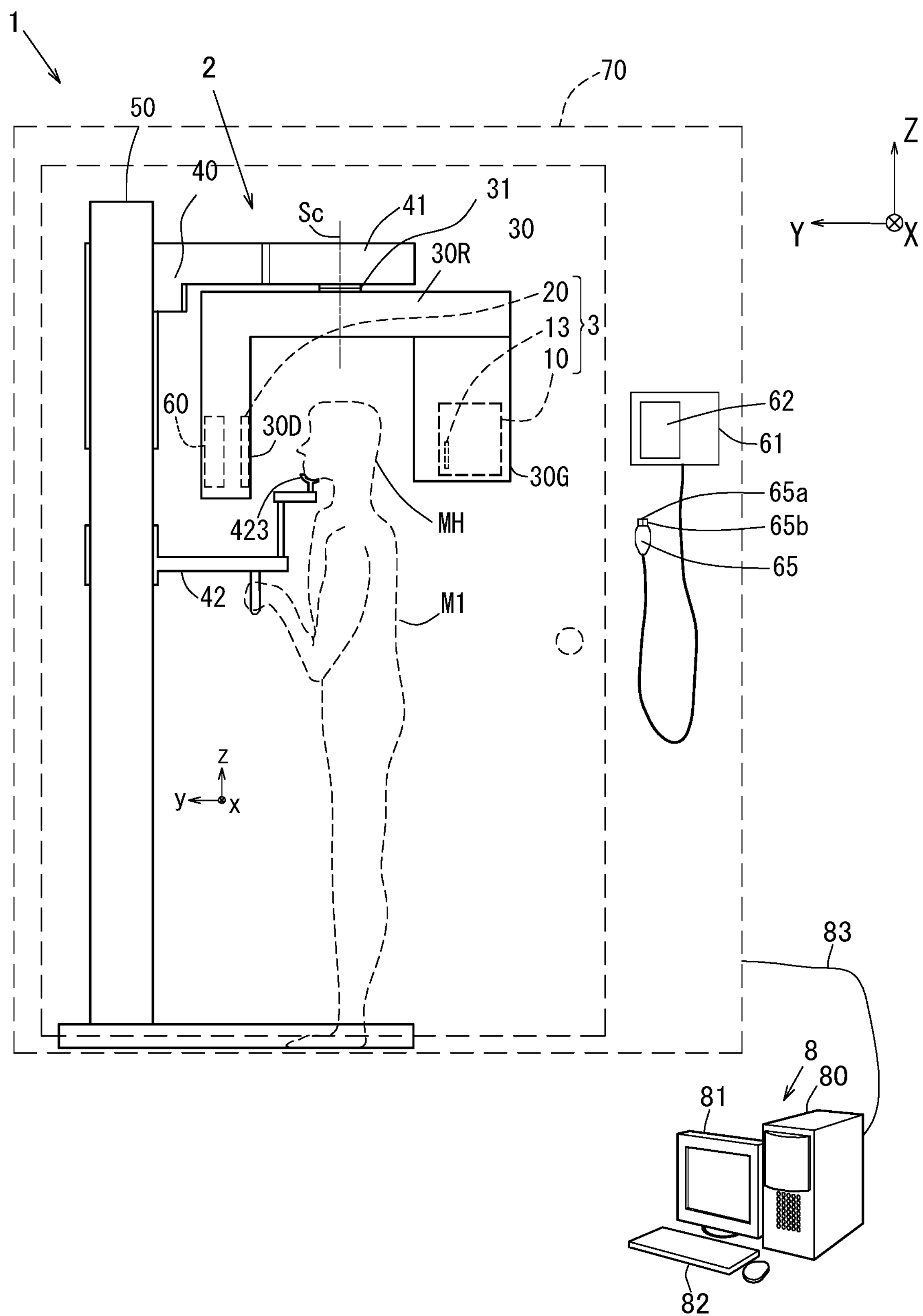
FIG. 1 is a schematic side view of an X-ray CT scanner.
Figure 2:
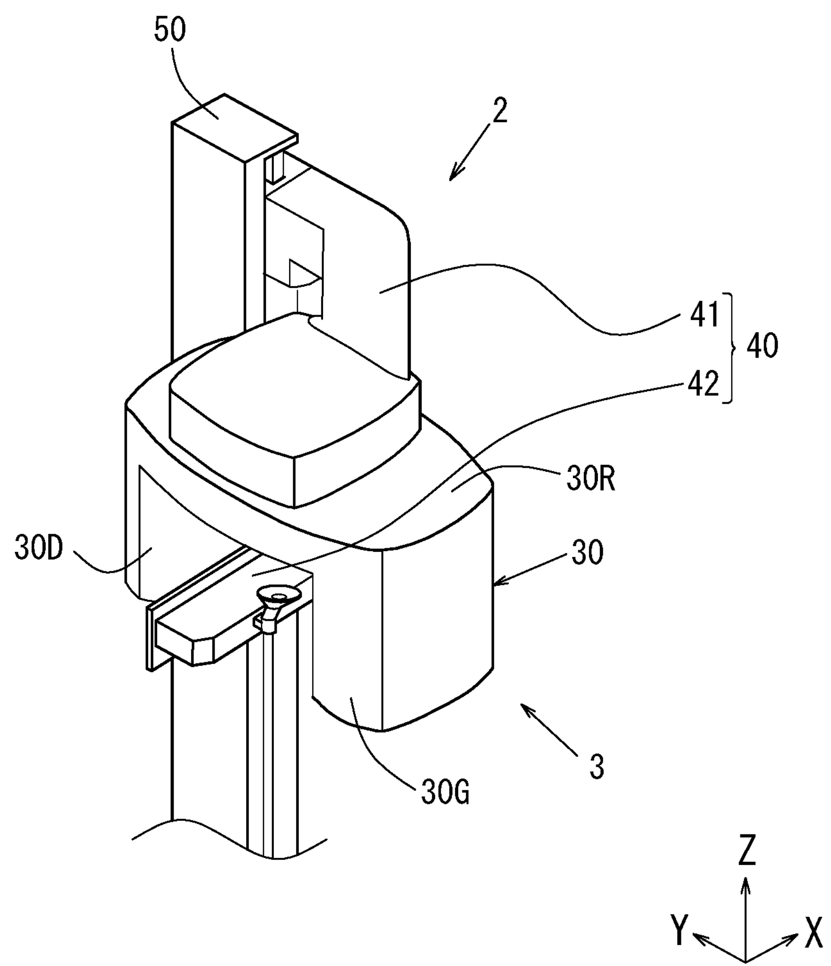
FIG. 2 is a partial perspective view of the X-ray CT scanner.
Figure 3:
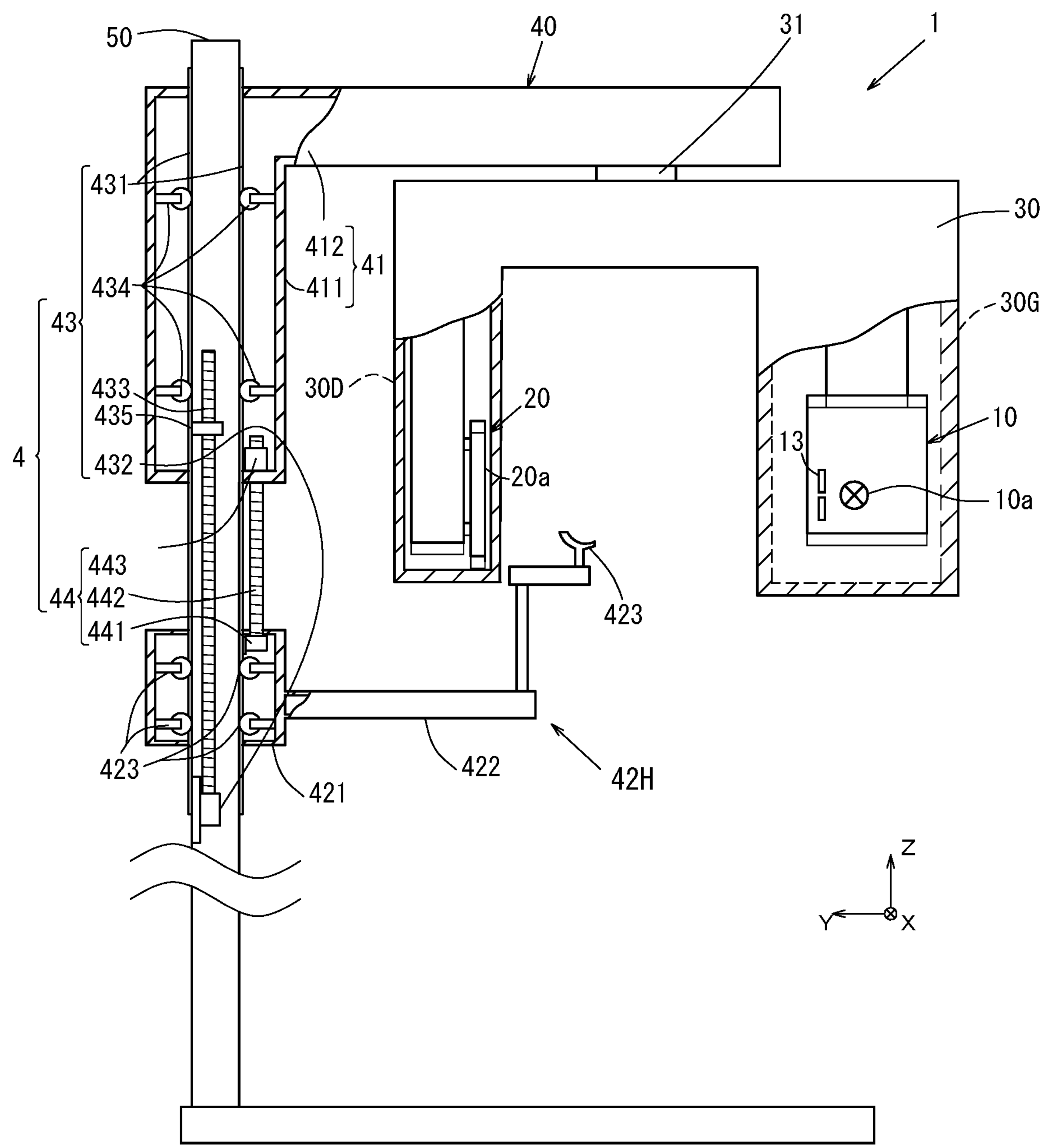
FIG. 3 illustrates an elevation structure of an upper frame.
Figure 4A:
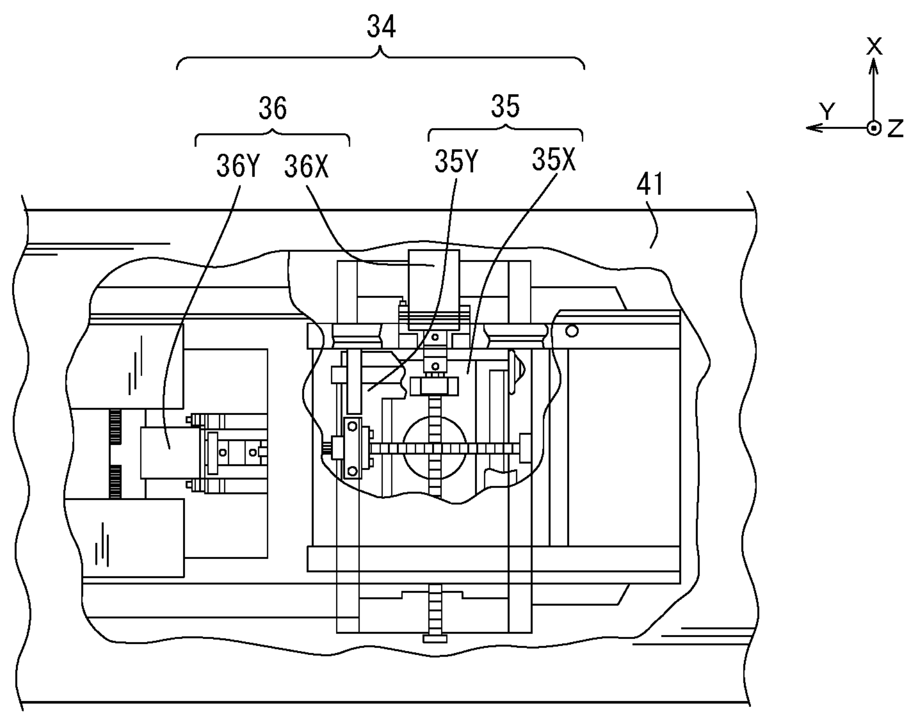
FIG. 4A and FIG. 4B illustrate an internal structure of a revolution arm and the upper frame that moves a revolution shaft.
Figure 4B:
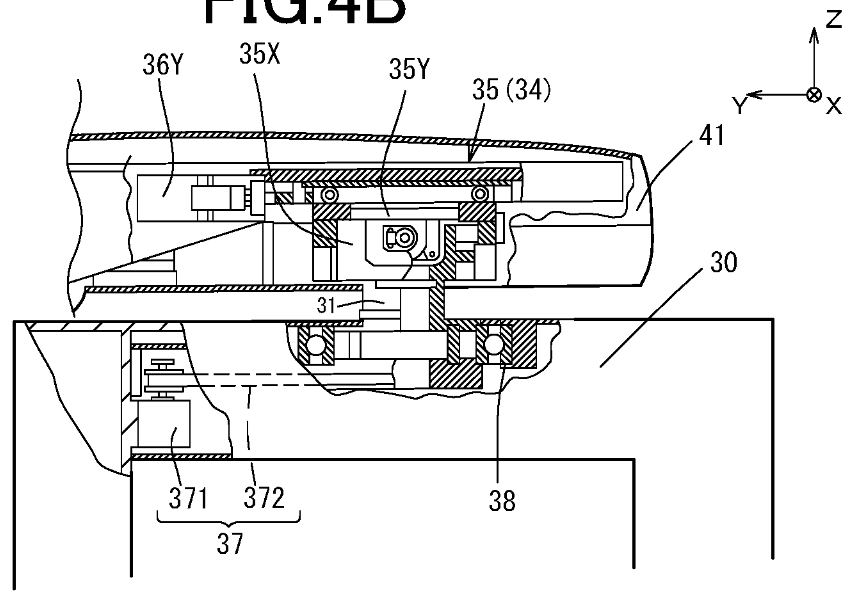
Figure 5:
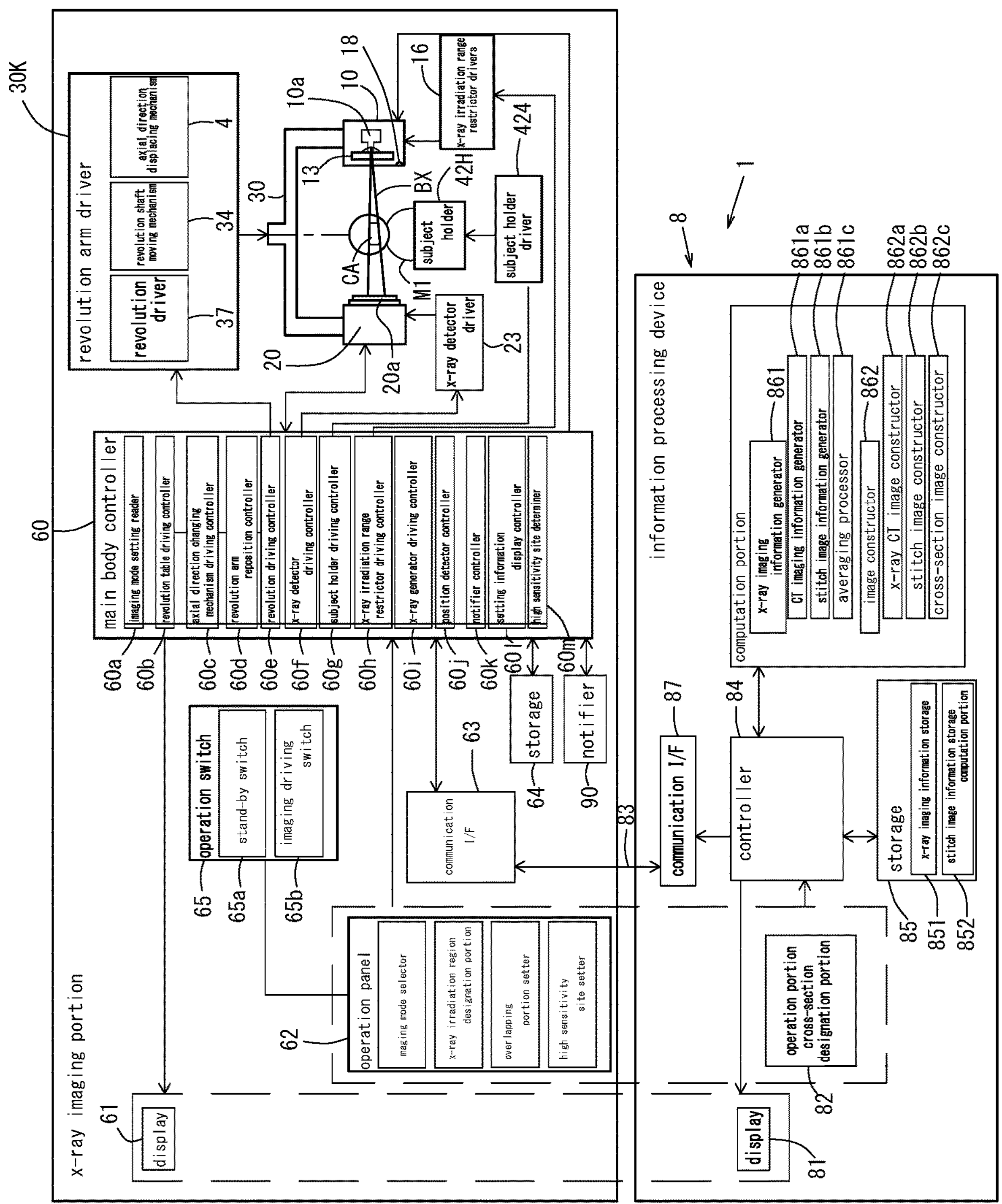
FIG. 5 is a block diagram showing a structure of the X-ray CT scanner.

FIG. 1 is a schematic side view of the X-ray CT scanner 1. FIG. 2 is a partial perspective view of the X-ray CT scanner 1. FIG. 3 illustrates an elevation structure of an upper frame 41. FIG. 4A and FIG. 4B illustrate an internal structure of a revolution arm 30 and the upper frame 41 that moves a revolution shaft. FIG. 5 is a block diagram showing a structure of the X-ray CT scanner 1.

Figure 6:
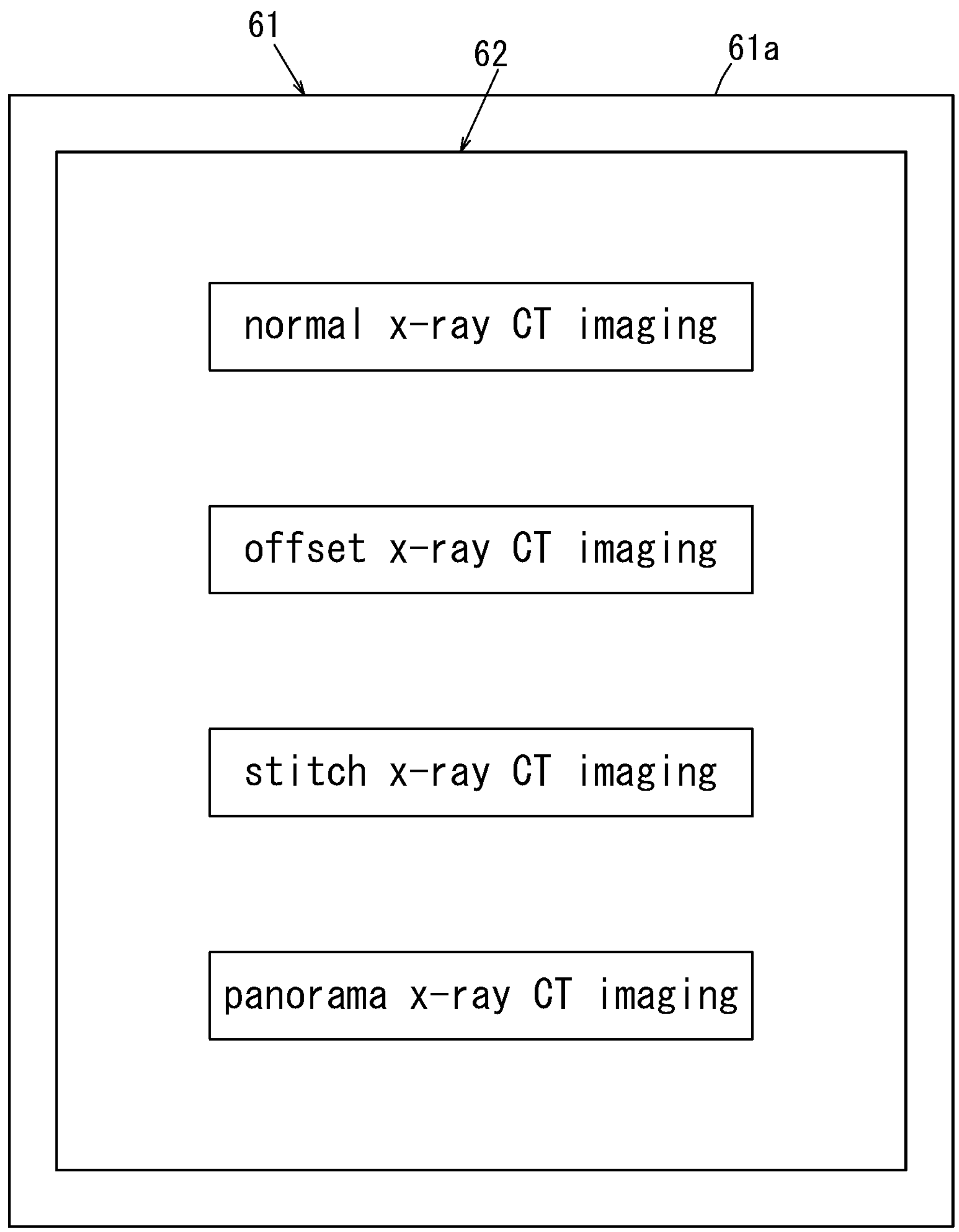
FIG. 6 illustrates an operation panel, by which an X-ray imaging method is selected.
Figure 7:
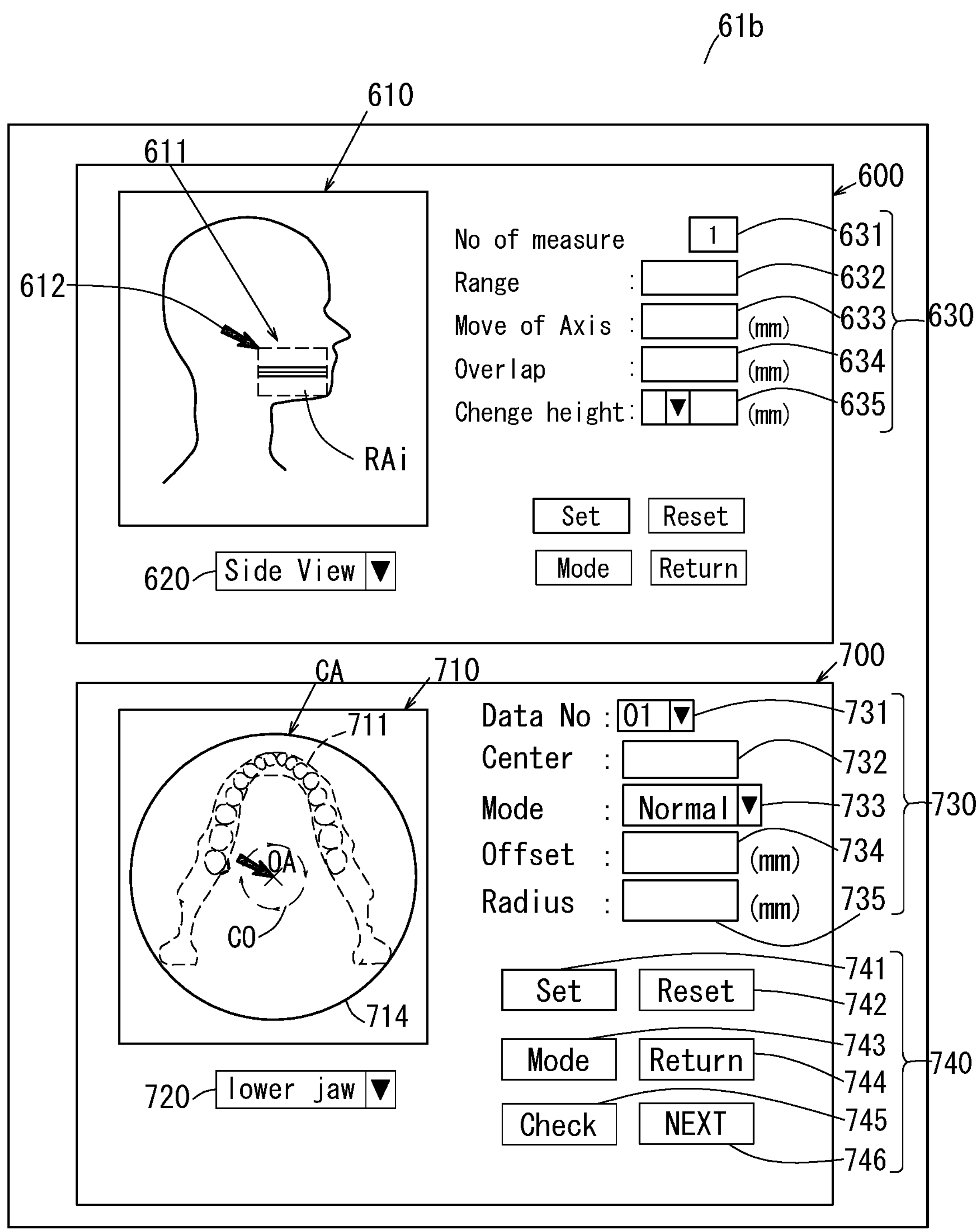
FIG. 7 illustrates the operation panel, by which imaging conditions are set.
Figure 8:
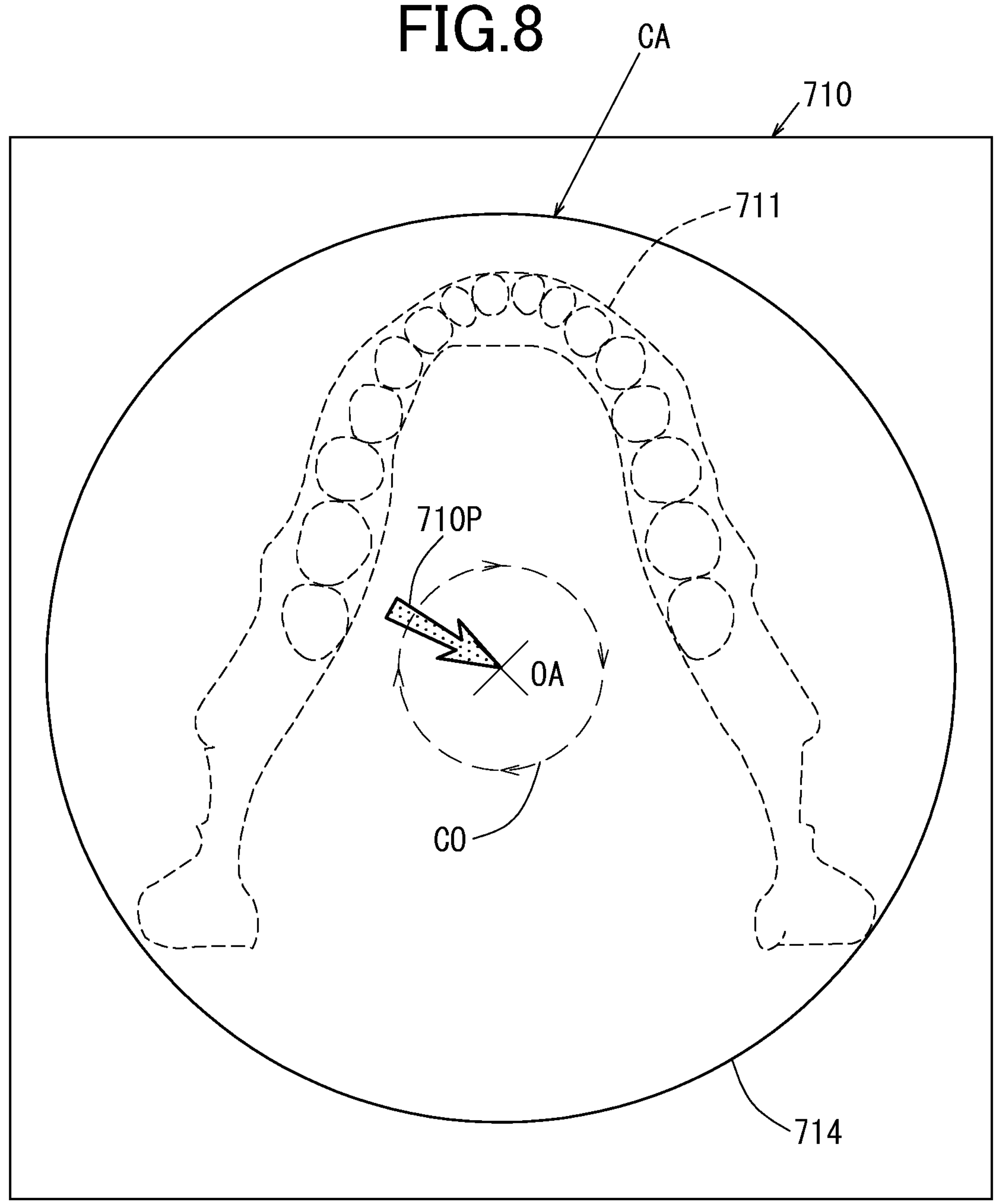
FIG. 8 is an enlarged schematic view showing an irradiation site displayed on the operation panel.
Figure 9:
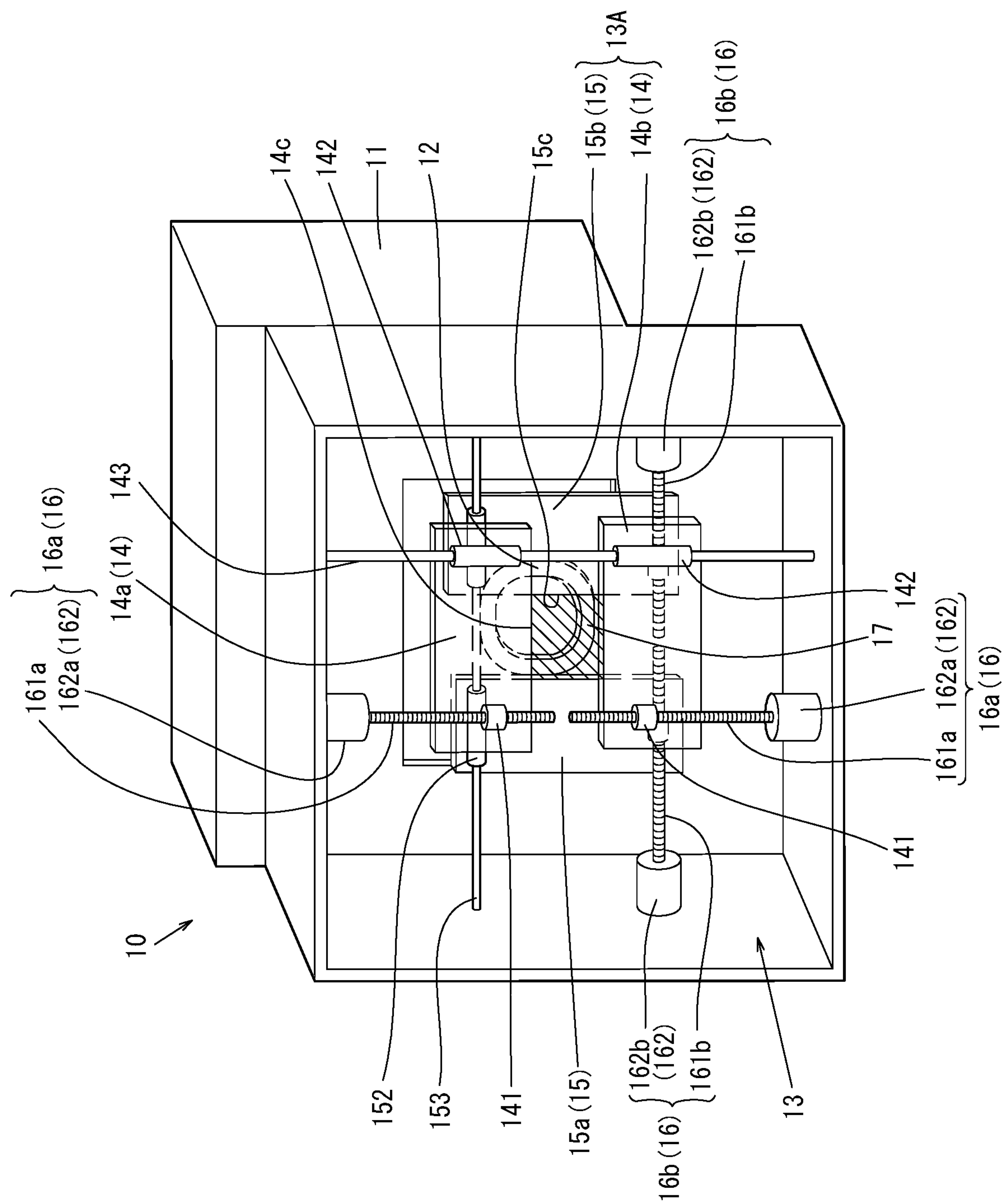
FIG. 9 is a schematic perspective view of a beam shaping mechanism.

FIG. 6 illustrates an operation panel 62, by which an X-ray imaging method is selected. FIG. 7 illustrates the operation panel 62, by which imaging conditions are set. FIG. 8 is an enlarged schematic view (dental arch image 711) showing an irradiation site displayed on the operation panel 62. FIG. 9 is a schematic perspective view of a beam shaping mechanism 13.

In more detail, FIG. 4A is a partial cross-sectional view showing an internal structure of the upper frame 41, and FIG. 4B is a partial cross-sectional view showing the internal structures of the revolution arm 30 and the upper frame 41. FIG. 4B shows the revolution arm 30 and the upper frame 41 in the case where the X-ray CT scanner 1 is seen from the side, and FIG. 4A shows the upper frame 41 as seen from above.

As shown in FIG. 1, the X-ray CT scanner 1 is roughly divided into a main body 2 performing X-ray CT imaging to collect projection data (volume data), and an information processing device 8 processing the projection data (volume data) collected by the main body 2 to generate an image such as an CT-captured image or the like. It is preferred that the main body 2 is accommodated in an X-ray-preventive chamber 70, which s hollow and has a parallelepiped shape longer in a vertical direction, and is connected with the information processing device 8, located outside the X-ray-preventive chamber 70, by a connection cable 83.

The main body 2 includes an X-ray generator 10 emitting, toward a subject M1, an X-ray cone beam Bx or an X-ray thin beam formed of a flux of X-rays, an X-ray detector 20 including an X-ray detection surface 20*a* detecting the X-ray emitted by the X-ray generator 10, a revolution arm 30 supporting the X-ray generator 10 and the X-ray detector 20, a support column 50 extending in the vertical direction, a revolution arm elevator 40 allowing the revolution arm 30 to suspend therefrom and movable up and down in the vertical direction with respect to the support column 50, and a main body controller 60. The X-ray generator 10, the X-ray detector 20 and the beam shaping mechanism 13 located in the X-ray generator 10 at a position closer to the X-ray detector 20 are included in an imaging mechanism 3.

As shown in FIG. 2 and FIG. 3, the X-ray generator 10 and the X-ray detector 20 are securely suspended at both of two ends of the revolution arm 30 and are supported so as to face each other. The revolution arm 30 is securely suspended by the revolution arm elevator 40 via a revolution shaft 31 extending in the vertical direction.

The revolution arm 30 is inverted-U-shaped as seen in a front view, and revolves about the revolution shaft 31, provided at a top end thereof, as a revolution center Sc. The revolution arm 30 includes a revolution portion 30R revolving about an axis of the revolution shaft 31, an X-ray generation portion 30G provided below one end of the revolution port on 30R and including the X-ray generator 10, and an X-ray detection portion 30D provided below the other end of the revolution portion 30R and including the X-ray detector 20.

The X-ray generator 10 and the X-ray detector 20 are respectively attached to both of the two ends of the revolution arm 30, which is inverted-U-shaped as seen in a front view. The revolution arm 30 not limited to having such a shape. For example, the X-ray generator 10 and the X-ray detector 20 may be supported, by a member rotatable about the center of an annular portion thereof as the rotation center, so as to face each other.

Hereinafter, a direction parallel to an axial direction of the revolution shaft 31 (herein, the vertical direction) will be referred to as a “Z-axis direction”, a direction crossing the Z-axis will be referred to as an “X-axis direction”, and a direction crossing the X-axis direction and the Z-axis direction will be referred to as a “Y-axis direction”. The X-axis and Y-axis directions may be arbitrarily defined. Herein, a left-right direction of a test subject, who is the subject M1, positioned in the X-ray CT scanner 1, specifically, a left-right direction of a head NH of the test subject facing the support column 50, will be defined as the X-axis direction. A front-rear direction of the test subject, specifically, a front-rear direction of the head MH of the test subject, will be defined as the Y-axis direction. In this embodiment, the X-axis direction, the Y-axis direction and the Z-axis direction are perpendicular to each other. Hereinafter, the Z-axis direction may be referred to as the vertical direction, and a direction on a plane defined two-dimensionally by the X-axis direction and the Y-axis direction may be referred to as a horizontal direction.

By contrast, regarding three-dimensional coordinates on the revolution arm 30, a direction in which the X-ray generator 10 and the X-ray detector face each other will be defined as a "y-axis direction", the horizontal direction perpendicular to the y-axis direction will be defined as an "x-axis direction", and the vertical direction perpendicular to the x-axis direction and the y-axis direction will be defined as a "z-axis direction". In this and the following embodiments, the Z-axis direction and the z-axis direction are the same direction as each other. In this embodiment, the revolution arm 30 revolves about the revolution shaft 31, extending in the vertical direction, as the rotation axis. Therefore, an xyz rectangular coordinate system is rotated about the Z-axis (=z-axis) with respect to an XYZ rectangular coordinate system.

As seen in a plan view of the X-ray generator 10 and the X-ray detector 20 shown in FIG. 1, a direction from the X-ray generator 10 toward the X-ray detector 20 will be defined as a (+y) direction. A direction that is perpendicular to the (+y) direction and is rightward for the positioned head MH will be defined as a "+x" direction. A vertically upward direction will be defined as a "+z" direction.

The revolution arm elevator 40 includes the upper frame 41 and a lower frame 42, and protrudes in one direction from an engagement end at which the revolution arm elevator 40 is in engagement with the support column 50 standing in the vertical direction, namely, protrudes generally rightward as seen in a front view of the support column 50 in the shown example.

The upper frame 41 and the lower frame 42 are coupled with each other by a subject holder elevator 44 described below.

The revolution shaft 31 of the revolution arm 30 is attached to the upper frame 41. The revolution arm elevator 40 moves in the vertical direction along the support column 50, and thus the revolution arm 30 may be moved on and down. The upper frame 41 includes an upper frame elevator 411, which is a part moving up and down along the support column 50, and an upper frame horizontal shaft 412 extending in the Y-axis direction with respect to the upper frame elevator 411.

As shown in FIG. 3, the upper frame 41, to which the revolution arm 30 is attached, is moved in the up-down direction by an axial direction changing mechanism 43 corresponding to an axial direction changing mechanism.

Hereinafter, the axial direction changing mechanism 43 will be described in detail. The axial direction changing mechanism 43 includes elevation rails 431, an elevation motor 432 and an elevation shaft 433 provided on the support column 50, and upper frame elevation wheels 434 and a first screw groove 435 provided on the revolution arm elevator 40. The axial direction changing, mechanism 43 is guided by the elevation rails 431, provided on the +Y direction side and the −Y direction side of the support column 50, to move up and down. Two of the upper frame elevation wheels 434 provided on the +Y direction side and two of the upper frame elevation wheels 434 provided on the −Y direction side of upper frame elevator 411 are rotatably attached.

The elevation motor 432 secured to the support column 50 is rotatable about the Z-axis direction as the rotation axis direction, and is attached such that the elevation shaft 433 axially rotatable in association with the rotation of the driven elevation motor 432 extends upward. With a top portion of the elevation shaft 433, the first screw groove 435 secured to the upper frame elevator 411 is engaged. Therefore, the upper frame 41 is movable in the up-down direction along the elevation rails 431 by the rotation of the driven elevation motor 432.

The lower frame 42 includes a lower frame elevator 421 movable up and down along the support column, and a subject holding arm 422 extending generally upward toward the upper frame 41 from the lower frame elevator 421. The subject holding arm 422 is provided with a head holder securing the subject M1 (herein, the human head MH) from left and right, and a subject securing portion 423 including, for example, a chin rest securing the chin and the like. An ear rod including portions insertable into left and right ear holes of the human head may be used for the subject securing portion 423.

The subject holding arm 422 and the subject securing portion 423 each having the above-described structure are included in a subject holder 42H holding the subject M1 (head MH).

In the lower frame elevator 421, two lower frame elevation wheels 425 and two lower frame elevation wheels 425 are rotatably attached to the elevation rails 431 respectively on the +Y direction side and the −Y direction side.

As shown in FIG. 3, the subject holder elevator 44 coupling the upper frame 4 and the lower frame 42 to each other includes a lower frame motor 441 secured to the support column 50, which is secured to the lower frame elevator 421, an elevation shaft 442 extending upward from the lower frame motor 441 and coupling the upper frame 41 and the lower frame 42 to each other, and a second screw groove 443 engaged with the elevation shaft 442 secured to the upper frame 41.

Like the elevation shaft 433, the elevation shaft 442 is attached to the lower frame motor 441 so as to be axially rotatable by the driving and rotation of the lower frame motor 441. The lower frame motor 441 is driven to rotate, and thus the upper frame 41 may be movable in the up-down direction with respect to the lower frame 42.

The lower frame motor 441 having the above-described structure is cooperated with the elevation motor 432, and thus only the upper frame 41 may be moved up and down or the upper frame 41 and the lower frame 42 may be moved up and down in association with each other.

The axial direction changing mechanism 43 having the above-described structure moves the revolution arm 30, which is a supporter, up and down, and the subject holder elevator 44 moves the subject holder 42H (subject securing portion 423) up and down or displaces the subject holder 42H with respect to the revolution arm 30 in accordance with the position of the subject M1 (head MH). As can be seen, the axial direction changing mechanism 43 and the subject holder elevator 44, which moves the revolution arm 30 up and down with respect to the subject M1, are included in an axial direction displacing mechanism 4.

As shown in FIG. 4, the upper frame 41 movable up and down with respect to the support column 50 includes a revolution driver 37 revolving the revolution arm 30 about the revolution shaft 31, and also includes a belt, a pulley, a rotation shaft and the like. A conveyance mechanism (not shown) running through the revolution shaft 31 conveys a rotation force provided by the revolution driver 37 to the revolution arm 30, and thus the revolution arm 30 may revolve. In this embodiment, the revolution shaft 31 extends in the vertical direction. Alternatively, the revolution shaft 31 may be inclined at an arbitrary angle with respect to the vertical direction.

In the shown example, the upper frame 41 includes a mechanical element that drives the revolution arm 30, and acts as an imaging mechanism driver. The upper frame 41 as the imaging mechanism driver drives the revolution arm 30 to drive the imaging mechanism 3.

The revolution driver 37 may be secured inside the upper frame 41. Alternatively, the revolution driver 37 may be secured inside the revolution arm 30 to cause a pivoting force to act on the revolution shaft 31.

A bearing 38 (see FIG. 4) is provided between the revolution shaft 31 and the revolution arm 30 described above so as to rotate the revolution arm 30 smoothly with respect to the revolution shaft 31.

Inside the upper frame 41, a revolution shaft moving mechanism 34 is provided.

As shown in FIG. 4, the revolution shaft moving mechanism 34 includes an KY table 35 moving the revolution shaft 31 together with the revolution arm 30 in the horizontal direction, and a driving motor 36 driving the XY table 35.

The XY table 35 includes a Y table 35Y moving the revolution arm 30 in the front-rear direction (Y-axis direction) and an X table 35X supported by the Y table 35Y to move in a lateral direction (X-axis direction).

The driving motor 36 includes a Y-axis driving motor 36Y driving the Y table 35Y and an X-axis driving motor 36K moving the X table 35X in, the X direction with respect to the Y table 35Y.

In the X-ray CT scanner 1, the driving motor 36 is connected with the main body controller 60, and performs driving in accordance with a predefined program to move the K table 35K in the left-right direction (X direction) and moves the Y table 35Y in the front-rear direction (Y direction) while revolving the revolution arm 30. As a result, the revolution shaft 31 may be controlled to move two-dimensionally, namely, in the X-Y directions i.e., in the front-rear direction and in the left-right direction.

The revolution shaft moving mechanism 34 acts as a two-dimensional moving mechanism that moves the revolution shaft 31 two-dimensionally in the horizontal direction with respect to the subject securing portion 423. A revolution motor 371, a revolution belt 372 conveying a rotation force of the revolution motor 371 to the revolution arm 30, and the like are included in the revolution driver 37.

In the above, the revolution shaft moving mechanism 34 is attached to the upper frame 41, and the revolution shaft 31 is movable in the planar direction. Alternatively, while the revolution shaft 31 is secured to the upper frame 41, the subject securing portion 423 located in the lower frame 42 may be configured to be movable in the planar direction with respect to the upper frame 41. Still alternatively, the upper frame 41 may include the revolution shaft moving mechanism 34, and the subject securing portion 423 may be configured to be movable with respect to the upper frame 41.

The axial direction displacing mechanism 4, the revolution shaft moving mechanism 34 and the revolution driver 37 having the above-described structure are included in a revolution arm driver 30K driving the revolution arm 30.

The main body controller 60 controls operations of components of the main body 2, and as shown in FIG. 1, is located inside the X-ray detector.

In more detail, the main body controller 60 is connected with the X-ray generator 10, an X-ray detector driver 23, the revolution arm driver 30K, a subject holder driver 424, X-ray irradiation range restrictor drivers 16 described below, a display 61, the operation panel 62 acting as an operation portion, a communication interface 63 (hereinafter, referred to as the "I/F 63") and a storage 64, and communicates with, and controls, each of the components.

The subject holder driver 424 drives the subject securing portion 423 (chin rest or the like), provided on the subject holding arm 422, to move up and down. More specifically, the subject holder driver 424 moves the lower frame elevator 421 up and down to drive the subject holder 42H.

In this embodiment, the display 61 includes a tough panel or the like, and thus has a part of functions of the operation panel 62. Namely, the display 61 also acts as the operation panel 62.

The operation panel 62 is connected with an operation switch 65. The operation switch 65 includes standby switch 65*a*, which is pressed before CT imaging to move the revolution arm 30 to an imaging start position Ps, and an imaging driving switch 65*b*, which is kept pressed to cause the X-ray cone beam Bx to be directed from the X-ray generator 10 toward the X-ray detector 20 and to revolve the revolution arm 30 to perform selected X-ray imaging.

The imaging driving switch 65*b* may be a well known switch conventionally called a "dead man switch". The imaging driving switch 65*b* may also have the function of the standby switch 65*a*, which, when being turned on for the first time, moves the revolution arm 30 to the imaging start position Ps (PO1), and while being turned on for the second time (while being kept pressed), keeps directing the X-ray cone beam Bx.

The communication I/F 63 is connected with a connection cable 83 of an information processing main body 80 to communicate with the information processing main body 80. The storage 64 stores information on a high sensitivity site H described below, a control program by which each of the components is controlled by the main body controller 60, projection data (volume data) provided by the X-ray imaging, and the like.

The high sensitivity site H may be registered regarding the position and the range as default settings, or may be configured to be registered and deleted optionally by an operator. Alternatively, it may be configured that a new high sensitivity site H may be registered and deleted by the operator in addition to the high sensitivity site H registered by the default settings.

The main body controller 60 connected with the components as described above cooperates with the control program stored on the storage 64 to act as an imaging mode setting reader 60*a* reading an imaging program in accordance with a selected imaging mode, a revolution table driving controller 60*b* control ling the revolution arm driver 30K, an axial direction changing mechanism driving controller 60*c*, a revolution arm position controller 60*d*, a revolution driving controller 60*e*, an X-ray detector driving controller 60*f* controlling the driving of the X-ray detector driver 23, a subject holder driving controller 60*g* controlling the driving of the subject holder driver 424, an X-ray irradiation range restrictor driving controller 60*h* controlling the driving of the X-ray irradiation range restrictor drivers 16, an X-ray generator driving controller 60*i* controlling the driving of the X-ray generator 10, a position detector controller 60*j* controlling a position, detector 18 detecting the positions of the X-ray generator 10 and the X-ray detector 20 and executing a position determination process, a notifier controller 60*k* controlling an operation of a notifier 90, a setting information control display 601 and a high sensitivity site determiner 60*m*.

Specifically, the imaging mode setting reader 60*a* executes reading control of reading the imaging program and the like stored on the storage 64 and a process of reflecting setting information, set by the operator, on the imaging program. The revolution table driving controller 60*b* controls the movement, in the horizontal direction, of the revolution shaft moving mechanism 34, specifically, the XY table 35. The axial direction changing mechanism driving controller 60*c* controls the axial direction changing mechanism 43 to adjust the movement, in the up-down direction, of the upper frame 41.

The revolution arm position controller 60*d* controls the movement of the revolution arm 30 to the imaging start position Ps during the X-ray imaging. The revolution driving controller 60*e* controls the driving, of the revolution driver to execute control regarding the setting of an X-ray revolution plane. The X-ray detector driving controller 60*f* controls the X-ray detector 20 such that the X-ray detector 20 is capable of detecting the X-ray cone beam Bx and also controls the movement of the X-ray detector 20, held by the revolution arm 30, in the up-down direction and the left-right direction. The subject holder driving controller 60*g* controls the subject holder elevator 44 to control the position adjustment of the subject M1.

The subject holder driving controller 60*g* controls the driving of the subject holder elevator 44. Namely, the axial direction changing mechanism driving controller 60*c* and the subject holder driving controller 60*g* control the axial direction displacing mechanism 4 to control the position adjustment of the subject M1 with respect to the revolution arm 30.

The X-ray irradiation range restrictor driving controller 60*h* uses the X-ray irradiation range restrictor drivers 16 to control the height and the width of an opening 17 of the beam shaping mechanism 13 described below, thus to execute control regarding the setting of the X-ray revolution plane. The X-ray generator driving controller 60*i* controls the X-ray generation by the X-ray generator 10, namely, controls the irradiation with the X-ray.

The X-ray cone beam Bx is directed while revolving, and therefore, forms a planar revolution track having a thickness as the revolution progresses. A plane formed by such a revolution track will be referred to as a "revolution plane".

The setting information control display 60*i* controls the display of an imaging condition setting screen 61*b* displayed on the display 61 (operation panel 62), the display of an imaging region expected based on the setting of the imaging conditions, and the like. The high sensitivity site determiner 60*m* executes a determination process of determining whether or not the X-ray cone beam Bx is to be directed toward the high sensitivity site.

The display 61 including a liquid crystal monitor or the like displaying various information based on the control of the main body controller 60, and the operation panel 62 including, for example, buttons by which various instructions to the main body controller 60 are input, are attached to an outer surface of a wall of the X-ray-preventive chamber 70 accommodating the main body 2.

As shown in FIG. 6, the display 61, which includes a touch panel monitor and thus also acts as input means, may display an imaging mode selection screen 61*a*, by which any of various types of X-ray imaging modes may be selected. The display 61 may also display the imaging condition setting screen 61*b* acting as an input screen, by which the position or the like of the imaging region of a biological organism or the like is designated and the imaging conditions are set in accordance with the selected imaging mode (see FIG. 7).

The operation panel 62 may be provided in the main body 2, or may be provided both on the outer surface of the wall of the X-ray-preventive chamber 70 and in the main body 2. Alternatively, the contents to be displayed on the display 61 may be played on a display 81 of the information processing device 8 instead of the display 61, and an operation may be performed via the communication I/F 63 and an communication I/F 87. The contents may be displayed both on the display 61 and the display 81.

Now, with reference to FIG. 7, an axial direction imaging region setting screen 600 and an offset imaging setting screen 700 included in the imaging condition set Ling screen 61*b* displayed on the display 61 will be described.

The imaging condition setting screen 61*b* is displayed in the case where "normal X-ray CT imaging", "offset X-ray CT imaging" or "stitch X-ray CT imaging" is selected on the imaging mode selection screen 61*a* (see FIG. 6) displayed on the display 61. The axial direction imaging region setting screen 600 is displayed only when the "stitch X-ray CT imaging" is selected.

As shown in FIG. 7, the axial direction imaging region setting screen 600 is provided to set an axial direction imaging range LA, which is an imaging range in the Z-axis direction in an imaging region CA (i.e., height of the imaging range), regarding the range to be processed by the stitch X-ray CT imaging.

The axial direction imaging region setting screen 600 includes an image display 610 displaying a schematic view of the head and the imaging region, a display setting selector 620, by which a schematic view to be displayed on the image display 610 is selected and set, an imaging condition setting display 630, by which conditions for the imaging region are set, and a condition setter 640, by which, for example, the imaging conditions set by the display setting selector 620 are saved.

The image display 610 includes a CT imaging range display 611 displaying a range, to be processed by the stitch X-ray CT imaging, as overlapping the schematic view of the subject, and a designation cursor (pointer) 612 designating, for example, the range that is to be processed by the stitch X-ray CT imaging and is to be displayed as overlapping in the CT imaging range display 611. For example, the imaging region is displayed as overlapping the schematic view of the subject in an imaging region display frame RAi, and an operation for deformation may be received by the imaging condition setting display 630 or the designation cursor 612 described below. Alternatively, the imaging region may be displayed in the display frame RAi with a default position and a default size, and an operation for movement or deformation may be added to the displayed imaging region.

The range, to be processed by the stitch X-ray CT imaging, that is displayed on the CT imaging range display 611 corresponds to a CT imaging range displayed on an image display 710 described below. Namely, the length, along the y-axis, of the range, to be processed by the stitch X-ray CT imaging, that is displayed on the CT imaging range display 611 has the same value as the diameter of the offset CT imaging range displayed on the image display 710.

The display setting selector 620 is an operation button by which a schematic view to be displayed on the CT imaging range display 611 is selected and set. With the display setting selector 620, a schematic view of the head as seen in a side view, a schematic view as seen in a front view, or a schematic view as seen at another angle, for example, a perspective view, may be selected.

In this embodiment, the schematic view is displayed on the CT imaging range display 611. Alternatively, images as seen at a plurality of angles, for example, a side view and a front view, may be displayed. The schematic view displayed on the CT imaging range display 611 may include the high sensitivity site H.

In the schematic view of the subject M1 displayed on the CT imaging range display 611, the head of the subject M1 may have the size and the shape of a standard skeleton, which has been read, or may show an internal structure such as a hard tissue, an important soft tissue or the like drawn to some extent.

The schematic view of the subject M1 displayed on the CT imaging range display 611 may be selected from a plurality of schematic views prepared in correspondence with body sizes, genders, adults and children, and the like. Alternatively, the schematic view may be a side image of the subject M1 or a schematic cross-sectional view of a designated predetermined site.

The imaging condition setting display 630, by which the imaging conditions in the Z-axis direction are set, includes an axial direction imaging number of times display 631 ("No of measure" in the figure), by which the number of times the imaging is to be performed in the Z-axis direction is set, an imaging region setting display 632 ("Range" in the figure), by which the width of an imaging region RA in the Z-axis direction, namely, the imaging range in the Z-axis direction is set, an axial direction moving distance setter 633 ("Move of Axis" in the figure), by which the distance by which the revolution arm 30 is to move in order to change the imaging region is set, an overlapping amount setter 634 ("Overlap" in the figure), by which an overlapping amount of imaging regions in the Z-axis direction is set, and an imaging region change setter 635 ("Change height" in the figure), by which a change in the height of the imaging region divided as a result of performing the imaging a plurality of times.

The value that is input to the axial direction imaging number of times display 631 is equal to the number by which the imaging region RA is divided. The value that is input to the imaging region setting display 632 is the sum of the lengths of a plurality of imaging regions R arrayed in the Z-axis direction.

The axial direction imaging number of times display 631, the imaging region setting display 632, the axial direction moving distance setter 633, the overlapping amount setter 634 and the imaging region change setter 635 store and display information that is preset in the program read from the storage 64 under the control of the imaging mode setting reader 60*a*. The preset information may respectively be optionally changed by directly inputting values to the text boxes of the axial direction imaging number of times display 631, the imaging region setting display 632, the axial direction moving distance setter 633, the overlapping amount setter 634 and the imaging region change setter 635. On the CT imaging range display 611 displayed on the image display 610, any of the individual imaging regions R arrayed in the axial direction may be designated by use of the designation cursor 612.

Hereinafter, an example of operation method of setting the imaging region on the axial direction imaging region setting screen 600 will be described.

First, a schematic view is selected by the display setting selector 620, and the selected schematic view is displayed on the image display 610. At this point, the imaging region display frame RAi is displayed in the schematic view. The imaging region display frame RAi is moved or deformed by use of the designation cursor 612, and thus the numerical values displayed on the imaging region setting display 632, the axial direction moving distance setter 633, the overlapping amount setter 634 and the imaging region change setter 635 are changed in accordance with the imaging region display frame RAi and are displayed. These numerical values may each be updated by inputting a numerical value to the corresponding text box, and such an input value is reflected on the CT imaging range display 611 (imaging region display frame RAi).

The imaging region setting display 632, the axial direction moving distance setter 633, the overlapping amount setter 634 and the imaging region change setter 635 may merely have a function of displaying the results of operation performed by use of the designation cursor 612.

The condition setter 640 includes a Set button 641, a Reset button 642, a Mode button 643, and a Return button 644.

The Set button 641 is an operation button by which detailed information regarding the imaging conditions that are designated by use of the designation cursor 612 and set and displayed by the display setting selector 620 is saved.

The Reset button 642 is an operation button by which the designation of the imaging conditions by the designation cursor 612 and the detailed information set and displayed by the display setting selector 620 are reset.

The Mode button 643 is an operation button by which the screen is returned to the imaging mode selection screen 61*a*. The Return button 644 is an operation button by which the screen is returned to an initial screen (not shown).

Now, the offset imaging setting screen 700 displayed below the axial direction imaging region setting screen 600 on the imaging condition setting screen 61*b* will be described.

As shown in FIG. 7, the of f set imaging setting screen 700 is provided to set the imaging region CA enclosing an imaging target site OB, more precisely, a planar imaging range P, which is as an imaging range on the XY plane. The offset imaging setting screen 700 includes an image display 710 displaying the dental arch image 711 or the like, an upper/lower jaw selector 720, a selected range setter 730, and a condition setter 740.

Hereinafter, the image display 710 will be described in detail with reference to FIG. 8.

As shown in FIG. 8, on the image display 710, the dental arch image 711 and a CT imaging region line 714, which shows a CT imaging region centered around an imaging center OA, are displayed in an overlapping manner.

The imaging center OA is a point that matches the imaging central axis of the imaging mechanism 3, and may be set at an arbitrary position by, for example, a pointer 710P. Alternatively, the imaging center OA may be defined at a default position and movable by the pointer 710P. Still alternatively, the CT imaging region line 714 may be deformed by the pointer 710P to change the size of the imaging region.

The pointer 710P is displayed by a touch operation on the operation panel 62 or by the movement of a mouse. For example, the touched point or the point indicated by the mouse, when being on the image display 610, is the designation cursor (pointer) 612. The point indicated by the mouse, when being on the image display 710 as a result of the movement of the mouse, is the pointer 710P.

With the upper/lower jaw selector 720, the dental arch image 711 to be displayed on the image display 710 is selected. The upper/lower jaw selector 720 includes an UPPER button by which the imaging region CA is set to the upper jaw, a FULL button by which the imaging region CA is set to both of the upper jaw and the lower jaw, and a LOWER button by which the imaging region CA is set to the lower jaw. Any of the UPPER button, the FULL button and the LOWER button may be selected. In FIG. 7, the LOWER button is selected to set the imaging region CA to the lower jaw.

The selected range setter 730 includes an imaging number designator 731 ("Data of No" in the figure), by which the order number of the imaging to be performed by the stitch X-ray CT imaging is designated, a center display 732 ("Center" in the figure), by which coordinates of an imaging center O of the X-ray CT imaging designated by the imaging number designator 731 are displayed, an imaging method selection button 733 ("Mode" in the figure), by which the imaging mode of the X-ray CT imaging designated by the imaging number designator 731 is splayed, an offset center designator 734 ("Offset" in the figure), by which the revolution center Sc (described below) in the offset X-ray CT imaging is designated on the image display 710, and a radius designator 735 ("Radius" in the figure), by which the distance between the imaging center OA and the CT imaging region line 714 is calculated as the radius of a circular imaging region and controlling the setting thereof.

In the text boxes of the center display 732, the offset center designator 734 and the radius designator 735, the results of the operation performed by use of the pointer 710P (designation cursor 612) on the image display 710 are displayed. The numerical values in the text boxes are rewritten appropriately to change the CT imaging region line 714 on the image display 710.

Now, an example of operation method of setting the imaging center OA and the imaging range on the offset imaging setting screen 700 will be described.

The pointer 710P is mowed to select the upper/lower jaw selector 720, and thus a schematic view of a target dental arch (herein, a schematic view of the lower law) is displayed on the image display 710. At this point, the imaging, center OA is displayed on the schematic view displayed on the image display 710 as a default setting. Therefore, the pointer 710P is used to move the imaging center OA to a desired position.

As a result, numerical values corresponding to predetermined positions are displayed in the center display 732, the offset center designator 734 and the radius designator 735. These numerical values are rewritten to change the CT imaging region line 714 on the image display 710.

The center display 732, the offset center designator 734 and the radius designator 735 may merely have a function of displaying the results of the operation performed by use of the designation cursor 612 (pointer 710P). Alternatively, the CT imaging region may be selected from a plurality of prepared CT imaging regions.

The imaging region display frame RAi displayed on the image display 610 and the CT imaging region line 714 are associated with each other. When one of the two is moved or deformed, the other of the two is also moved or deformed accordingly.

The condition setter 740 includes a Set button 741, a Reset button 742, a Mode button 743, a Return button 744, a NEXT button 745, and a Check button 746.

The Set button 741 is an operation button by which the contents designated regarding the imaging region CA set by the image display 710, the upper/lower jaw selector 720 and the selected range setter 730 are saved.

The Reset button 742 is an operation button by which the contents designated regarding the imaging region CA set by the image display 710, the upper/lower law selector 720 and the selected range setter 730 are reset.

The Mode button 743 is an operation button by which the screen is returned to the imaging mode selection screen 61*a*, by which any of various modes is selected. The Return button 744 is an operation button by which the screen is returned to the initial screen (not shown).

The NEXT button 745 is an operation button by which the screen is returned to a setting screen by which the imaging conditions, other than the imaging region, that are set by the imaging number designator 731 are set. The Check button 746 is an operation button by which it is checked whether or not imaging is possible under the set imaging conditions.

The imaging conditions are input to the axial direction imaging region setting screen 600 and the offset imaging setting screen 700 each having the above-described structure, and the operation switch 65 is operated. Thus, the imaging of the imaging region CA of the subject M1 may be performed under the set imaging conditions.

In this embodiment, the axial direction imaging region setting screen 600 and the offset imaging setting screen 700 described above are displayed on the operation panel 62. Alternatively, the axial direction imaging region setting screen 600 and the offset imaging setting screen 700 may be displayed on the display 81 described below. In this case, desired imaging conditions are input to the text boxes of the axial direction imaging region setting screen 600 and the offset imaging setting screen 700 displayed on the display 81, and the input information is transmitted via the communication I/F 63 and the communication I/F 87. Thus, the imaging conditions for the subject M1 may be set.

The information processing device 8 includes an information processing main body 80, the display 81 including a display device such as, for example, a liquid crystal monitor or the like, an operation portion 82 including a keyboard, a mouse or the like, a controller 84, a storage 85 storing, for example, a control program by which each of the components is controlled by the controller 84, a computation portion 86, and the communication I/F 87.

The display 81, the operation port on 82, the storage 85 and the computation port on 86 are connected with the controller 84. The controller 84 cooperates with the control program stored on the storage 85 to control each of the components. The computation portion 86 cooperates with an image processing program stored on the storage 85 to act as an image processor. The computation portion 86 includes an X-ray imaging information generator 861 generating CT imaging information I based on the projection data (volume data) and an image constructor 862 performing based on the X-ray imaging information generated by the X-ray imaging information generator 861.

Specifically, the X-ray imaging information generator 861 includes a CT imaging information generator 861*a* executing a process of generating the CT imaging information I based on projection data acquired by the X-ray imaging (three-dimensional volume data acquired as a result of, for example, inverse-projecting the projection data), a stitch image information generator 861*b* executing a process of generating the stitch imaging information is, which is acquired as a result of joining pieces of the X-ray imaging information generated based on the projection data (volume data), and an averaging processor 861*c* performing an averaging process on overlapping image information Iw regarding an overlapping portion of the pieces of the X-ray imaging information based on which the stitch imaging information Is is generated.

The image constructor 862 acts as a processor of constructing a CT-captured image C based on the X-ray imaging information generated by the X-ray imaging information generator 861. The image constructor 862 includes an X-ray CT image constructor 862*a* executing a process of constructing the CT-captured image G based on the CT imaging information I, a stitch image constructor 862*b* executing a process of constructing a stitch image Gs based on the stitch imaging information Is, and a cross-section image constructor 862*c* executing a process of generating sectional image information at a designated position and constructing a cross-section image Gc.

The CT imaging information I generated by the CT imaging information generator 861*a* is stored on an X-ray imaging information storage 851 included in the storage 85, and the stitch imaging information IS is generated by the stitch image information generator 861*b* is stored on a stitch image information storage 852.

The operator may input various instructions to the information processing device 8 having the above-described structure via the operation portion 82.

The display 81 may include a touch panel. In this case, the display 81 has a part of, or all of, the functions of the operation portion 82, and also acts as the operation portion 82.

Images of various buttons and the like may be displayed on the display 81, so that the pointer may be operated by the mouse or the like. In this case also, the display 81 acts as the operation portion 82.

The information processing main body 80 includes, for example, a computer, a work station or the like, and may transmit and receive various data to and from the main body 2 by the connection cable 83, which is a communication cable, via the communication I/F 87. It should be noted that the data may be exchanged wirelessly between the main body 2 and the information processing device 8.

Now, with reference to FIG. 9, the beam shaping mechanism 13 will be described, which blocks and restricts the irradiation range of the X-ray generated by the X-ray generator 10 to form the X-ray cone beam Bx expanding in a truncated pyramid shape toward the X-ray detector 20.

The X-ray generator 10 located to face the X-ray detector 20 in the revolution arm 30 includes an X-ray emitter 10*a*, including an X-ray tube, accommodated in a housing 11. A front face of the housing 11 has an emission opening 12 allowing the transmission of the X-ray generated by the X-ray generator 10 accommodated in the housing 11. The beam shaping mechanism 13 is located to the front of the emission opening 12 (on the side of the viewer of FIG. 9, and in the y-axis direction with respect to the X-ray generator 10).

The position detector 18 detecting the positions of the X-ray generator 10 and the X-ray detector 20 is provided at a bottom end of the housing 11.

The position detector 18 may include a velocity sensor, an angular velocity sensor, an angle sensor, a gyrosensor, or a combination of at least two of these sensors. In the case where, for example, the revolution driver 37 and the driving motor 36 each include a pulse motor, the positions may be detected by a coordinate operation from numerical values counted by a pulse counter or the like.

The beam shaping mechanism 13 includes length direction blocking plates 14 (14*a*, 14*b*) blocking the X-ray irradiation range in the length direction (z direction), lateral direction blocking plates 15 (15*a*, 15*b*) blocking the X-ray irradiation range in the lateral direction (x direction) and X-ray irradiation range restrictor drivers 16 (16*a*, 16*b*) moving the length direction blocking plates 14 and the lateral direction blocking plates 15.

The length direction blocking plates 14 include an upper length direction blocking plate 14*a* and a lower length direction blocking plate 14*b*, which are longer in the lateral direction and are respectively located above and below the emission opening 12 as seen in a front view. The lateral direction blocking plates 15 include a left lateral direction blocking plate 15*a* and a right lateral direction blocking plate 15*b*, which are longer in the length direction and are respectively located to the left of, and to the right of, the emission opening 12 as seen in a front view. As shown in FIG. 9, the lateral direction blocking plates 15 are located closer to the X-ray generator 10 than the length direction blocking plates 14. Alternatively, the length direction blocking plates 14 may be located closer to the X-ray generator 10 than the lateral direction blocking plates 15.

The X-ray irradiation range restrictor drivers 16 include blocking plate length direction moving mechanisms 16*a* moving the two length direction blocking plates 14 in the length direction, and blocking plate horizontal direction moving mechanisms 16*b* moving the two lateral direction blocking plates 15 in the lateral direction.

The blocking plate vertical direction moving mechanisms 16*a* respectively use position adjusting motors 162*a* (162) to rotate length direction screw shafts 161*a* in engagement with screw grooves 141 (guided members each having an inner female thread) arrayed in the length direction in correspondence with the length direction blocking plates 14, and thus move the length direction blocking plates 14 in the length direction. The blocking plate vertical direction moving mechanisms 16*a* are respectively located above the upper length direction blocking plate 14*a* and below the lower length direction blocking plate 14*b*. Therefore, the upper length direction blocking plate 14*a* and the lower length direction blocking plate 14*b* are movable in the length direction independently.

The blocking plate vertical direction moving mechanisms 16*a* are located as being offset in the lateral direction with respect to the length direction blocking plates 14, which are longer in the lateral direction. A restriction shaft 143 is provided on the opposite side to the blocking plate vertical direction moving mechanisms 16*a* in the lateral direction. The restriction shaft 143 includes inclination restriction holes 142 (guided members each having an inner through-hole extending in the length direction) and runs through the inclination restriction holes 142 corresponding to both of the upper length direction blocking plate 14*a* and the lower length direction blocking plate 14*b*. Therefore, the length direction blocking plates 14 are movable in the length direction by the X-ray irradiation range restrictor drivers 16 without being inclined.

The blocking plate horizontal direction moving mechanisms 16*b* respectively use position adjusting motors 162*b* (162) to rotate lateral direction screw shafts 161*b* in engagement with screw grooves 161 (guided members each having an inner female thread) arrayed in the lateral direction in correspondence with the lateral direction blocking plates 15, and thus move the lateral direction blocking plates 15 in the lateral direction. The blocking plate horizontal direction moving mechanisms 16*b* are respectively located to the left of the left lateral direction blocking plate 15*a* and to the right of the right lateral direction blocking plate 15*b*. Therefore, the left lateral direction blocking plate 15*a* and the right lateral direction blocking plate 15*b* are movable in the lateral direction independently.

The blocking plate horizontal direction moving mechanisms 16*b* are located as being offset in the lateral direction with respect to the lateral direction blocking plates 15, which are longer in the length direction. A restriction shaft 153 is provided on the opposite side to the blocking plate horizontal direction moving mechanisms 16*b* in the lateral direction. The restriction shaft 153 includes inclination restriction holes 152 and runs through the inclination restriction holes 152 (guided members each having an inner through-hole extending in the lateral direction) corresponding to both of the left lateral direction blocking plate 15*a* and the right lateral direction blocking plate 15*b*. Therefore, the lateral direction blocking plates 15 are movable in the lateral direction by the blocking plate horizontal direction moving mechanisms 16*b* without being inclined.

As described above, the beam shaping mechanism 13 includes the length direction blocking plates 14, the lateral direction blocking plates 15 and the X-ray irradiation range restrictor drivers 16, and is located to the front of the emission opening 12 of the X-ray generator 10. Thus, the X-ray irradiation range of the X-ray generated by the X-ray generator 10 may be blocked and restricted to form the X-ray cone beam Bx expanding in a truncated pyramid shape toward the X-ray detector 20.

This will be described in more detail. The interval between facing edges 14*c* of the upper length direction blocking plate 14*a* and the lower length direction blocking plate 14*b* is adjusted by the blocking plate vertical direction moving mechanism 16*a*, and the interval between facing edges 15*c* of the left lateral direction blocking plate 15*a* and the right lateral direction blocking plate 15*b* is adjusted by the blocking plate horizontal direction moving mechanisms 16*b*. Thus, the facing edges 14*c* of the upper length direction blocking plate 14*a* and the lower length direction blocking plate 14*b*, and the facing edges 15*c* of the left lateral direction blocking plate 15*a* and the right lateral direction blocking plate 15*b*, form an opening 17 forming the X-ray cone beam Bx having a desired shape. The opening 17 is square as seen in a front view.

The beam shaping mechanism 13 having the above-described structure may restrict the irradiation range of the X-ray cone beam Bx directed from the X-ray emitter 10*a* when the X-ray cone beam Bx passes the opening 17 formed by an X-ray irradiation range restrictor 13A. As described above, the X-ray irradiation range restrictor drivers 16 are connected with the main body controller 60, and may restrict the irradiation range to a desired range by the X-ray irradiation range restrictor dr wing controller 60*h*.

The X-ray cone beam Bx is not limited to having a truncated pyramid shape.

For example, the number of the blocking plates may be increased, so that a polygonal-shaped X-ray cone beam having a cross-section, perpendicular to the irradiation axis of the X-ray, that is pentagonal or has a greater number of sides may be formed. Alternatively, the structure of a diaphragm of a camera usable to perform well-known visible light imaging may be adapted to block the X-ray irradiation range such that the X-ray irradiation range is of a circle having a variable diameter. In this case, a conical X-ray cone beam having a cross-section, perpendicular to the irradiation axis of the X-ray, that is circular may be formed, and the three-dimensional shape of the X-ray CT imaging region may be spherical.

In the case where the X-ray CT scanner 1 having the above-described structure is used, the CT imaging information I on an region of interest is generated even in the case where the X-ray detection surface 20*a* of the X-ray detector 20 is small. A method for such generation will be described below with reference to FIG. 10 through FIG. 18.

Figure 10:
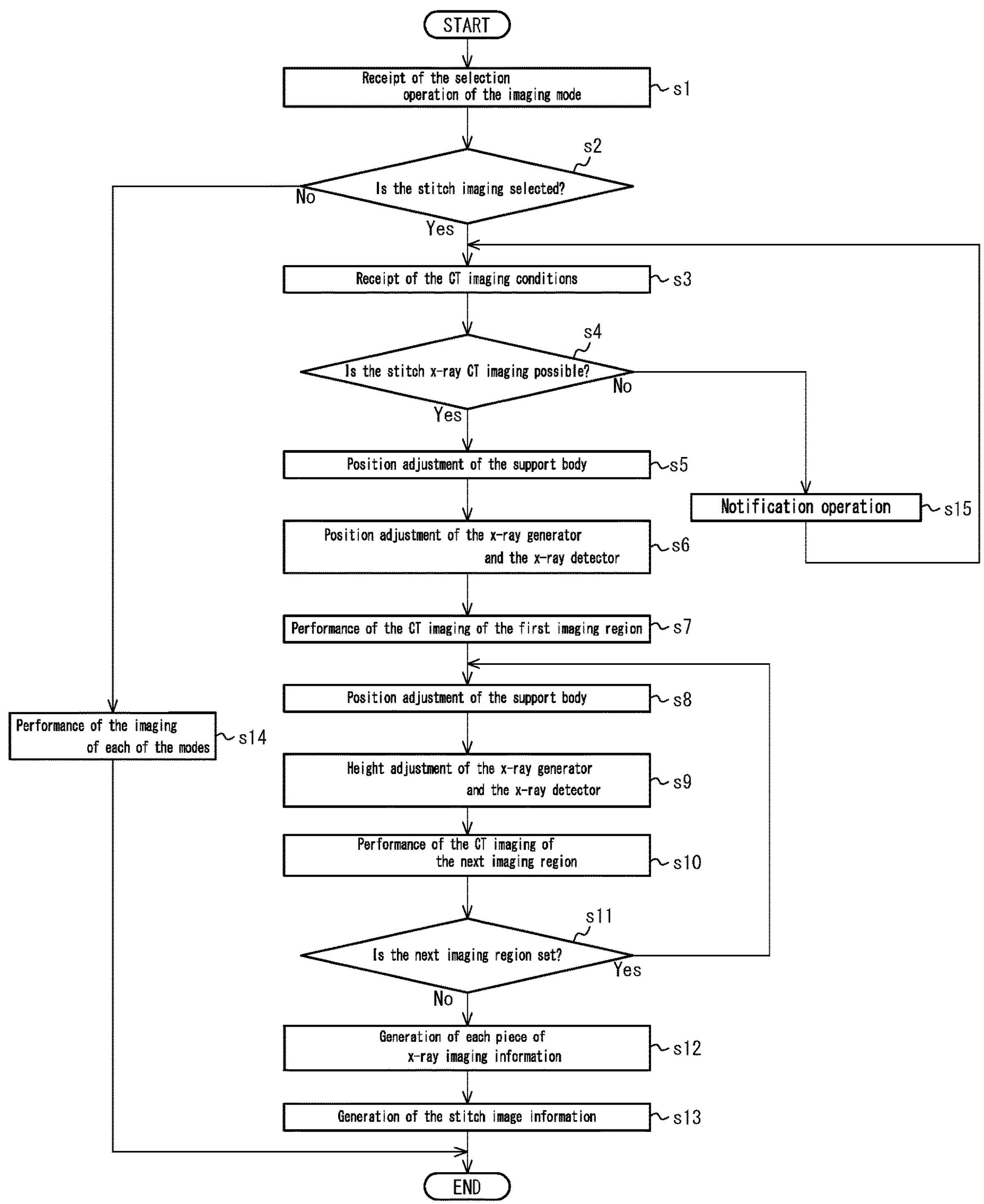
FIG. 10 is a flowchart of stitch X-ray CT imaging.
Figure 11:
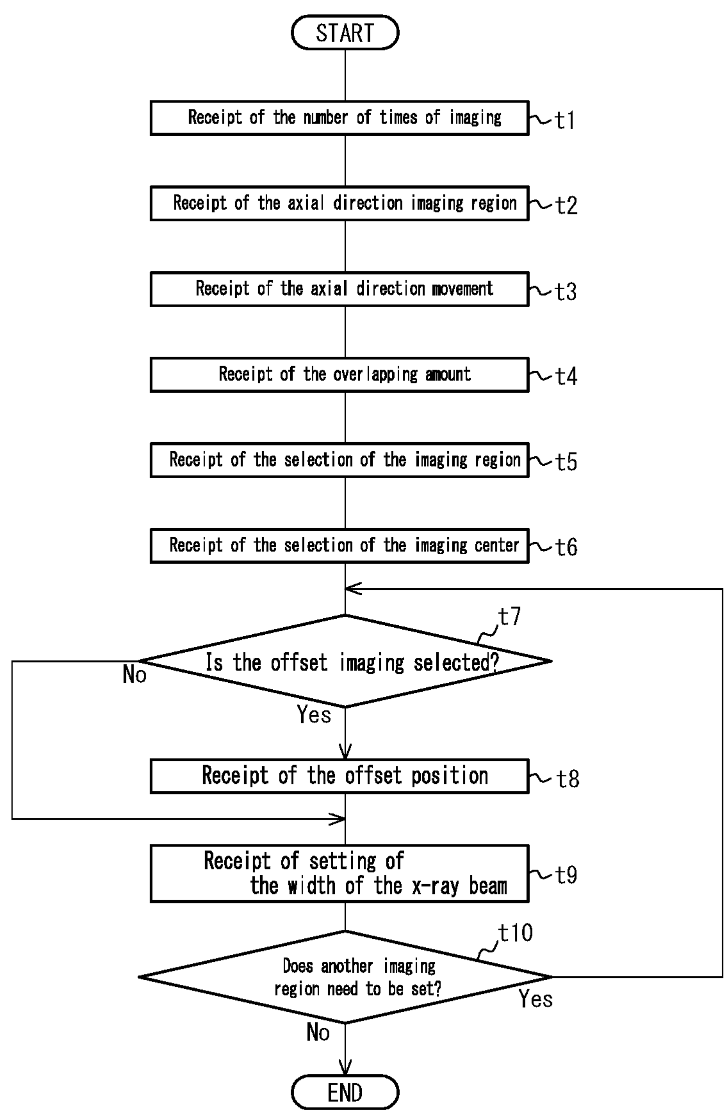
FIG. 11 is a flowchart of receipt of CT imaging conditions.

FIG. 10 is a flowchart of the stitch X-ray CT imaging using the X-ray CT scanner 1. FIG. 11 is a flowchart showing step s3 (receipt of CT imaging conditions) in FIG. 10 in detail.

Figure 13:
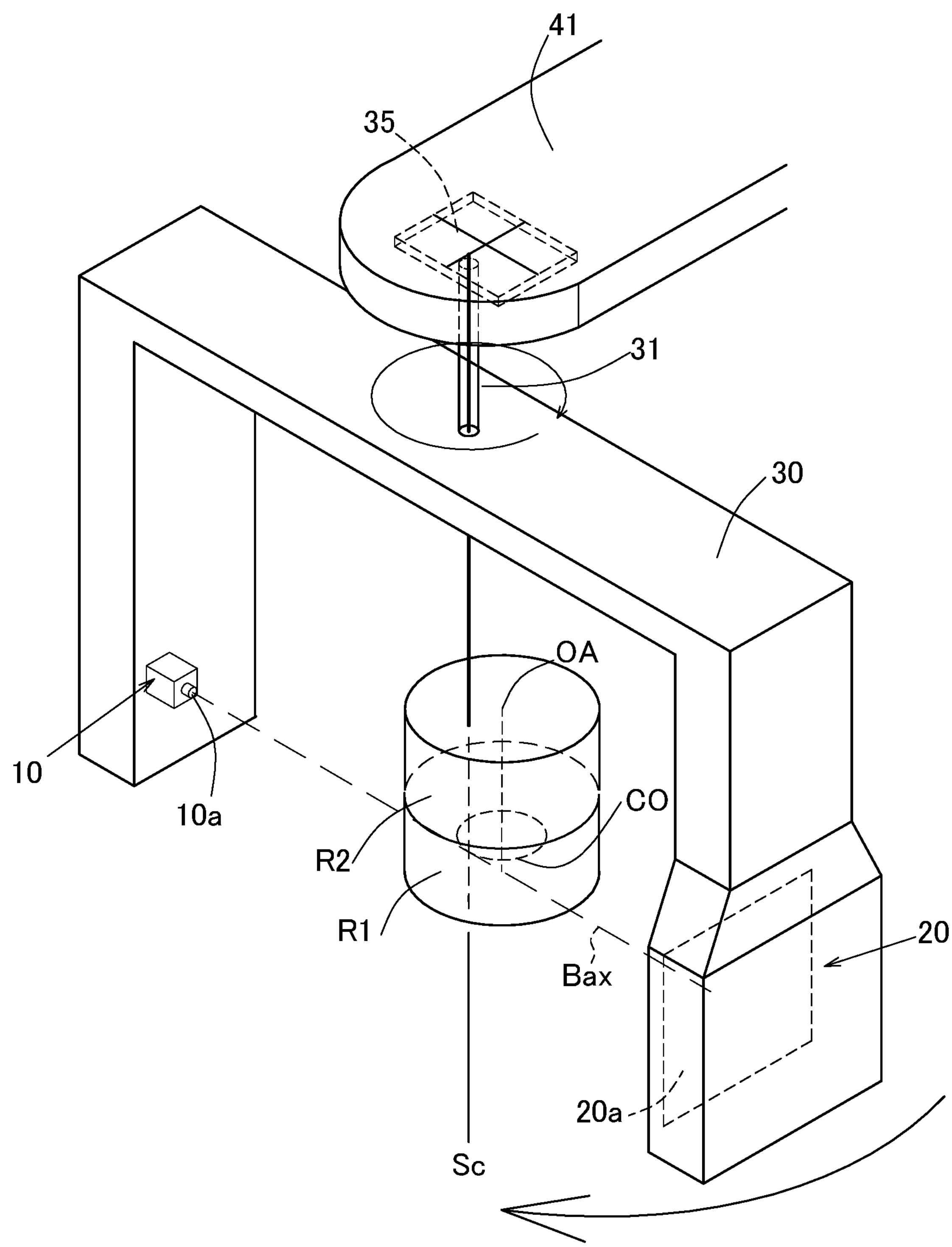
FIG. 13 is a schematic perspective view showing as imaging start position of an X-ray generator and an X-ray detector in imaging of a first imaging region.

FIG. 13 is a perspective view showing the positions of the X-ray generator 10 and the X-ray detector 20 at the start of the offset X-ray CT imaging of a first imaging region R1, FIG. 14 and FIG. 15 show the offset CT imaging of the first imaging region R1.

Figure 16:
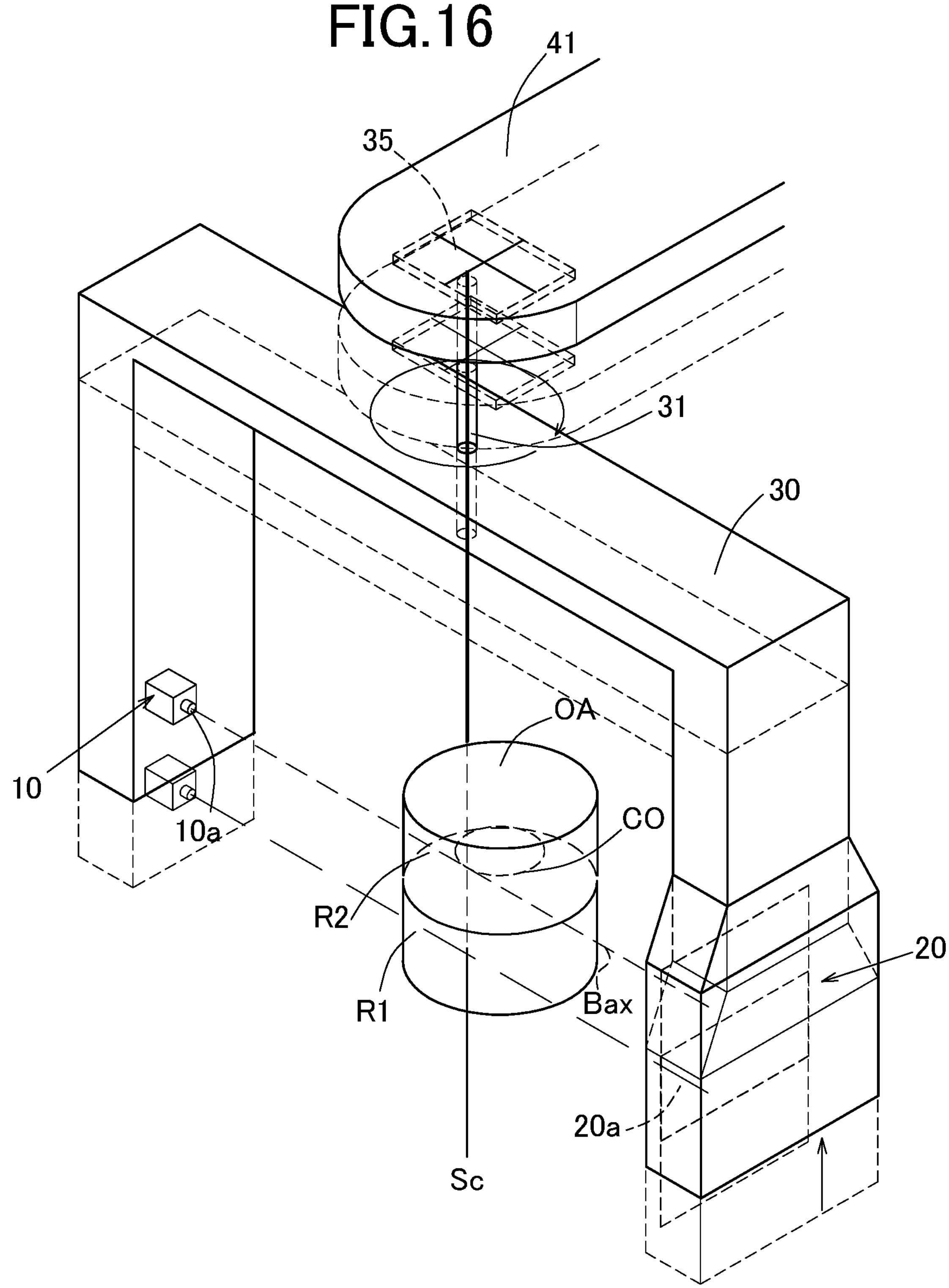
FIG. 16 illustrates movement of the X-ray generator and the X-ray detector to the imaging start position in imaging of a second imaging region.

FIG. 16 is a schematic perspective view showing the movement of the X-ray generator 10 and the X-ray detector 20 to the imaging start position Ps, at which the offset X-ray CT imaging of a second imaging region R2 is started. FIG. 17 shows the offset X-ray CT imaging of the second imaging region R2. FIG. 18 shows the joining of pieces of the CT imaging information I acquired as a result of the offset X-ray CT imaging of the first imaging region R1 and the second imaging region R2.

Figure 14A:
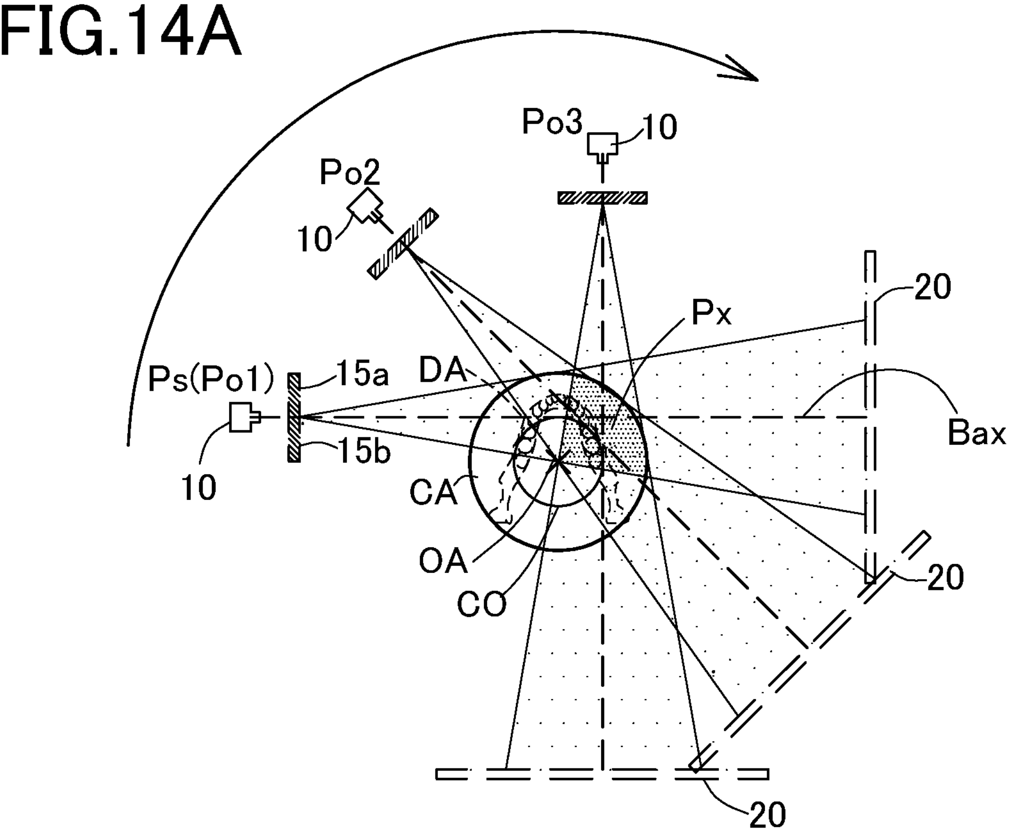
FIG. 14A and FIG. 14B illustrate offset X-ray CT imaging of the first imaging region.
Figure 14B:
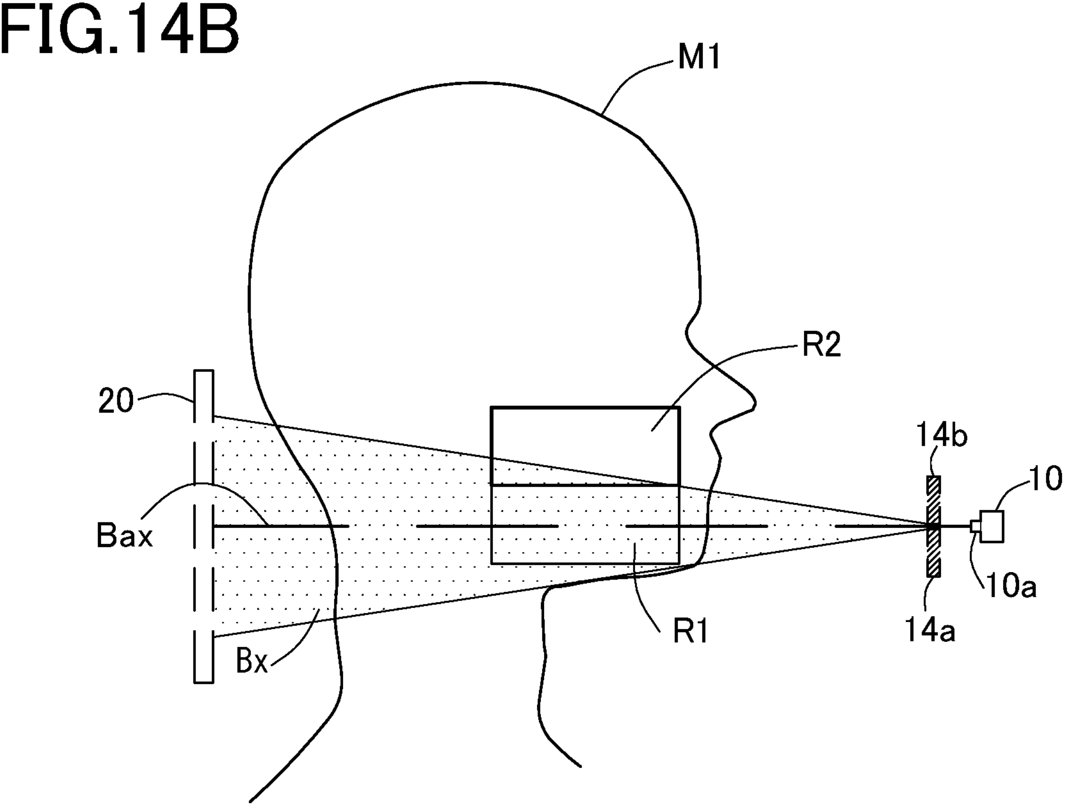
Figure 15A:
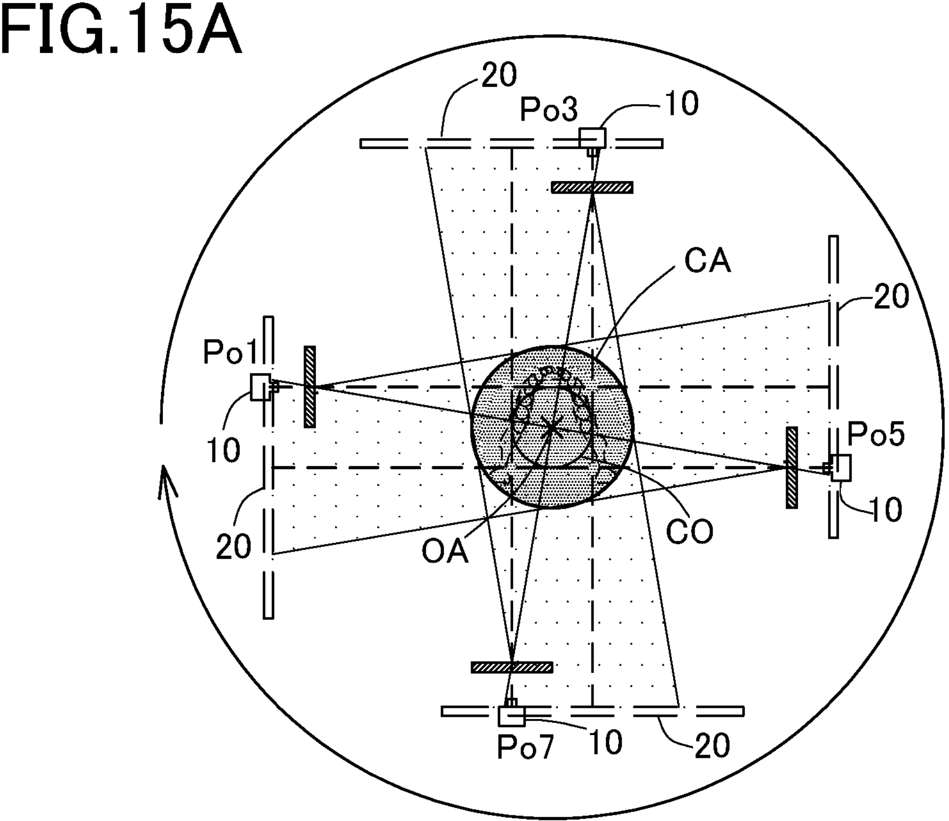
FIG. 15A and FIG. 15B illustrate the offset X-ray CT imaging of the first imaging region.
Figure 15B:
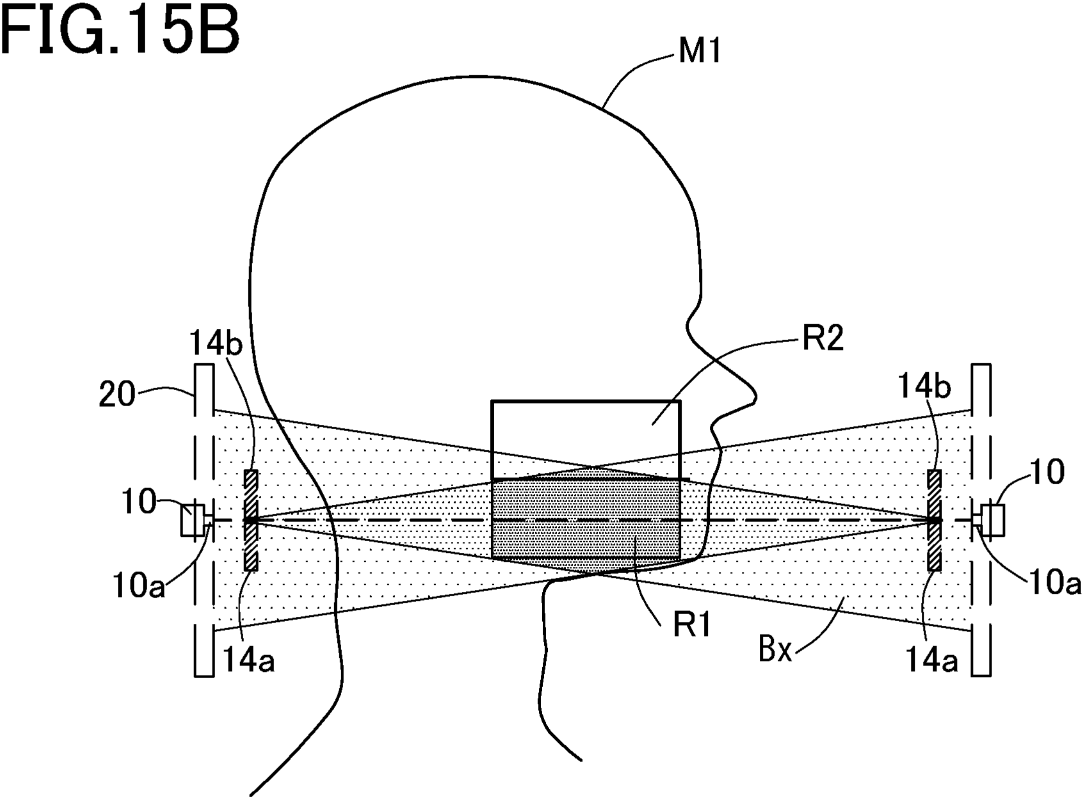

FIG. 14 and FIG. 15 will be described in more detail FIG. 14A and FIG. 15A are each a schematic plan view of the first imaging region R1 in the offset X-ray CT imaging. FIG. 14B and FIG. 15B are each a schematic side view of the first imaging region R1 in the offset X-ray CT imaging.

Figure 17A:
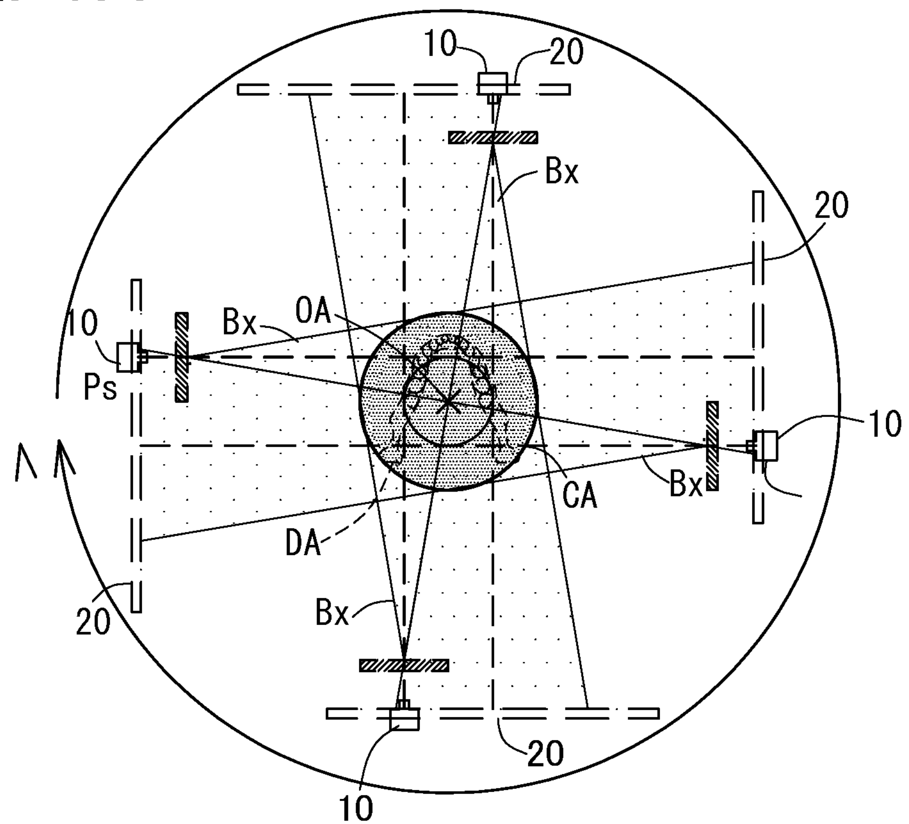
FIG. 17A and FIG. 17B illustrate the offset X-ray CT imaging of the second imaging region.
Figure 17B:
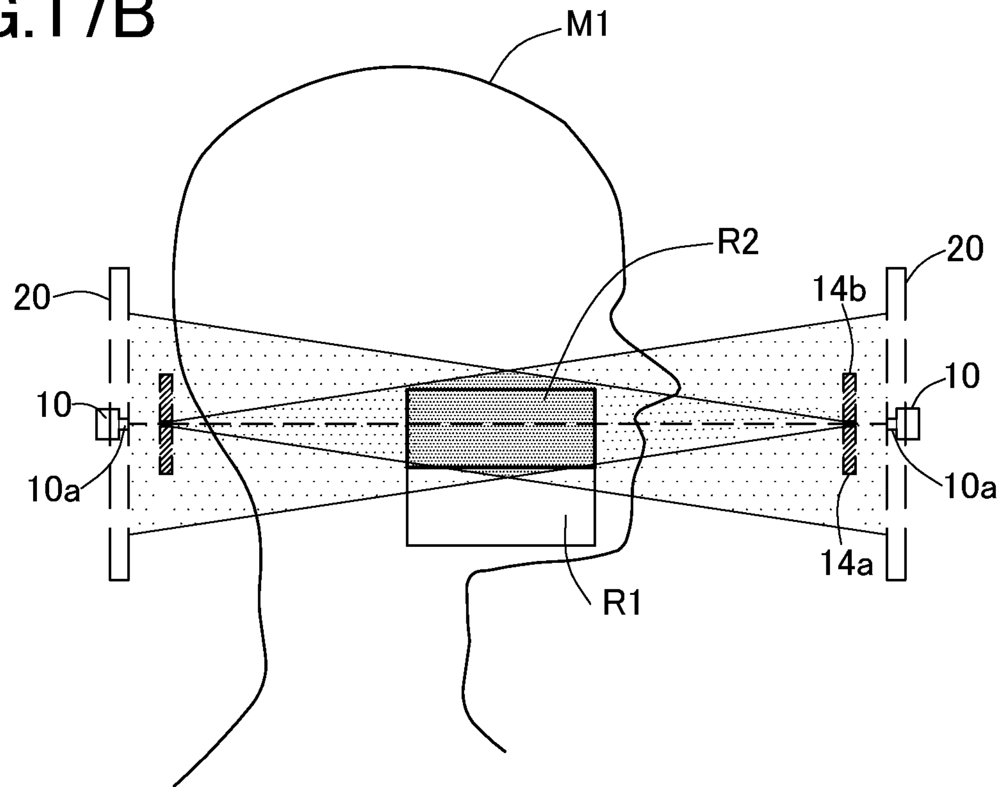

FIG. 17 will be described in detail FIG. 17A is a schematic plan view of the second imaging region R2 in the offset X-ray CT imaging. FIG. 17B is a schematic side view of the second imaging region R2 in the offset X-ray CT imaging.

In the following description, the entirety of a dental arch DA is the imaging target site of interest.

First, in order to perform the CT imaging, the subject M1 is secured to the main body 2 in the X-ray-preventive chamber 70 by use of the subject securing portion 423.

In this state, the operator presses a desired imaging mode on the imaging mode selection screen 61*a* displayed on the display 61, and thus the imaging mode setting reader 60*a* controls the receipt of the selected imaging mode and reads the imaging program of the selected imaging mode from the storage (step s1).

In the case where the imaging mode setting reader 60*a* receives the selection of the "stitch X-ray CT imaging" (step s2 Yes), the imaging condition setting screen 61*b* is displayed on the display 61, and the imaging conditions for the stitch X-ray CT imaging are allowed to be input (step s3).

In the case where a mode other than the "stitch X-ray CT imaging" is selected on the imaging mode selection screen 61*a* (step s2 No), imaging conditions suitable to the selected imaging mode are input, and the X-ray imaging is performed. The details wall not be described (step s14).

In the case where "panorama imaging capturing" is selected on the imaging mode selection screen 61*a*, the X-ray CT scanner 1 uses the main body controller 60 to control the X-ray irradiation range restrictor drivers 16, which drive and control the beam shaping mechanism 13, thus to adjust the interval between the facing edges 14*c* of the upper length direction blocking plate 14*a* and the lower length direction blocking plate 14*b* to be wider and to adjust the interval between the facing edges 15*c* of the left lateral direction blocking plate 15*a* and the right lateral direction blocking plate 15*b* to be narrower. In this manner, the opening 17 is made to have a rectangular shape longer in the length direction as seen in a front view for the panorama imaging. An X-ray thin beam expanding in a truncated pyramid shape longer in the length direction is directed toward the X-ray detector 20 to perform the panorama imaging.

Now, input of the imaging conditions in step s3 will be described in detail with reference to FIG. 11.

First, the operator inputs the number of times of imaging, by which the imaging is to be performed in the Z-axis direction, to the text box of the axial direction imaging number of times display 631 of the axial direction imaging region setting screen 600 displayed on the imaging condition setting screen 61*b*. Thus, the imaging mode setting reader 60*a* receives the number of times of imaging and executes the control of setting the number of times of imaging as an imaging condition (step t1). Specifically, "2" is input to the axial direction imaging number of times display 631, and thus the imaging mode setting reader 60*a* receives the number of times "2" of imaging and sets the number of times.

In this case, the imaging region to be processed by the X-ray CT imaging first is set as the first imaging region R1, and the imaging region to be processed by the imaging after the X-ray CT imaging of the first imaging region R1 is set as the second imaging region R2. The axial direction changing mechanism driving controller 60*c* controls the revolution arm 30 such that the revolution arm 30 moves upward after the X-ray CT imaging of the first imaging region R1 is finished.

Next, the axial direction imaging range LA along the axial direction is input to the imaging region setting display 632, and thus the imaging mode setting reader 60*a* controls the receipt of the axial direction imaging range LA along the axial direction, on which the stitch X-ray CT imaging is to be performed (step t2). After the other conditions displayed on the axial direction imaging region setting screen 600 are input, the Set button 641 is pressed to set, and thus the axial direction imaging range LA along the axial direction is set as an imaging condition.

Similarly, the moving distance by which the revolution arm 30 is to be moved upward after the imaging of the first imaging region R1 is input to the axial direction moving distance setter 633, and an overlapping region Rw of the first imaging region R1 and the second imaging region R2 is input to the overlapping amount setter 634. Thus, the imaging mode setting reader 60*a* receives the moving distance of the revolution arm 30 after the imaging of the first imaging region R1 and the overlapping amount of the first imaging region R1 and the second imaging region R2. The Set button 641 is pressed, and thus the respective values are set as imaging conditions and saved (step t3, step t4).

In the stitch CT imaging, nothing is input to the imaging region change setter 635. In this case, an axial direction imaging range L1 and an axial direction imaging range L2, which are respectively heights of the first imaging region R1 and the second imaging region R2, are set as values acquired by equally dividing the axial direction imaging range LA by two and adding the overlapping amount to the quotient.

Next, an operation of inputting the imaging conditions to the offset imaging setting screen 700 like in the case of the axial direction imaging region setting screen 600 will be described.

Specifically, "1" (corresponding to the first imaging region R1) or "2" (corresponding to the second imaging region R2) is input to the imaging number designator 731, and thus the imaging mode setting reader 60*a* receives the selection of the target of the imaging conditions to be now input (step t5) FIG. 7 shows a case where "1" is input to the imaging number designator 731, namely, a case where the imaging conditions for the planar direction of the first imaging region R1 are to be set.

Next, the imaging center OA of the imaging region CA, of the first imaging region R1, to be processed by the offset X-ray CT imaging is set (step t6), and the radius of the imaging region CA of the first imaging region R1 is set (step t7). Specifically, a desired position is selected as the imaging center OA by the pointer 710P on the image display 710. Thus the coordinates of the imaging center OA are displayed on the center display 732, and the imaging mode setting reader 60*a* controls the receipt of the selection of, and the setting of, the imaging center OA (step t6).

In the case where the imaging center OA is not selected, the center of the dental arch DA displayed on the dental arch image 711 may be set as the imaging center OA.

Next, the operator selects the imaging method for the first imaging region R11 (step t7) Specially, the operator presses "▼" displayed on the imaging method selection button 733 to display a pull-down menu, and selects either "Normal" corresponding to the normal X-ray CT imaging or "Offset" corresponding to the offset X-ray CT imaging from the pull-down menu as the X-ray CT imaging method for the first imaging region R1. Thus, the imaging mode setting reader 60*a* controls the receipt of the imaging method for the first imaging region R1.

In the case where, for example, "Offset" is selected step t7: Yes), the imaging mode setting reader 60*a* receives and sets the offset X-ray CT imaging as the imaging method for the imaging region R1. The imaging mode setting reader 60*a* also controls the receipt of the position of the imaging center OA and the position of the revolution center Sc (center of revolution about the axis of the revolution shaft 31 of the revolution arm 30), namely, the offset position, and sets the offset position as an imaging condition (step t8).

The operator uses the pointer 710P on the image display 710 to designate the CT imaging region line 714 for the selected and designated an imaging center OA. Thus, the receipt and the setting of the radius of the imaging region CA corresponding to the size of the desired CT imaging region are controlled (step t9).

In the case where the radius of the imaging region CA is not input, the initial value is automatically input as the radius.

As a result of performing the above-described steps, the imaging region CA to be processed by the X-ray CT imaging is displayed on the dental arch image 711, and an offset track CO along which the revolution center Sc is moved during the imaging is displayed on the image display 710 as a circular track centered around the imaging center OA (see FIG. 8).

Now, an example of quantifying the offset position will be described.

Figure 12B:
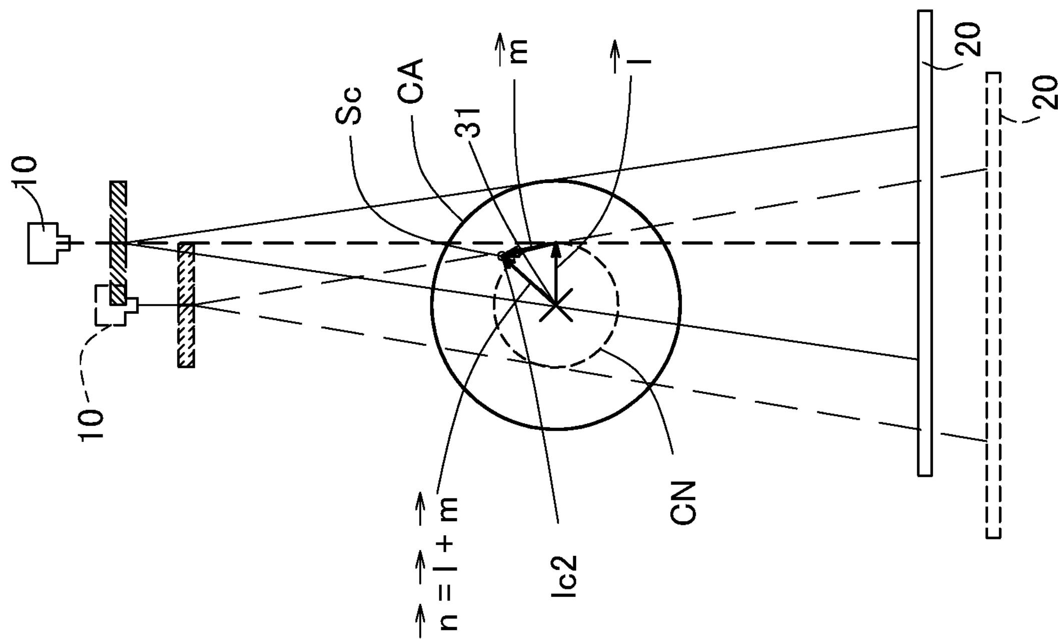
FIG. 12A and FIG. 12B illustrate quantification of an offset position.
Figure 12A:
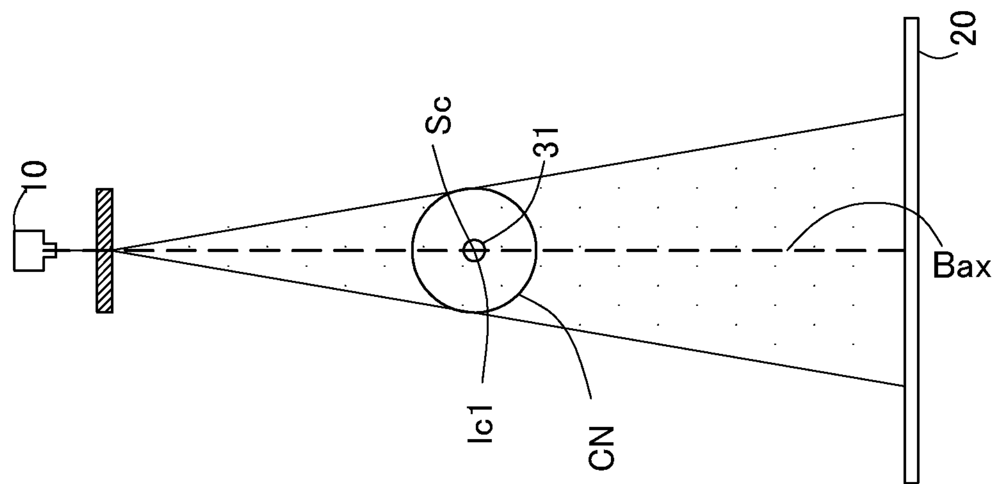

FIG. 12A shows the normal X-ray CT imaging, and FIG. 12B shows the offset X-ray CT imaging.

In FIG. 12A, the revolution shaft 31, more strictly, the revolution center Sc, is at a center position lc1 of a CT imaging region CN. In FIG. 12B, the imaging mechanism is offset from the state in FIG. 12A. In FIG. 12B, the position of the CT imaging region CA is the same as the center of the CT imaging region CN, but the revolution shaft 31, more strictly, the revolution center Sc, is moved to a point lc2 from the center position of the CT imaging region CA.

Considered in terms of vector components, the movement is synthesis vector 1+m, which is the sum of a component of vector l in the x-axis direction and vector m in the y-axis direction. l and m may be calculated as numerical values, and a coordinate operation may be performed.

The order of steps t6, t7 and t9 described above may be optionally changed. For example, after it is determined whether or not to select the offset X-ray CT imaging (step t7), the selection of the imaging center OA of the site of interest may be received (step t6).

As described above, the operator presses the Check button 746 after inputting and setting the imaging conditions for the first imaging region R1. Thus, the imaging conditions for the second imaging region R2 may be set in substantially the same procedure (step t10: Yes).

In the following description, the offset X-ray CT imaging of the second imaging region R2 is performed under the same conditions as those for the first imaging region R1. Alternatively, as described below, the imaging center OA may be set at different positions or with different radii for the first imaging region R1 and for the second imaging region R2. In such a case, the coordinates of the imaging centers OA respectively suitable to the first imaging region R1 and the second imaging region R2 are set.

After the imaging conditions for R1 and R2 are set, the operator presses the NEXT button 745. Thus, the imaging mode setting reader 60*a* determines whether the stitch imaging is possible or not based on the imaging conditions received and set (step s4).

This determination may be, for example, a determination made based on position information detection performed by the position detector 18 under the control of the position detector controller 60*j*, or a determination on whether the imaging range is appropriate or not under the control of the high sensitivity site determiner 60*m*. Specifically, it is now assumed that the K-ray generator 10 and the X-ray detector 20 moved under the control of the revolution table driving controller 60*b* and the axial direction chancing mechanism driving controller 60*c* are determined as colliding against the subject 111 based on the position information detection performed by the position detector controller 60*j* (step s4: No). In this case, a notification operation such that, for example, the notifier 90 makes a predetermined buzzer sound under the control of the notifier controller 60*k* is executed (step s15), and the revolution table driving controller 60*b* and the axial direction changing mechanism driving controller 60*c* control the revolution arm 30 to stop moving. The imaging mode setting reader 60*a* performs control such that the imaging conditions are adjusted again (step s3).

By contrast, in the case where the stitch imaging is determined to be possible (step s4: Yes), a notification operation of notifying that the stitch imaging is possible is made under the control of the notifier controller 60*k*. When the operator presses the imaging driving switch 65*b* upon receipt of the notification operation, the revolution table driving controller 60*b*, the axial direction changing mechanism driving controller 60*c* and the revolution arm position controller 60*d* control the revolution arm 30 such that the revolution arm 30 is moved to the imaging start position Ps for the first imaging region R1 (step s5 and step s6).

This will be described in more detail. As shown in FIG. 13 and FIG. 14, the revolution table driving controller 60*b* controls the XY table 35 to translate the revolution arm 30 in the horizontal direction such that the revolution shaft 31 (revolution center Sc) of the revolution arm 30 matches the imaging center OA (step s5). In addition, under the control of the axial direction changing mechanism driving controller 60*c* and the revolution arm position controller 60*d*, the position adjustment, in the Z-axis direction, of the X-ray generator 10 and the X-ray detector 20 is performed such that an irradiation direction dl of the X-ray cone beam Bx directed from the X-ray emitter 10*a* passes the center, in the Z-axis direction, of the first imaging region R1 (step s6).

In the example shown in FIG. 13 and FIG. 14, the revolution arm position controller 60*d* controls the revolution arm driver 30K to revolve the revolution arm 30 for position adjustment such that the X-ray generator 10 is located to the left of the subject M1 at the imaging start position Ps.

The X-ray cone beam Bx irradiates the imaging center OA set on the dental arch image 711, and an irradiation central axis Bax of the X-ray cone beam Bx passes a position eccentric from the imaging center OA.

As shown in FIG. 14 and FIG. 15, in synchronization of the revolution of the revolution arm 30 located in this manner about the axis of the revolution shaft 31, the revolution center Sc (revolution center about the axis of the revolution shaft 31 of the revolution arm 30) revolves about the imaging center OA as the rotation center. Thus, the X-ray generator 10 directing the X-ray cone beam Bx from the X-ray emitter 10*a* and the X-ray detector 20 detecting the X-ray cone beam Bx revolve around the subject M1. In this case, a track of the X-ray, in X-ray cone beam Bx, passing the central axis of the revolution center Sc is a tangent in contact with the circular track of the revolution center Sc. In this manner, the X-ray CT imaging may be performed on the entirety of the first imaging region R1 as a region of interest.

This will be described in more detail. As shown in FIG. 14, the revolution center Sc is rotated clockwise so as to draw a true circle, with the imaging center OA, which is the rotation center, being the revolution center. The revolution arm 30 is rotated about the revolution center Sc. Thus, the X-ray generator 10 moves while revolving clockwise from Po1, corresponding to the imaging start position Ps, to Po2 to Po3.

At this point, along with the revolution of the X-ray generator 10 along an outer circumference of the subject M1 from Po2 to Po3 about the revolution center Sc, as the revolution center, which rotates with respect to the imaging center OA, the X-ray cone beam Bx directed from the X-ray emitter 10*a* is directed toward a left top portion (range Px in the figure) of the subject M1 (dental arch DA) as overlapping a region irradiated in a different direction.

The X-ray generator 10 is further revolved from Po3 to Po5 to Po7 to Po1; namely, the X-ray generator 10 is rotated at 360 degrees with respect to the subject M1 (step s7). Thus, the X-ray cone beam Bx may be directed toward the entirety of the region of interest, and the first imaging region R1 may be entirely processed by the imaging (see FIG. 15A and FIG. 15B). From the projection data on the first imaging region R1 acquired in this manner, three-dimensional image data on the first imaging region R1 may be constructed.

Next, with reference to FIG. 16 and FIG. 17, the offset X-ray CT imaging of the second imaging region R2 will be described.

After the offset X-ray CT imaging of the first imaging region R1 is finished, the revolution table driving controller 60*b*, the axial direction changing mechanism driving controller 60*c* and the revolution arm position controller 60*d* respectively control the revolution arm driver 30K, the XY table 35 and the axial direction changing mechanism 43 to move the revolution arm 30 such that the X-ray generator 10 and the X-ray detector 20 are located at the imaging start position Ps for the second imaging region P2 (step s8 and step s9).

In synchronization with the upward movement of the revolution arm 30 after the X-ray CT imaging of the first imaging region R1 is finished, the subject holder 42H is driven by the subject holder elevator 44 to move down with respect to the upper frame 41. Therefore, the subject securing portion 423 may maintain the relative height thereof at a certain position, and may change the height of the revolution aunt 30 while keeping the head MH still in the height direction. In this manner, the lower frame 42 is moved in a direction opposite to the direction of the movement of the upper frame 41, and thus the position of the head MH is kept at a certain position relatively.

This will be described in more detail. In order to perform the X-ray CT imaging of the second imaging region R2, the XY table 35 is controlled such that in synchronization with the revolution of the revolution arm 30 about the axis of the revolution shaft 31, the revolution arm 30 is translated to a position at which the revolution center Sc of the revolution arm 30 matches the imaging center OA of the second imaging region R2 (step s8). In addition, the X-ray generator 10 and the X-ray detector 20 are moved upward by the value set by the axial direction moving distance setter 633 while rotating counterclockwise at 360 degrees (step s9). Thus, the revolution arm 30 may be moved to the ranging start position Ps for the second imaging region R2. In other words, the X-ray generator 10 and the X-ray detector 20 is moved while drawing an upward spiral track and is located at the imaging start position Ps for the second imaging region P2 (see FIG. 16).

Like in the case of the first imaging region R1, the revolution arm 30 is rotated while moving with respect to the imaging center OA such that the revolution shaft 31 is revolved at 360 degrees about the imaging center OA. Thus, the X-ray generator 10 and the X-ray detector 20 revolve around the subject M1 while the X-ray generator 10 directs the X-ray cone beam Bx from the X-ray emitter 10*a*. In this manner, like in the case of the first imaging region R1, the offset X-ray CT imaging may be performed on the entirety of the second imaging region R2 as a region of Interest (see FIG. 17A and FIG. 17B).

In the case where another imaging region is set (step s11: Yes), the revolution arm 30 is moved to the imaging start position Ps for the imaging region to be processed by the imaging (step s7), and the imaging is performed in substantially the same manner (step s7 through step s10). In the case where no other imaging region is set (step s11: No), the stitch X-ray CT imaging is finished, and the procedure advances to the process of generating the CT imaging information I (step s12).

As described above, the projection data (volume data) on the first imaging region R1 and the second imaging region R2 processed by the offset X-ray CT imaging may be stored on the storage 64 and may be read into the information processing device 8 via the communication I/F 63 and the communication I/F 87. Based on the projection data on the first imaging region R1 and the second imaging region R2 read into the information processing device 8, the CT imaging information generator 861*a* executes a process of the CT imaging information I. Thus, first CT imaging information I1 and second CT imaging information I2, which are offset CT imaging information 10 corresponding, to the first imaging region R1 and the second imaging region R2, are generated (step s12). The first CT imaging information I1 and the second CT imaging information I2 are stored on the X-ray imaging information storage 851.

Figure 18A:
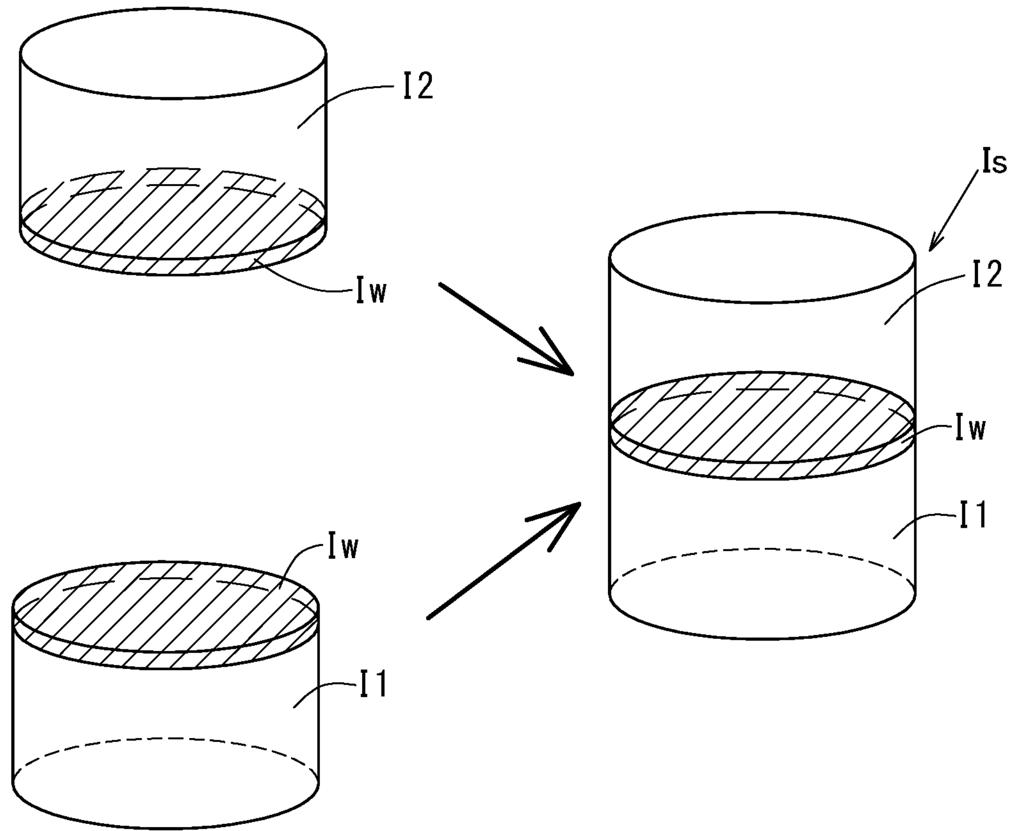
FIG. 18A and FIG. 18B illustrate joining of offset CT imaging information.

As shown in FIG. 18A, a stitch process of joining the first CT imaging information I1 and the second CT imaging information I2 the axial direction is executed by the stitch image information generator 861*b*. Thus, stitch imaging information Is corresponding to the imaging region CA may be generated, and three-dimensional data corresponding to the imaging region CA may be reconstructed based on the stitch imaging information Is by the stitch image constructor 862*b* (step s13).

As set by the overlapping amount setter 634, the first imaging region R1 and the second imaging region R2 include the overlapping region RW, in which parts thereof overlap each other, in the axial direction during the offset X-ray CT imaging. Therefore, the first CT imaging information I1 and the second CT imaging information I2, based on which the stitch imaging information Is is generated, include overlapping image information IwIw, in which parts thereof overlapping each other. Based on a characteristic portion of the overlapping image information Iw, the first. CT imaging information I1 and the second CT imaging information I2 are joined with each other. Thus, highly, precise stitch imaging information Is may be generated (see FIG. 18A).

In order to set the imaging conditions for the first imaging region R1 and the second imaging region R2, the overlapping amount of the first imaging region R1 and the second imaging region R2 and the moving distance of the revolution arm elevator 40 in the axial direction may be set by the axial direction moving distance setter 633 and the overlapping amount setter 634. Therefore, the process of generating the stitch imaging information Is may be executed based on these values. Therefore, the load on the process may be alleviated, and highly precise stitch imaging information Is may be generated.

Figure 18B:
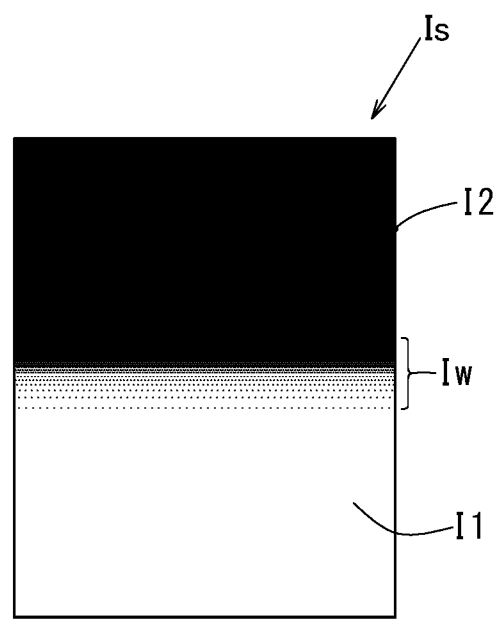

In addition, as shown in FIG. 18B, in order to execute a process of joining the first CT imaging information I1 and the second CT imaging information I2, the overlapping image information Iw is weighted. Thus, stitch imaging information Is that does not clearly show the border between the first CT imaging information I1 and the second CT imaging information I2 may be generated.

Specifically, as shown in FIG. 18B, in order to execute the averaging process of the overlapping image information Iw, data on the first CT imaging information I1 side of the overlapping image information Iw is multiplied by a high coefficient to calculate the average value. As the second CT imaging information 12 is becoming closer, the coefficient to be multiplied by the data on the first CT imaging information I1 side is decreased, whereas the coefficient to be multiplied by the data on the second CT imaging information I2 side is increased. In this manner, stitch imaging information Is that does not clearly show the border between the first CT imaging information I1 and the second CT imaging information I2 overlapping each other at the image information Iw may be generated. The stitch image Gs reconstructed based on the stitch imaging information Is is natural three-dimensional data that does not clearly show the border between the first imaging region R1 and the second imaging region R2.

Figure 19:
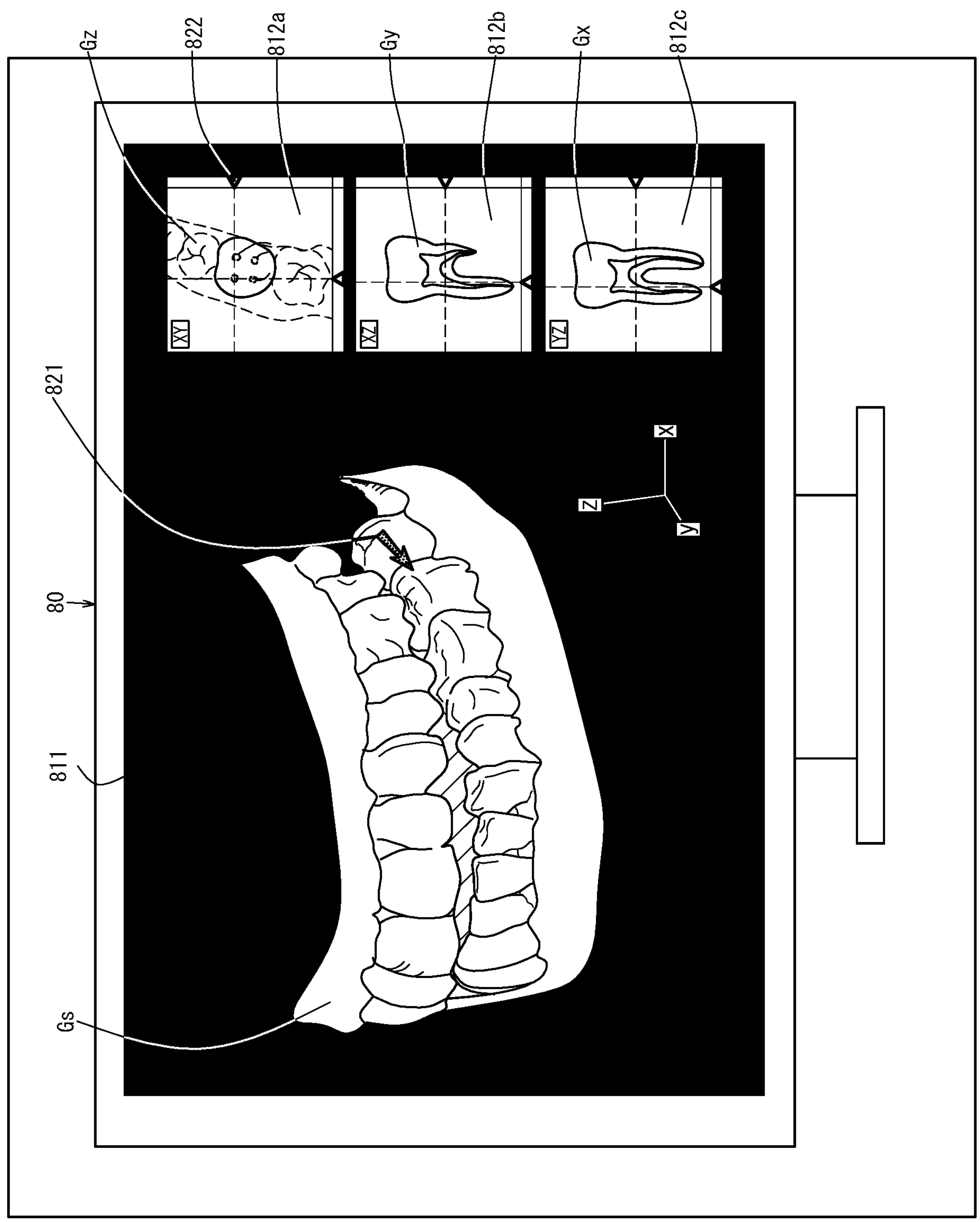
FIG. 19 illustrates a display.
Figure 20:
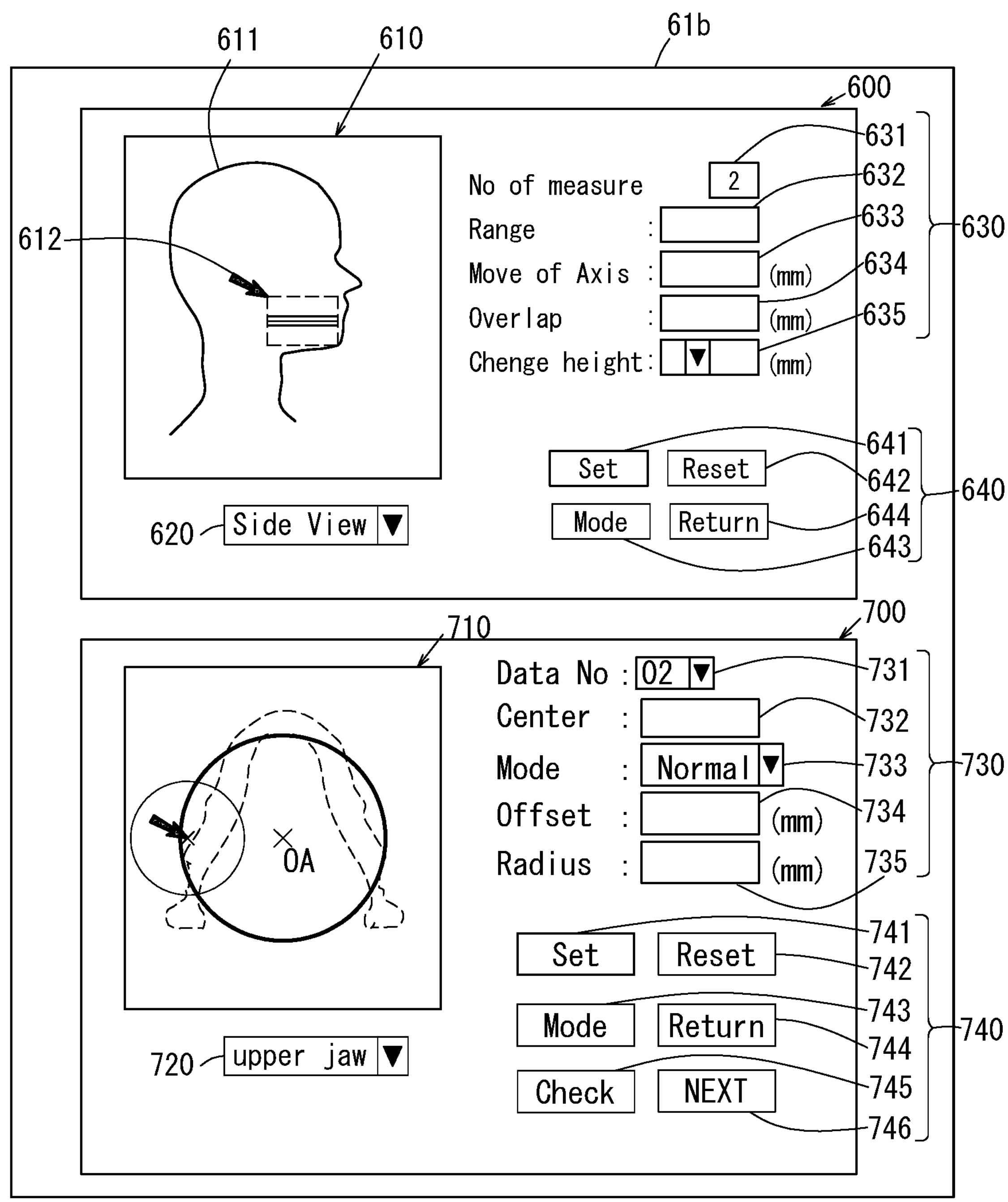
FIG. 20 illustrates the operation panel, by which the X-ray CT imaging under different imaging conditions is set.
Figure 21:
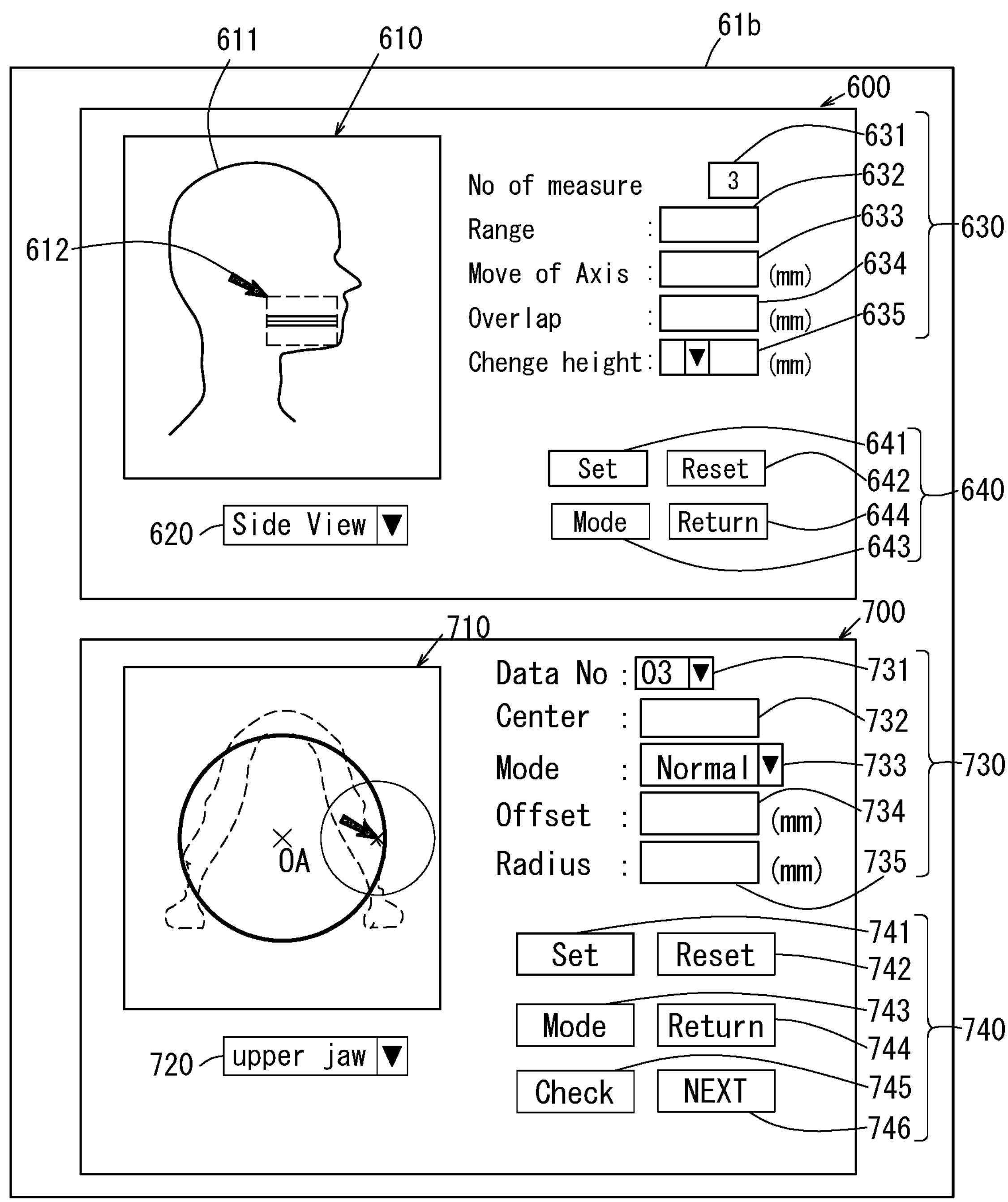
FIG. 21 illustrates the operation panel, by which the X-ray CT imaging under different imaging conditions is set.

As shown in FIG. 19, the display 81 displaying the stitch image Gs thus reconstructed includes a main display 811 displaying the stitch image Gs and a cross-section display 812 showing a cross-section image Gc of a designated specific tooth, region or the like.

In this embodiment, the cross-section display 812 is displayed to the right of the main display 811. The cross-section display 812 does not need to have such a structure. For example, the cross-section display 812 may be displayed to the left of, above, or below, the main display 811. The position of the cross-section display 812 may be arbitrarily changeable.

A pointer 821 acting as the operation portion 82 and an XYZ coordinate system for the stitch image Gs are displayed on the main display 811 in addition to the stitch image Gs.

The cross-section display 812 includes an KY cross-section display 812*a* displaying an KY cross-section image Gz of a designated tooth, region or the like, an XZ cross-section display 812*b* displaying an KZ cross-section image Gy, and a YZ cross-section display 812*c* displaying a VZ cross-section image Gx. To the right of, and below, each of the cross-section displays, an axial coordinate is displayed. In the axial coordinate, a cursor 822 showing the coordinate position in the displayed cross-section image Gc is provided.

The cursor 822 acting as an operation portion is movable in the axial coordinate on the cross-section display 812. The cursor 822 is moved on the cross-section display 812, so that the cross-section image Gc at a designated position may be displayed on the XY cross-section display 812*a* though the YZ cross-section display 812*c*.

The stitch image Gs is displayed on the main display 811. Alternatively, a tooth image G1 and a tooth image G2 reconstructed based on the first CT imaging information I1 and the second CT imaging information I2 may be displayed independently or side by side. Still alternatively, a cross-sectional CT image showing a designated surface may be displayed.

As described above, in order to perform the imaging of the second imaging region R2 after the imaging of the first imaging region R1, the X-ray CT scanner 1 capable of performing the stitch X-ray CT imaging returns the X-ray generator 10 and the X-ray detector 20 to the initial positions as seen in a plan view and translates the X-ray generator 10 and the X-ray detector 20 in the Z-axis direction. With such a structure, for example, the load imposed on an electric wire or the like provided on the revolution shaft 31 may be alleviated, and the first imaging region R1 and the second imaging region R2 may be processed by the imaging in the same direction. Thus, the precision of generating the stitch imaging information Is by joining pieces of the CT imaging information with each other may be improved.

Alternatively, in order to perform the imaging of the second imaging region R2 after the imaging of the first imaging region R1 the revolution arm elevator 40 may be translated in the axial direction without returning the X-ray generator 10 and the X-ray detector 20 to the initial position as seen in a plan view, and the X-ray generator 10 and the X-ray detector 20 may be rotated clockwise about the revolution center Sc as the rotation axis. In other words, in order to perform the imaging of the first imaging region R1 and the second imaging region R2, the X-ray generator 10 and the X-ray detector 20 may be rotated at 720 degrees as seen in a plan view. With such a structure, the imaging time may be shortened, and the load on the subject M1 may be alleviated.

Still alternatively, after the imaging of the first imaging region R1, the revolution arm elevator 40 may be translated in the axial direction, and the X-ray generator 10 and the X-ray detector 20 may be rotated counterclockwise about the revolution center Sc as the rotation axis. Namely, the imaging direction of the first imaging region R1 and the imaging direction of the second imaging region R2 may be opposite to each other. With such a structure, the imaging time may be shortened, and the load on the subject M1 may be alleviated.

Now, with reference to FIG. 20 through FIG. 23, a method for the stitch X-ray CT imaging will be briefly described. With the method for the stitch X-ray CT imaging, the offset X-ray CT imaging and the normal X-ray CT imaging are performed continuously, and the offset CT imaging information Io and normal imaging information In thus generated are joined with each other.

First, the stitch X-ray CT imaging is selected on the imaging mode selection screen 61*a*, and "3" is input to the axial direction imaging number of times display 631 on the imaging condition setting screen 61*b*. Appropriate numerical values are input to the imaging region setting display 632, the axial direction moving distance setter 633 and the overlapping amount setter 634 (see FIG. 20).

Thus, the imaging mode setting reader 60*a* reads a program of the stitch X-ray CT imaging from the storage 64, and controls the receipt and the setting of the imaging conditions (step t1 through step t4). As a result, the imaging region is divided into three regions, namely, a first imaging region R1*a*, a second imaging region R2*a* and a third imaging region R3*a*.

Next, "1" is selected (not shown) by the imaging number designator 731 on the offset imaging setting screen 700, and thus the imaging conditions for the first imaging region R1*a* are set (step t5 through step t9). The imaging conditions for the first imaging region R1*a* are the same as the imaging conditions for the first imaging region R1 in the offset X-ray CT imaging described above, and therefore will not be described in detail.

Next, after the imaging conditions for the first imaging region R1*a* are input, the operator presses the Check button 746 or selects "2" by the imaging number designator 731. Thus, the imaging conditions for the planar direction of the second imaging region R2*a* are set (step t5).

A normal imaging center On for the normal X-ray CT imaging of the second imaging region R2*a* starts to be received. A desired position on the dental arch image 711 is selected by the designation cursor 612. Thus, the imaging mode setting reader 60*a* receives and sets the normal imaging center On2 of the second imaging region R2*a* (step t6). The normal imaging center On2 of the second imaging region R2*a* is on the left deep side of the upper jaw.

"▼" displayed on the imaging method selection button 733 is pressed, and thus "Normal" corresponding to the normal X-ray CT imaging is selected from the pull-down menu as the method for the X-ray CT imaging of the second imaging region R2*a*. In this manner, the imaging mode setting reader 60*a* receives and sets the imaging method for the second imaging region R2*a* (step t7: No).

The radius designator 735 is pressed and a point is designated, such that the point includes a target site, on the normal imaging center On2 by the designation cursor 612 on the image display 710. Thus, the imaging mode setting reader 60*a* receives and sets the distance from the normal imaging center On2 to the designated point as the radius of the imaging region CA (step t9).

Next, the imaging conditions for the third imaging region R3*a* are set in substantially the same procedure as for the second imaging region R2*a*. The third imaging region R3 is processed by the normal X-ray CT imaging like the second imaging region R2. A normal imaging center On3 of the third imaging region R1*a* is on the right deep side of the upper jaw. The radii of the second imaging region R2*a* and the third imaging region R3*a* calculated and set by the radius designator 735 are set such that the second imaging region R2 and the third imaging region R3 do not overlap each other.

The imaging conditions for the first imaging region R1*a*, the second imaging region R2*a* and the third imaging region R3*a* are input in this manner (step s3), and it is checked whether the stitch X-ray CT imaging is possible or not (step s). After this, the operator presses the imaging driving switch 65*b*. Thus, the revolution arm 30 is controlled by the revolution table driving controller 60*b* and axial direction changing mechanism driving controller 60*c* to move such that the X-ray detector 20 and the revolution arm 30 are located at the imaging start position Ps. Thus, the offset X-ray CT imaging of the first imaging region. R1*a* is performed.

After the offset X-ray CT imaging of the first imaging region R1*a* is performed, the normal X-ray CT imaging of the second imaging region R2*a* and the normal X-ray CT imaging of the third imaging region R3*a* are performed continuously (step s6 through step s11).

Now, the normal X-ray CT imaging of the second imaging region R2*a* will be described briefly with reference to FIG. 22.

Figure 22A:
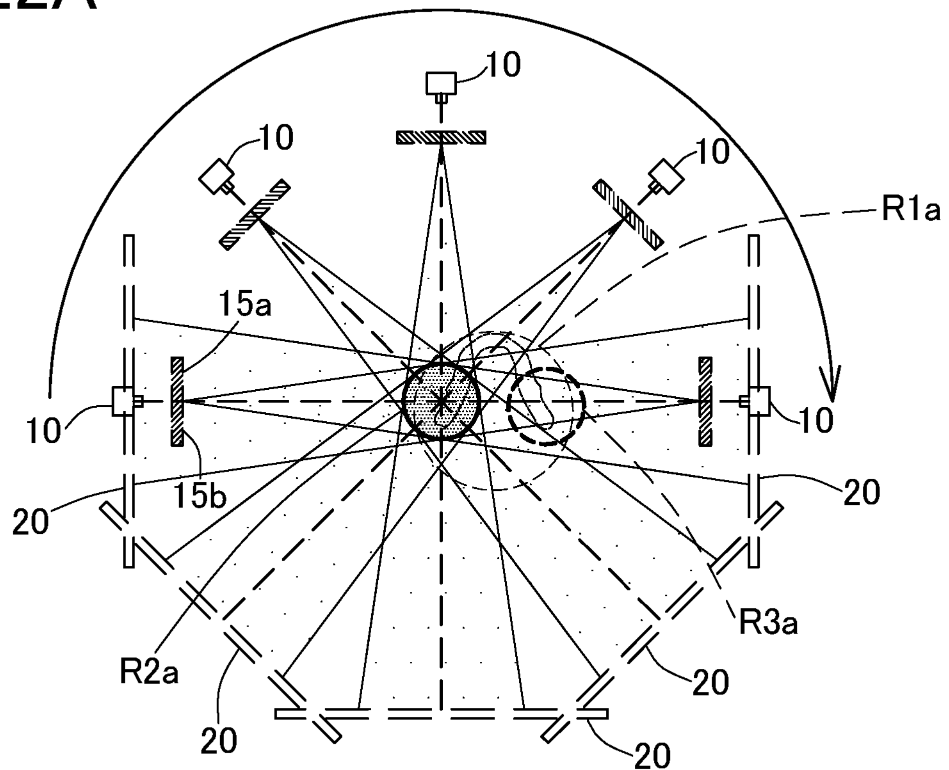
FIG. 22A and FIG. 22B illustrate normal X-ray CT imaging.

FIG. 22A illustrates the normal X-ray CT imaging of the second imaging region R2*a*, but also shows the first imaging region R1*a* and the third imaging region R3*a* in order to clarify the positional relationship among the imaging regions.

After the offset X-ray CT imaging of the first imaging region R1*a* is performed, the revolution table driving controller 60*b* and the axial direction changing mechanism driving controller 60*c* respectively control the revolution shaft 31 and the axial direction changing mechanism 43 to realize the following. The revolution arm 30 is moved such that the revolution center Sc of the X-ray generator 10 and the X-ray detector 20 matches the normal imaging center On and such that the height of the X-ray generator 10 and the X-ray detector 20 is the center, in the Z-axis direction, of the second imaging region R2*a*; and in addition, the revolution arm 30 is revolved such that the X-ray generator 10 is located to the left of the subject M1 facing the support column 50, and thus is located at the imaging start position Ps for the second imaging region R2*a* (step s8 and step s9).

While the X-ray cone beam Bx is directed from the X-ray emitter 10*a*, the revolution arm 30 is revolved at 180 degrees about the revolution center Sc (normal imaging center On). Thus, the normal X-ray CT imaging of the second imaging region R2*a* is performed, and the projection data (volume data) on the second imaging region R2*a* is collected.

After the normal X-ray CT imaging of the second imaging region R2*a* is performed, the normal X-ray CT imaging of the third imaging region R3*a* is performed in substantially the same manner.

In this case, the revolution center Sc of the revolution arm 30 does not need to be translated with respect to the imaging center OA during the normal X-ray CT imaging. Therefore, the entirety of the second imaging region R2*a* may be processed by the X-ray CT imaging merely by revolving the revolution arm 30 at 180 degrees (see FIG. 22A).

As described above, the normal imaging centers On of the second imaging region R2*a* and the third imaging region R3*a* are made offset from the imaging center O of the first imaging region R1*a*, and the normal X-ray CT imaging of the second imaging region R2*a* is performed. Thus, the X-ray CT imaging is performed with the high sensitivity site H such as an eyeball or the like being avoided, and the projection data (volume data) may be collected.

Figure 22B:
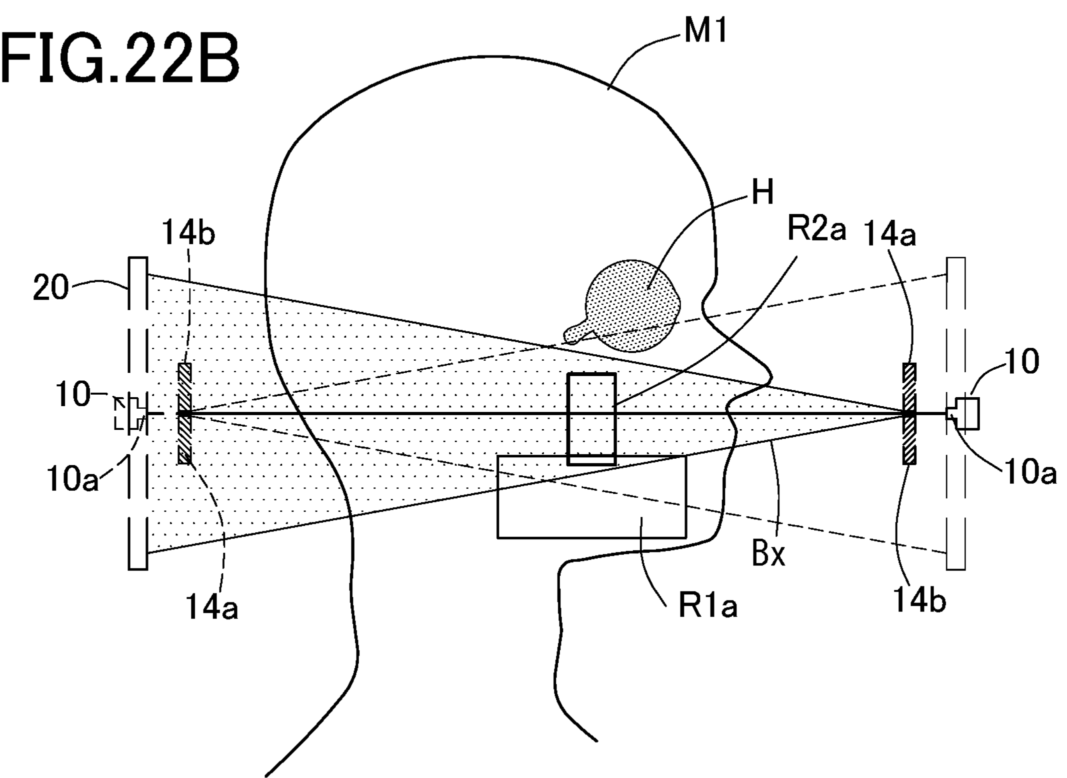

This will be described in more detail. In the case where as shown in FIG. 22B, the X-ray generator 10 is located to the rear of the subject M1, a part of the X-ray cone beam Bx directed from the X-ray emitter 10*a* irradiates the high sensitivity site H. In the case where the X-ray generator 10 is located at a position facing the subject M1, the X-ray cone beam Bx directed from the X-ray emitter 10*a* may be prevented from irradiating the high sensitivity site H.

As described above, the irradiation direction may be limited by performing the normal X-ray CT imaging of the second imaging region R2*a* and the third imaging region R3*a*. Therefore, while the X-ray CT imaging is performed on a wide range including the tooth of interest with the X-ray detector 20 including the small X-ray detection surface 20*a*, the X-ray CT imaging may be performed on the tooth of interest with the high sensitivity site H being avoided.

After the normal X-ray CT imaging of the third imaging region R3*a* is finished, the X-ray imaging information generator 861 processes the projection data (volume data) on the first imaging region R1*a*, the second imaging region R2*a* and the third imaging region R3*a* to generate first CT imaging information I1*a*, second CT imaging information I2*a* and third CT imaging information I3*a*. The image constructor 862 processes the first CT imaging information I1*a*, the second CT imaging information I2*a* and the third CT imaging information I3*a*, and thus stitch imaging information Isa on the entirety of the region of interest is generated (see FIG. 23).

Figure 24:
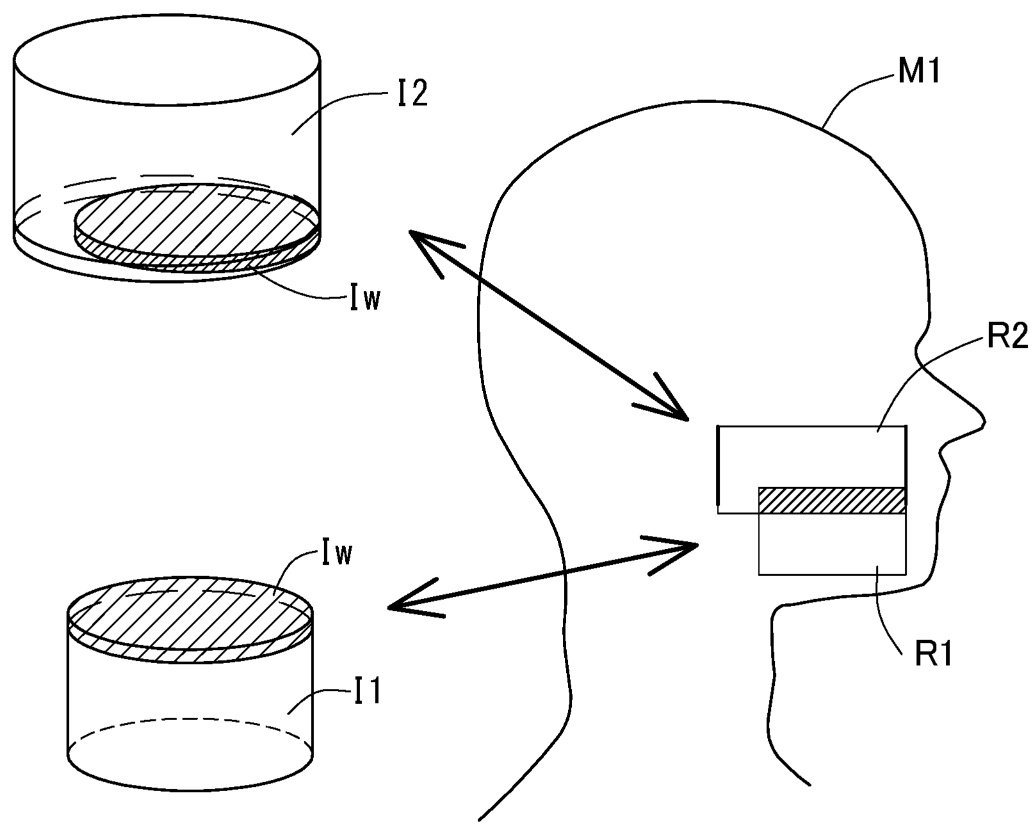
FIG. 24 illustrates another stitch X-ray imaging.

Instead of the above-described example, as shown in FIG. 24, the radius of the second imaging region R2 may be made longer than the radius of the first imaging region R1 for the offset X-ray CT imaging. For example, in the case where the radius of the second imaging region R2 corresponding to the upper jaw is made longer, the offset X-ray CT imaging may be performed on the upper jaw including the jaw joint, and offset VTX-ray imaging may be performed on the lower jaw, the jaw joint of which is included in the first imaging region R1. The stitch imaging information Is is generated based on the first CT imaging information I1 and the second CT imaging information I2 on the first imaging region R1 and the second imaging region R2, and thus the CT image of the entirety of the jaw including the jaw joint may be acquired.

Figure 25:
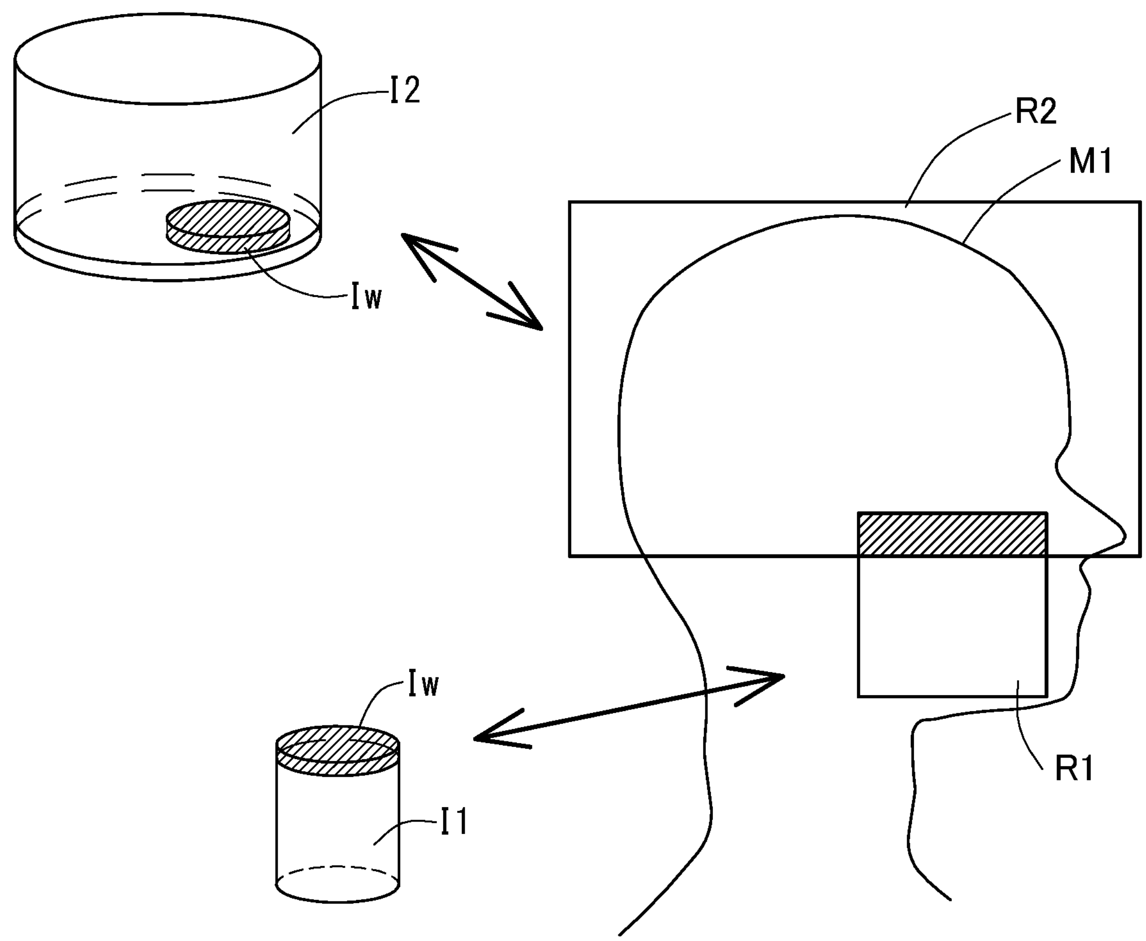
FIG. 25 illustrates another stitch X-ray imaging.

As shown in FIG. 25, the first imaging region R1 may be set to the entirety of the jaw including the tip of the nose, and the second imaging region R2 may be set to a region above the camper's plane. In this state, the offset X-ray CT imaging is performed on the first imaging region R1 and the second imaging region R2. Thus, the stitch imaging information Is on the entirety of the jaw and the skull may be generated, and the CT image of the entirety of the jaw including the skull may be acquired. In this manner, diagnosis on the reference point may be performed to acquire a cephalogram.

With the X-ray CT scanner 1 described above, the height and the positions of the X-ray generator 10 and the x-ray detector 20 are changed to perform the stitch X-ray CT imaging. Alternatively, for example, the stitch X-ray CT imaging may be performed by changing the irradiation direction of the X-ray cone beam Bx without changing the position of the revolution arm 30.

Figure 26:
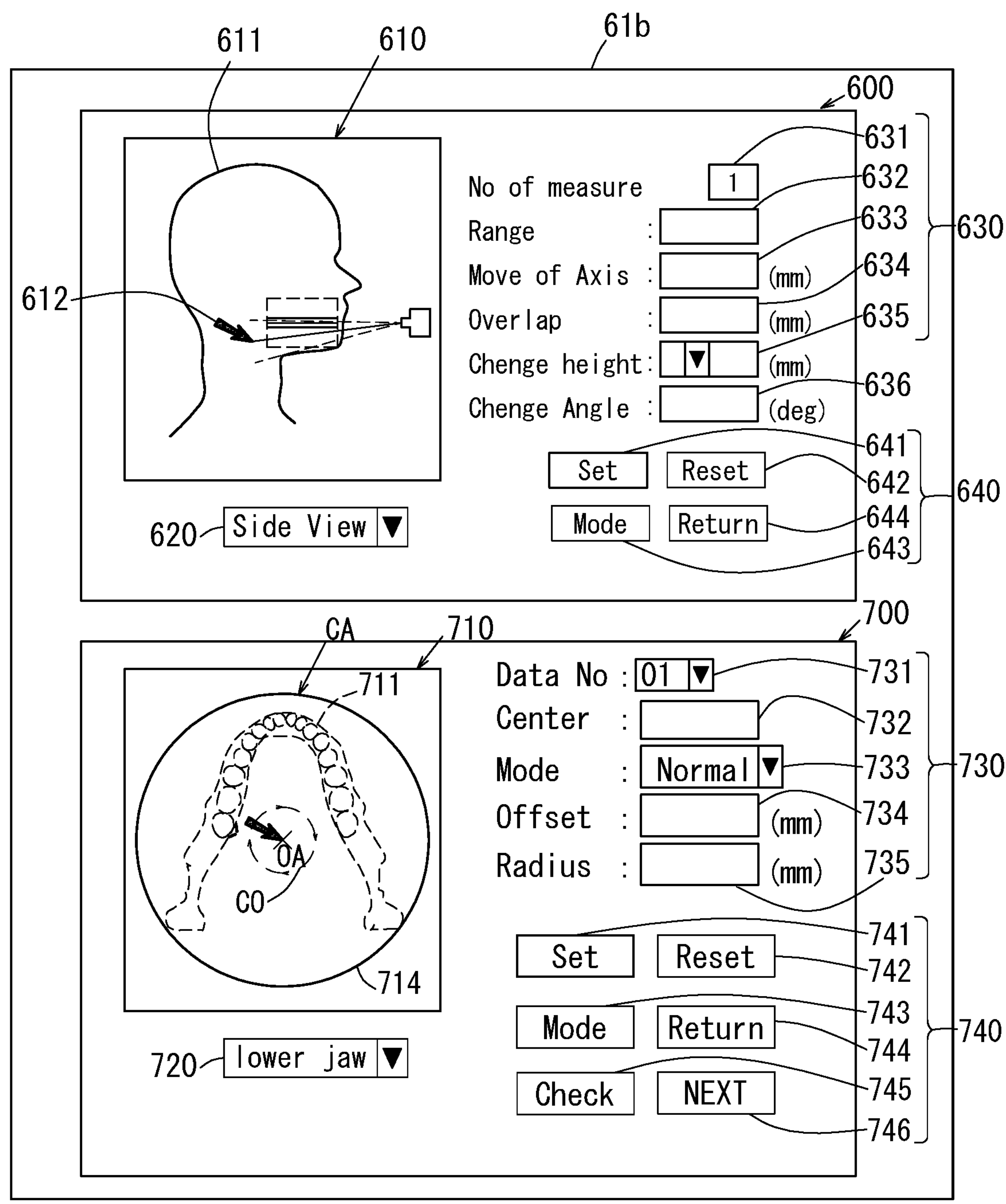
FIG. 26 illustrates the operation panel, by which an irradiation direction of an X-ray cone beam is set.

Hereinafter, with reference to FIG. 26 through FIG. 28, an X-ray CT scanner 1 performing the stitch X-ray CT imaging by changing the irradiation direction of the X-ray cone beam Bx will be described.

Components that are substantially the same as those of the X-ray CT scanner 1 will bear the identical reference signs thereto, and descriptions thereof will be omitted.

The basic structure of the X-ray CT scanner 1*a* is substantially the same as that of the X-ray CT scanner 1. The X-ray CT scanner 1*a* includes an imaging condition setting screen 61*c*, which corresponds to, but has a structure slightly different from that of, the imaging condition setting screen 61*b* displayed on the main body controller 60 of the X-ray CT scanner 1.

Hereinafter, the structure of the imaging condition setting screen 61*c* will be described.

The "stitch X-ray CT imaging" is selected on the imaging mode selection screen 61*a*, and thus the imaging condition setting screen 61*c* is displayed on the display 61. Unlike the imaging condition setting screen. 61*b*, the imaging condition setting screen 61*c* includes an irradiation angle setter 636 ("Change Angle" in the figure) on the axial direction imaging region setting screen 600. The irradiation angle setter 636 is a text box that receives a change in the irradiation angle, in the Z-axis direction, of the X-ray cone beam Bx directed from the X-ray emitter 10*a* (see FIG. 26).

The irradiation angle setter 636 is a text box by which a direction in which an irradiation direction L of the X-ray cone beam Bx crosses the horizontal direction (the horizontal direction is 0 degrees) is designated. In the case where a positive value is input, the irradiation direction L of the X-ray cone beam Bx is inclined upward; whereas in the case where a negative value is input, the irradiation direction L of the X-ray cone beam Bx is inclined downward.

The irradiation angle setter 636 is a text box to which a value may be input. Alternatively, the inclination of the irradiation direction D of the X-ray cone beam Bx may be designated by the designation cursor 612 on the image display 610, on which a schematic view of the X-ray generator 10 is displayed.

Now, a structure at inclining the irradiation direction L of the X-ray cone beam Bx in response to the value input to the irradiation angle setter 636 will be described.

The operator inputs a predetermined value to the irradiation angle setter 636, and thus the main body controller 60 controls the X-ray irradiation range restrictor drivers 16. In more detail, under the control of the X-ray irradiation range restrictor driving controller 60*h*, the upper length direction blocking plate 14*a* and the lower length direction blocking plate 14*b* are slid in the up-down direction to change the irradiation direction of the X-ray cone beam Bx.

Figure 27:
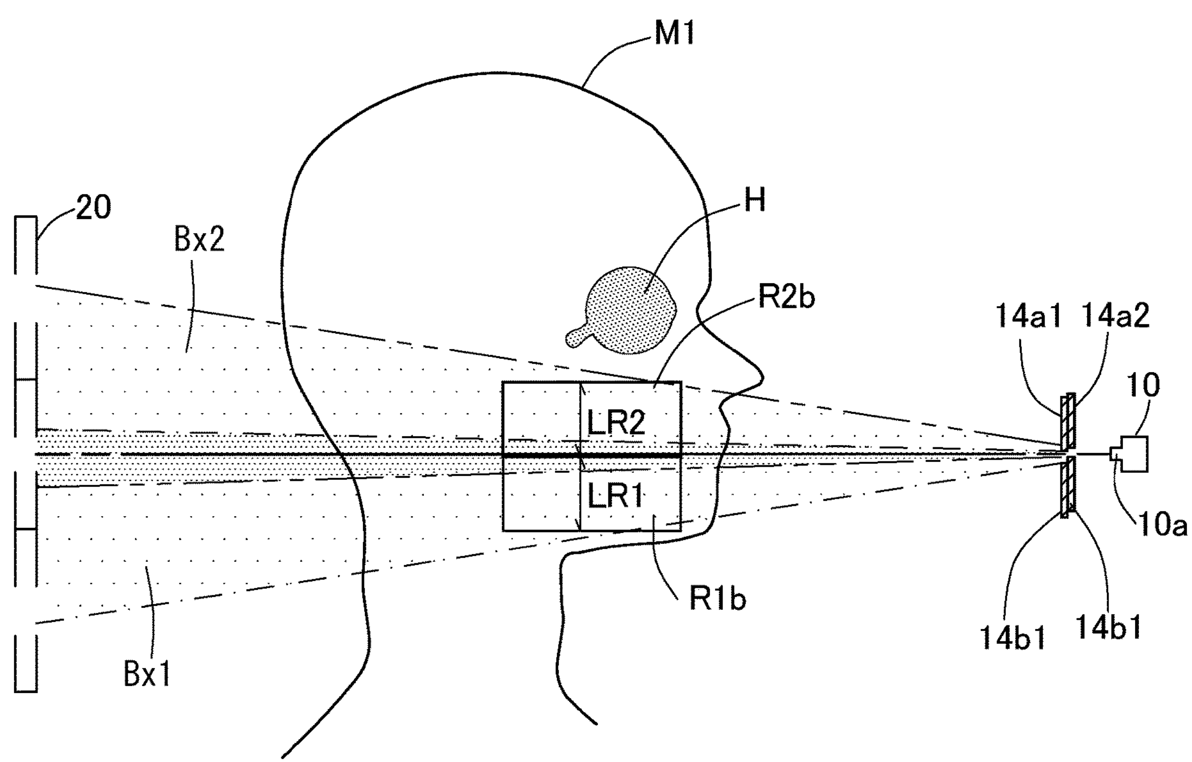
FIG. 27 illustrates the stitch X-ray CT imaging performed by adjusting the irradiation direction of the X-ray cone beam.
Figure 28:
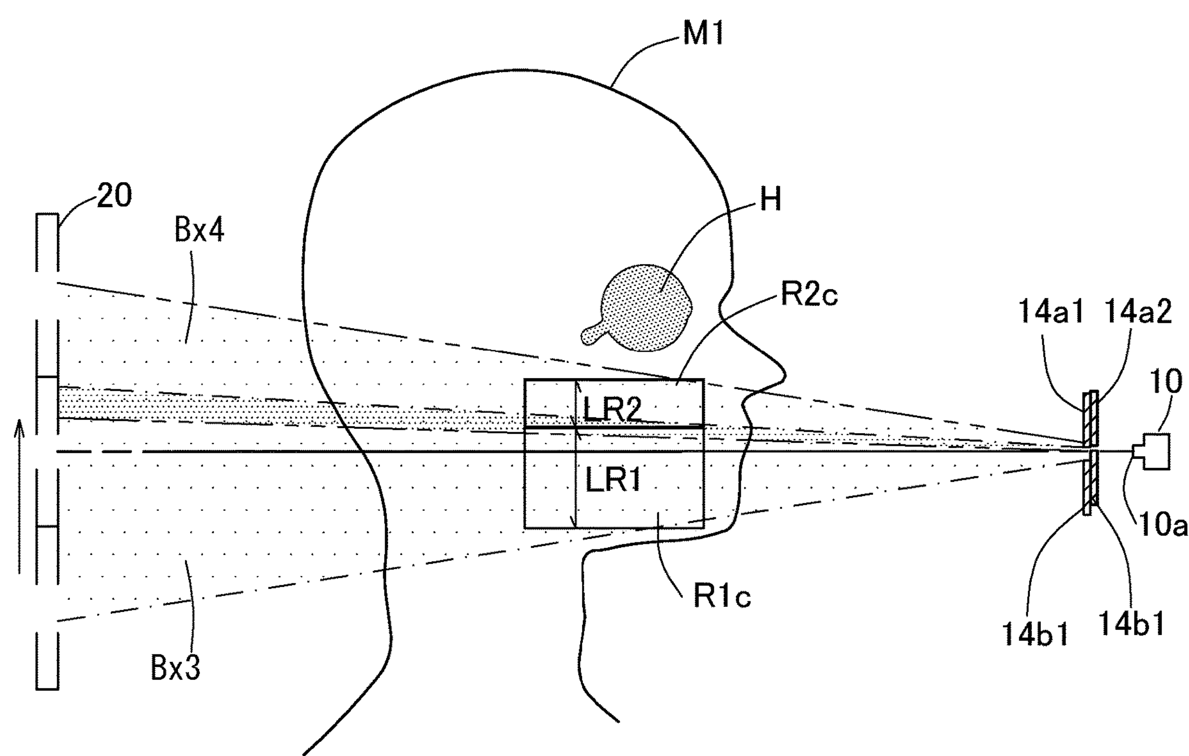
FIG. 28 illustrates the stitch X-ray CT imaging performed by changing the height of the region and adjusting the irradiation direction of the X-ray cone beam.

In the case where, for example, as shown in FIG. 27, the X-ray CT imaging of the first imaging region Rib is performed, the upper length direction blocking plate 14*a* (upper length direction blocking plate 14*a*1 in the figure) and the lower length direction blocking plate 14*b* (lower length direction blocking plate 14*b*1 in the figure) are moved downward to change the irradiation direction L of the X-ray cone beam Bx to a downward direction (Bx1 in the figure). Thus, the X-ray cone beam Bx may be directed toward the first imaging region Rib.

In this process, the X-ray detector driving controller 60*f* controls the downward movement of the X-ray detector 20, and thus the X-ray cone beam Bx1 directed downward may be detected even by the small X-ray detection surface 20*a*.

In the case where, for example, the offset X-ray CT imaging of the first imaging region Rib is performed, the revolution arm 30 is revolved in this state at 360 degrees about the revolution center Sc, which is translated in a true circle with respect to the imaging center OA. Thus, the projection data on the first imaging region R1*b* may be collected.

After the offset X-ray CT imaging of the first imaging region R1*b* is finished, the X-ray irradiation range restrictor driving controller 60*h* controls the X-ray irradiation range restrictor drivers 16 such that the upper length direction blocking plate 14*a* (upper length direction blocking plate 14*a*2 in the figure) and the lower length direction blocking plate 14*b* (lower length direction blocking plate 14*b*2 in the figure) are moved upward to change the irradiation direction of the X-ray cone beam Bx to an upward direction (X-ray cone beam Bx2 in the figure). Thus, the X-ray cone beam Bx2 may be directed toward the second imaging region R2*b*.

In addition, the X-ray detector driving controller 60*f* controls the upward movement of the X-ray detector 20 such that the X-ray cone beam Bx2 directed upward may be detected.

In the case where the second imaging region R2*b* is processed by the offset X-ray CT imaging as well as the first imaging region R1*b*, the revolution arm 30 is rotated at 360 degrees about the revolution center Sc, which is translated in a true circle about the imaging center OA. Thus projection data on the second imaging region R2*b* is collected.

In FIG. 27, the upper length direction blocking plate 14*a*1 and the upper length direction blocking plate 14*a*2 represent the same upper length direction blocking plate 14*a*, and the lower length direction blocking plate 14*b*1 and the lower length direction blocking plate 14*b*2 represent the same lower length direction blocking plate 14*b*. The upper length direction blocking plate 14*a*1 and the upper length direction blocking plate 14*a*2 are located on the same side in the Y-axis direction, and the lower length direction blocking plate 14*b*1 and the lower length direction blocking plate 14*b*2 are located on the same side in the Y-axis direction. In FIG. 27, in order to make the change in the irradiation direction easier to understand, the upper length direction blocking plate 14*a*1 and the upper length direction blocking plate 14*a*2 are shown as being shifted with respect to each other in the Y-axis direction, and the lower length direction blocking plate 14*b*1 and the lower length direction blocking plate 14*b*2 are shown as being shifted with respect to each other in the Y-axis direction.

As described above, the irradiation direction of the X-ray cone beam Bx is made different for the first imaging region R1*b* and for the second imaging region R2*b*. Thus, the plurality of regions divided in the Z-axis direction may be processed by the X-ray CT imaging. From the collected projection data, the CT imaging information I may be generated.

The heights, in the Z-axis direction, of the first imaging region R1*b* and the second imaging region R2*b*, namely, the imaging ranges in the Z-axis direction (axial direction imaging range LR1 and axial direction imaging range LR2, respectively) may be changed by the imaging region change setter 635 to perform the X-ray CT imaging of the first imaging region R1*b* and the second imaging region R2*b*.

This is performed as follows specifically. From the numbers of times of imaging (imaging regions) displayed on the pull-down menu appearing when "▼" is pressed, "1" (i.e., imaging region R1) is selected, by the imaging region change setter 635 on the imaging condition setting screen 61*c*, as the number of times of imaging of a target, the height of which in the Z-axis direction is to be changed. A desired imaging range in the Z-axis direction (value of an axial direction imaging range Lr1) is input to the text box to the side of "▼". In this imaging, a value is input to the text box of the imaging region change setter 635 such that the height of the first imaging region R1*c* is higher than the height of the second imaging region R2*c* (LR1>LR2).

In the case where the number of times is a plurality of times, the height of each imaging range is calculated as follows: the difference between the height of the entirety imaging region and the height input to the text box of the imaging region change setter 635 is divided by a value acquired by subtracting the input number of times of imaging from the number of times of imaging. Namely, in the case where the number of times of imaging is 2, the difference between the height of the entire imaging region and the height input to the text box of the imaging region change setter 635 (axial direction imaging range LR1) is the height of the second imaging region R2 (axial imaging range LR2).

Instead of inputting the value to the text box of the imaging region change setter 635, the height of the first imaging region R1*c* (axial imaging range LR1) may be designated by the designation cursor 612 on the imaging range displayed on the CT imaging range display 611.

In this embodiment, the content input to the text box to the side of "▼" is the imaging range in the Z-axis direction in the number of times of imaging (imaging region), which is the target. Alternatively, for example, a ratio with respect to the entire imaging region may be input.

The height in the Z-axis direction is set for each imaging region in this manner. Thus, the imaging mode setting reader 60*a* controls the saving of the imaging conditions. Based on the saved imaging conditions, the X-ray irradiation range restrictor driving controller 60*h* controls the X-ray irradiation range restrictor drivers 16 to determine the width of the X-ray cone beam Bx in the Z-axis direction.

In the case where, for example, the first imaging region Rc1, the axial imaging range LR1 of which is set to be higher than the axial imaging range LR2, is set to be processed by the X-ray CT imaging as in this case, the X-ray irradiation range restrictor driving controller 60*h* controls such that the upper length direction blocking plate 14*a*1 is moved upward aria the lower length direction blocking plate 14*b*1 are moved downward to form an X-ray cone beam Bx3 having an extended width in the Z-axis direction. The X-ray generator 10 generating the X-ray cone beam Bx3 formed in this manner and the X-ray detector 20 are revolved around the subject M1 in accordance with the imaging mode. Thus, the projection data on the first imaging region R1*c* is collected.

By contrast, an X-ray cone beam Bx4 directed toward the second imaging region R2*c*, the axial imaging range LR2 of which is set to be lower than the axial imaging range LR1, is formed as follows. The X-ray irradiation range restrictor driving controller 60*h* controls such that the upper length direction blocking plate 14*a* (upper length direction blocking plate 14*a*2 in the figure) is moved upward slightly and the lower length direction blocking plate 14*b* (lower length direction blocking plate 14*b*2 in the figure) is moved upward. Thus, the X-ray cone beam Bx4 is narrower in the width in the Z-axis direction than the X-ray cone beam Bx3.

The X-ray generator 10 generating the X-ray cone beam Bx4 formed in this manner and the X-ray detector 20 are revolved around the subject M1 in accordance with the imaging mode. Thus, the projection data on the second imaging region R2*c* lower than the first imaging region R1*c* may be collected.

As described above, the X-ray CT scanner 1*a* includes the imaging region change setter 635 setting the axial imaging range LR1 and the axial imaging range LR2 and also includes the X-ray irradiation range restrictor driving controller 60*h* changing the width, in the Z-axis direction, of the X-ray cone beam Bx in accordance with a first imaging region R1*v* and a second imaging region R2*v* set by the imaging region change setter 635. Thus, the X-ray CT imaging may be performed on regions having different heights.

In the case where, for example, the axial imaging range LR1 and the axial imaging range LR2 have the same value, an upper limit may be set on the second imaging region R2*c* corresponding to an upper region such that X-ray cone beam Bx is not directed toward the high sensitivity site H such as an eyeball or the like. In this case, a site of best interest may be included in the overlapping region Rw, which is an overlapping portion of the first imaging region R1*c* and the second imaging region R2*c*. In this case, the overlapping image information Iw on the overlapping region Rw is generated by averaging a plurality of pieces of the first CT imaging information I1*c* and a plurality of pieces of second CT imaging information I2*c*, and therefore, may be undesirably incorrect.

However, the above-described structure allows the site of the best interest to be offset from the overlapping region Rw. Therefore, correct CT imaging information I may be generated on the site of the best interest.

The X-ray cone beam Bx3, and the X-ray cone beam Bx4 formed as described above are close to each other while being parallel to each other in the overlapping region Rw, in which the first imaging region R1 and the second imaging region R2 overlap each other. Therefore, the first CT imaging information I1 corresponding to the first imaging region R1 and the second CT imaging information I2 corresponding to the second imaging region R2 are joined with each other as information with fewer errors. Thus, the joining may be performed correctly.

In addition, for example, the X-ray generator 10 may be moved up and down in the Z-axis direction under the control of the X-ray generator driving controller 60*i*. Therefore, the X-ray cone beam Bx1 and the X-ray cone beam Bx2 directed toward the overlapping region Rw may be made more parallel to each other (see FIG. 29).

Figure 29:
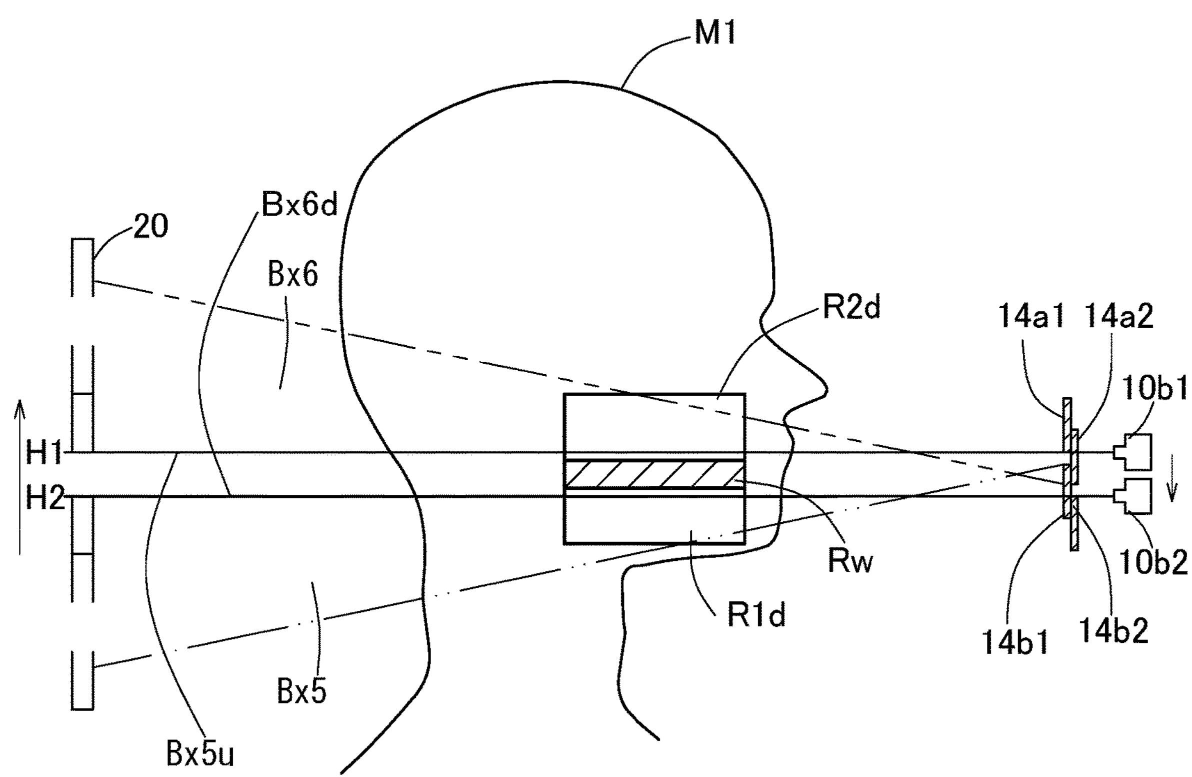
FIG. 29 illustrates the adjustment of the irradiation direction of the X-ray cone beam by another method.

This will be described more specifically. In the case where as shown in FIG. 29, the X-ray CT imaging of the first imaging region R1, which is a lower region, is performed, the X-ray generator 10 (10*b*1 in the figure) is located such that a horizontal line H1 drawn from the center of the X-ray generator 10 toward the X-ray detector 20 is above the overlapping region Rw, in which a first imaging region R1*d* and a second imaging region R2*d* overlap each other.

The upper length direction blocking plate 14*a* (14*a*1 in the figure) is moved such that a bottom end thereof s located at the center of the opening 17, and the lower length direction blocking plate 14*b* (14*b*1 in the figure) is moved downward. Thus, an X-ray cone beam Bx5 directed downward may be generated.

Since the bottom end of the upper length direction blocking plate 14*a* is located at the center of the opening 17, the X-ray cone beam Bx directed upward from the X-ray emitter 10*a* is blocked by the upper length direction blocking plate 14*a*. Therefore, a top surface of the X-ray cone beam Bx5 formed to have a truncated polygonal shape is generally parallel to the horizontal direction.

The top surface Bx5*u* of the X-ray cone beam Bx5 formed in this manner irradiates a region above the overlapping region Rw.

In the case where as shown in FIG. 29, the X-ray CT imaging of the second imaging region R2*d*, which is an upper region, is performed, the X-ray generator 10 (10*b*2 in the figure) is located such that a horizontal line H2 drawn from the center of the X-ray generator 10 toward the X-ray detector 20 is below the overlapping region Rw, in which the first imaging region R1*d* and the second imaging region R2*d* overlap each other.

The upper length direction blocking plate 14*a* (14*a*2 in the figure) is moved upward, and the lower length direction blocking plate 14*b* (14*b*2 in the figure) is moved such that a top end thereof is located at the center of the opening 17. Thus, an X-ray cone beam Bx6 directed upward may be generated.

Since the top end of the lower length direction blocking plate 14*b* is located at the center of the opening 17, the X-ray cone beam Bx directed downward from the X-ray emitter 10*a* is blocked by the lower length direction blocking plate 14*b*. Therefore, a bottom surface of the X-ray cone beam. Bx6 formed to have a truncated polygonal shape is generally parallel to the horizontal direction.

The bottom surface Bx6*d* of the X-ray cone beam Bx6 formed in this manner irradiates a region below the overlapping region Rw.

The X-ray cone beam Bx5 and the X-ray cone beam Bx6 formed in this manner are directed toward the overlapping region Rw, which is an overlapping portion of the first imaging region R1*d* and the second imaging region R2*d*, in a direction almost parallel to the horizontal direction. Therefore, the projection data on the overlapping region Rw collected by the imaging of the first imaging region R1*d* and the projection data on the overlapping region Rw collected by the imaging of the second imaging region R2*d* are highly matched to each other.

Therefore, first CT imaging information I1*d* generated based on the protection data on the first imaging region R1*d*, and second CT imaging information I2*d* generated based on the protection data on the second imaging region R2*d*, are both with fewer errors. Therefore, the joining may be performed more accurately, and stitch imaging information Is with improved precision may be generated.

Figure 30:
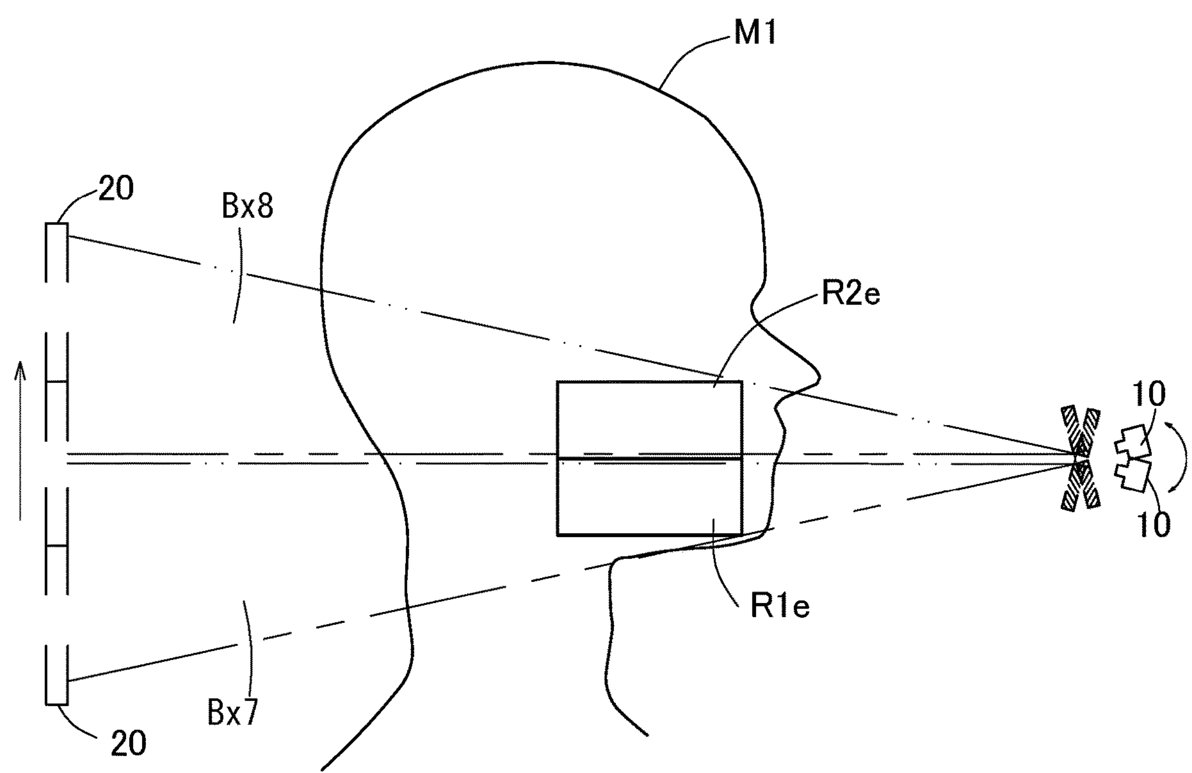
FIG. 30 illustrates the stitch X-ray CT imaging performed by adjusting an angle of the X-ray generator.

As shown in FIG. 30, the X-ray generator driving controller 60*i* may control the inclination of the X-ray generator 10, so that the X-ray cone beam Bx horizontal to the overlapping region Rw of a first imaging region P1*e* and a second imaging region R2*e* may be directed (Bx7 directed toward the first imaging region R1*e* and Bx8 directed toward the second imaging region R2*e*).

The X-ray CT scanner 1 performes X-ray CT imaging of an imaging region CA in a subject M1 to generate an CT imaging information I of said imaging region CA by detecting an X-ray cone beam Bx irradiated from an X-ray generator 10 with an X-ray detector 20. The X-ray CT scanner 1 comprises the revolution arm 30 locating the X-ray generator 10 and the X-ray detector 20 such that the X-ray generator 10 and the X-ray detector 20 face each other while having the subject M1 therebetween; the XY table 35 relatively moving an irradiation direction D of the X-ray cone beam Bx irradiated from the X-ray generator 10, with respect to a center of the imaging region CA such that the irradiation direction is offset from the center of the imaging region CA in a reference plane vertical to an imaging central axis of the imaging region CA; the axial direction changing mechanism 43 changing as the imaging region CA from a first imaging region R1 to which the X-ray CT imaging is executed first by the X-ray generator 10 and the X-ray detector 20 to a second imaging region R2 to which the X-ray CT imaging is executed after the first imaging region R1 in an axial direction of the imaging central axis, said imaging region CA comprising the first imaging region R1 and the second imaging region R2; the main body controller 60 controlling the X-ray CT imaging to revolve the revolution arm 30 with respect to the subject M1 to generate the CT imaging information I; and the stitch imaging information generator 861*b* generating stitch imaging information Is acquired as a result of joining first CT imaging information I1 on the first imaging region R1 and second CT imaging information I2 on the second imaging region R2 in the axial direction, the first CT imaging information I1 and the second CT imaging information I2 partially overlapping each other in the axial direction. The X-ray CT scanner 1 is configured to be capable of executing control on offset CT imaging of controlling the XY table 35 such that the X-ray cone beam Bx is always directed toward a part of the imaging region CA throughout the imaging, and control on the axial direction changing mechanism 43 to generate the first CT imaging information I1 and the second CT imaging information I2 partially overlapping each other in the axial direction. The stitch image information generator 861*b* generates the stitch imaging information Is comprising the first CT imaging information I1 and the second CT imaging information I2, and at least one of the first CT imaging information I1 and the second CT imaging information I2 being offset CT imaging information Io acquired by the offset CT imaging. Thus, the CT imaging information I on a large imaging region CA may be generated with certainty even with the X-ray detector 20 configured such that the X-ray detection surface 20*a* is small. This will be described in more detail. The imaging region CA may be processed by the offset CT imaging under the control on the XY table 35 by the main body controller 60. Therefore, the imaging region CA that is long in a width direction crossing the axial direction may be processed by X-ray CT imaging even with the X-ray detector 20 configured such that X-ray detection surface 20*a* is small. Therefore, the offset CT imaging information Io including information on the region that is long in the width direction may be generated.

In addition, the main body controller 60 controls the axial direction changing mechanism 43 and includes the stitch image information generator 861*b*. Thus, the imaging region CA may be changed in the axial direction such that the first CT imaging information I1 and the second CT imaging information I2 partially overlapping each other may be generated during the X-ray CT imaging. Moreover, the stitch imaging information Is may be generated by joining the first CT imaging information I1 and the second CT imaging information I2 generated by the X-ray CT imaging.

As described above, in the direction crossing the Z-axis direction, the offset CT imaging information Io including information on a large region may be generated. In the Z-axis direction, pieces of CT imaging information I acquired by the imaging performed with the imaging region CA being divided into a plurality of regions may be joined with each other. Therefore, X-ray CT imaging information on the entirety of the large imaging region CA may be generated with certainty even with the X-ray detector 20 configured such that the X-ray detection surface 20*a* is small. Thus, for example, the X-ray CT scanner 1 may be made lightweight, and the cost may be decreased.

The XY table 35 moves a revolution center Sc of the revolution arm 30 in a circular track about a central axis of the imaging region CA in the reference plane. Thus, the offset CT imaging information Io may be generated without moving or rotating the subject M1. Therefore, the load on the subject M1 may be alleviated.

The subject M1 may be secured without being moved. Therefore, the subject M1 may be prevented from unintentionally moving by, for example, the vibration at the start of the movement or at the finish of the imaging. For these reasons, accurate offset CT imaging may be performed, and the first CT imaging information I1 and the second CT imaging information I2 may be joined with each other with more certainty.

The axial direction changing mechanism 43 may be configured to move at least one of the revolution arm 30 and the subject M1 in a revolution center Sc direction along a revolution axis center of the revolution arm 30 with respect to the other of the revolution arm 30 and the subject M1. Thus, the target of irradiation may be changed from the first imaging region R1 to the second imaging region R2 in the Z-axis direction with a simple structure. Therefore, the X-ray CT scanner 1 does not need to have a complicated structure, and the productivity may be improved.

A range of the imaging region CA in which a plurality of pieces of CT imaging information I overlap each other in the Z-axis direction may be found by an amount of movement, in the axial direction, of at least one of the revolution arm 30 and the subject M1 with respect to the other of the revolution arm 30 and the subject M1. Therefore, the amount of movement in the axial direction in a process of joining the plurality of pieces of CT imaging information I may be used as a parameter value. For this reason, the computation load may be alleviated, and the stitch imaging information Is may be generated at a higher speed.

The axial direction changing mechanism 43 may change the position of the revolution arm 30 in a direction away from the subject M1 after the X-ray CT imaging of the first imaging region R1 is performed. Thus, during the change to the second imaging region R2 after the imaging of the first imaging region R1, the position of the revolution arm 30 may be changed in the direction away from the subject M1. Therefore, the revolution arm 30 may be prevented from approaching and interfering with the subject M1. Thus, the X-ray CT imaging may be performed safely. The revolution arm 30 does not approach the subject M1 too closely, and therefore, may be prevented from imposing any oppressive feeling on the subject M1.

The controller 84 may include the overlapping amount setter 634 adjusting an overlapping amount of the first imaging region R1 and the second imaging region R2. Thus, the overlapping amount adjusted between the first CT imaging information I1 and the second CT imaging information I2 may be prepared in advance. Therefore, the precision of the stitch imaging information Is is generated by joining the first CT imaging information I1 and the second CT imaging information I2 may be improved.

An imaging mode in which the center of the imaging region CA matches the revolution center of the revolution arm 30 during revolution and the X-ray cone beam Bx always passes the entirety of the imaging region CA on the reference plane throughout the imaging being a normal imaging mode. An imaging mode in which the offset CT imaging is performed being an offset imaging mode. An imaging mode in which at least one offset CT imaging information Io and an CT imaging information I of an imaging region CA that is different from the imaging region CA to which the X-ray CT imaging is executed for said offset CT imaging information Io are combined and integrated being an offset stitch imaging mode. The X-ray CT scanner 1 may include an imaging mode selector selecting any one of these imaging modes. Thus, the imaging mode suitable to the size of the imaging region CA may be appropriately selected. Therefore, the X-ray CT imaging of the imaging region CA may be performed appropriately. Thus, the amount of the X-ray to which the subject M1 is exposed may be suppressed.

The X-ray CT scanner 1 may include the display 81 displaying a stitch image based on the stitch imaging information Is generated by the stitch imaging information generator 861*b*.

Thus, the stich image corresponding to the imaging region CA may be displayed, and a CT image of the imaging region CA may be observed with a human eye.

The X-ray CT scanner 1 may include the setting information control display 601 and the high sensitivity site determiner 60*m* determining whether the X-ray CT imaging of the imaging region CA changed in the axial direction under the control of the axial direction changing mechanism 43 is possible of not; and notifier 90 performing notification based on determination results of the setting information control display 601 and the high sensitivity site determiner 60*m*. Thus, the determination results of the setting information control display 601 and the high sensitivity site determiner 60*m* may be notified by the notifier 90. Therefore, the X-ray CT imaging may be performed more safely.

The main body controller 60 may execute continuously first imaging control of controlling the X-ray CT imaging of the first imaging region R1 and second imaging control of controlling the X-ray CT imaging of the second imaging region R2. Thus, the plurality of pieces of CT imaging information I may be generated by a series of processes. Therefore, it is not needed to perform position alignment or the like before the imaging each time the plurality of pieces of CT imaging information I are generated. Thus, the degree of alignment among the plurality of pieces of CT imaging information I may be improved.

The X-ray CT scanner 1 may include the X-ray irradiation range restrictor drivers 16 forming the X-ray cone beam Bx directed toward the imaging region CA; the revolution shaft 31 revolving the revolution arm 30 around the subject M1; and the main body controller 60 controlling at least the X-ray irradiation range restrictor drivers 16 and the revolution shaft 31. A direction perpendicular to the axial direction being a lateral direction. The X-ray irradiation range restrictor drivers 16 may include the lateral direction blocking plates 15 blocking an irradiation range in the lateral direction of the X-ray cone beam Bx to the imaging region CA such that the X-ray cone beam Bx is allowed to be changed to an X-ray thin beam. The main body controller 60 being configured to direct the X-ray thin beam formed by changing a restriction range restricted by the X-ray irradiation range restrictor drivers 16, to revolve the revolution arm 30, thus to control the revolution shaft 31 such that the directed X-ray thin beam forms a panorama X-ray imaging track locus, and to perform the panorama imaging with the X-ray thin beam. Thus, the X-ray CT imaging and also the panorama imaging may be performed. Therefore, the X-ray imaging suitable to the purpose of treatment may be performed.

The first CT imaging information I1 or the second CT imaging information I2, based on which the stitch imaging information Is is generated, may include CT imaging information I on an imaging region CA having a radius, on the reference plane, different from that of an imaging region CA representing another CT imaging information I. Thus, the pieces of the CT imaging information acquired by the X-ray CT imaging performed in accordance with the imaging regions CA may be generated as the stitch imaging information Is.

This will be described in more detail. Stitch imaging information Is in which offset CT imaging information Io acquired by the imaging performed on a large imaging region CA and cylindrical CT imaging information I having a different radius from that of the offset Cr imaging information Io are joined with each other may be generated.

In the case where, for example, the imaging region represented by the CT imaging information I other than the offset CT imaging information Io includes the high sensitivity site H, the normal X-ray imaging may be performed on only a predetermined range avoiding the high sensitivity site H. The CT imaging information I generated in this manner and the offset CT imaging information Io may be joined with each other to generate the stitch imaging information Is. In this manner, stitch imaging information Is in accordance with the X-ray CT imaging performed in accordance with the imaging region CA of the subject M1 may be generated.

Overlapping portion, in the stitch imaging information Is, of the first CT imaging inform I1 and the second CT imaging information I2 joined with each other may be averaged Thus, stitch imaging information Is in which the overlapping portion of the CT imaging information I is adjusted may generated.

The CT imaging information is weighted and thus averaged in accordance with the position, in the axial direction, of the two joined pieces of the CT image information. Thus, stitch imaging information Is that does not clearly show the border between the different pieces of the CT image information I including the overlapping image information Iw may generated.

The information processing device 8 may include the image constructor 862 generating, based on the first CT imaging information I1 and the second CT imaging information I2, X-ray image of each of the imaging regions CA. Thus, the stitch image based on the stitch imaging information Is, and the X-ray image in accordance with the region of each of the first CT imaging information I1 and the second CT imaging information I2, may be displayed separately. Therefore, it is not needed to construct any individual X-ray image from the stitch imaging information Is, and the data capacity may be decreased. In addition, for example, the image may be observed in the state where the pieces of the information do not overlap each other.

The cursor 822 designating a desired position on three dimensional axes perpendicular to each other on the display 81, and the cross-section image constructor 862*c* generating sectional image information corresponding the position designated by the cursor 822, are provided. Thus, a desired cross-sectional view may be displayed. Therefore, an internal structure of a tooth, for example, the shape of a root canal as a target of the treatment, may be grasped.

The imaging region according to the present invention corresponds to the imaging region CA in the above-described embodiment; and similarly, the X-ray imaging information corresponds to the CT imaging information I;

the supporter corresponds to the revolution arm 30;

the offset mechanism corresponds to the XY table 35;

the axial direction changing mechanism corresponds to the axial direction changing mechanism 43 and the length direction blocking plates 14;

the imaging controller corresponds to the main body controller 60;

the offset CT imaging information corresponds to the offset CT imaging information Io, the first CT imaging information I1, and the first CT imaging information I1*a;* the offset stitch image information corresponds to the stitch imaging information Is;

the rotation center moving mechanism corresponds to the XY table 35;

the axial direction irradiation angle adjusting mechanism corresponds to the length direction blocking plates 14;

the adjustment controller corresponds to the overlapping amount setter 634;

the imaging mode selector corresponds to the imaging mode selection screen 61*a;* the display and the image display each correspond to the display 81;

the determiner corresponds to the setting information control display 601 and the high sensitivity site determiner 60*m;* the X-ray restrictor corresponds to the X-ray irradiation range restrictor drivers 16;

the imaging mechanism driver corresponds to the revolution shaft 31;

the panorama imaging controller corresponds to the main body controller 60;

the lateral direction X-ray blocker corresponds to the lateral direction blocking plates 15;

the X-ray image processor corresponds to the information processing device 8;

the X-ray image generator corresponds to the image constructor 862;

the designation operation interface corresponds to the cursor 822; and the sectional image information processor corresponds to the cross-section image constructor 862*c.*

The present invention is not limited to having the structure of the above-described embodiment and may be carried out in any of many embodiments.

Figure 31:
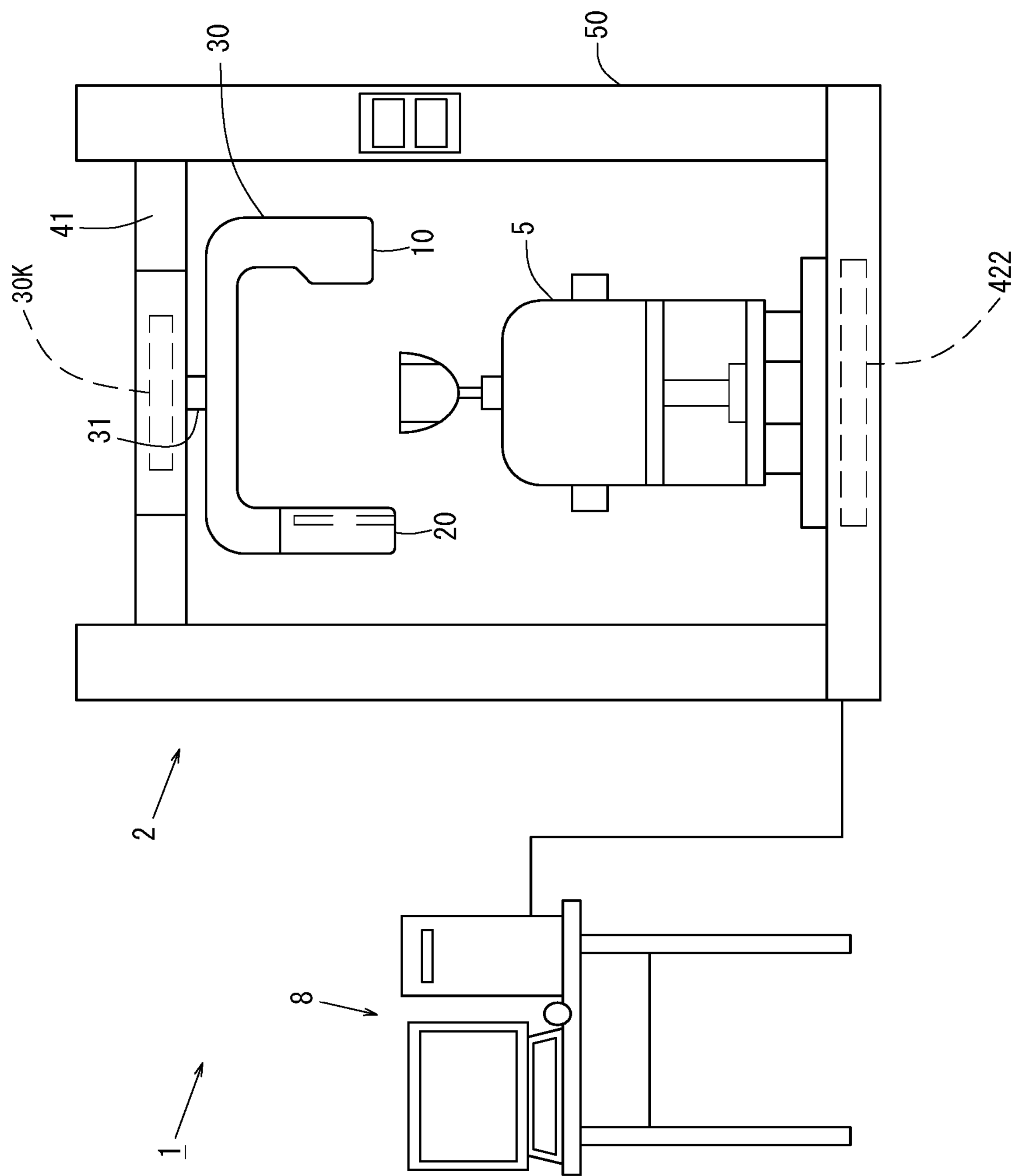
FIG. 31 is a schematic front view of a second X-ray CT scanner.
Figure 32:
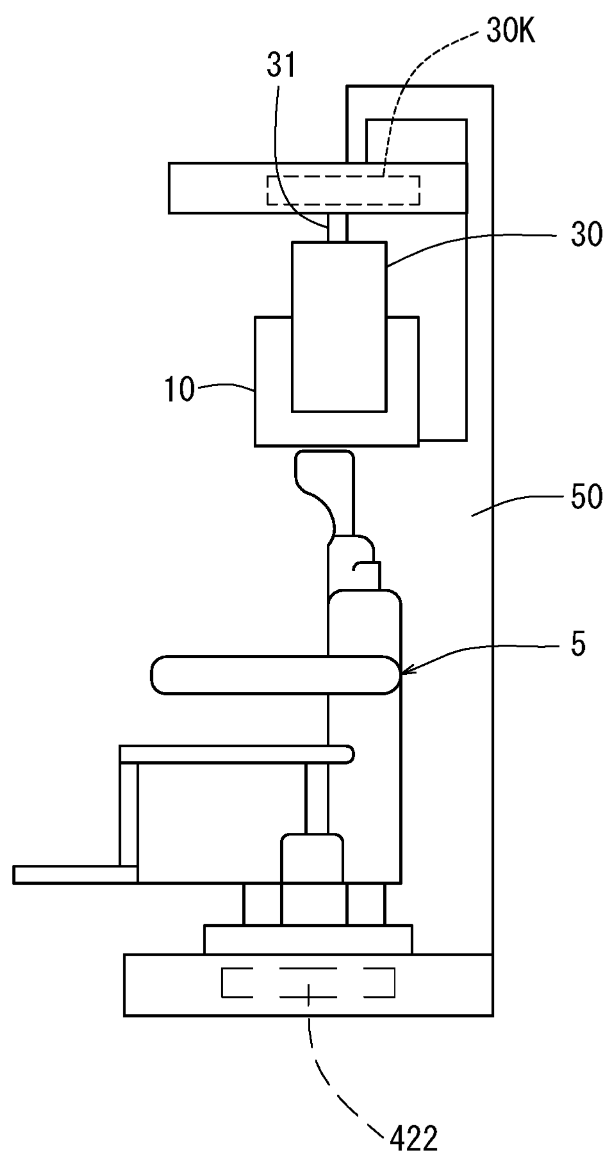
FIG. 32 is a schematic side view of the second. X-ray CT scanner.

For example, in the above-described embodiment, the height of the revolution arm 30 is controlled with respect to the subject M1 to control the revolution plane of the revolution arm 30. As shown in FIG. 31 and FIG. 32, a chair 5, on which the subject M1 is to sit, may be provided, so that the chair 5 is controlled to move the revolution shaft of the revolution arm 30 with respect to the subject M1.

Figure 33:
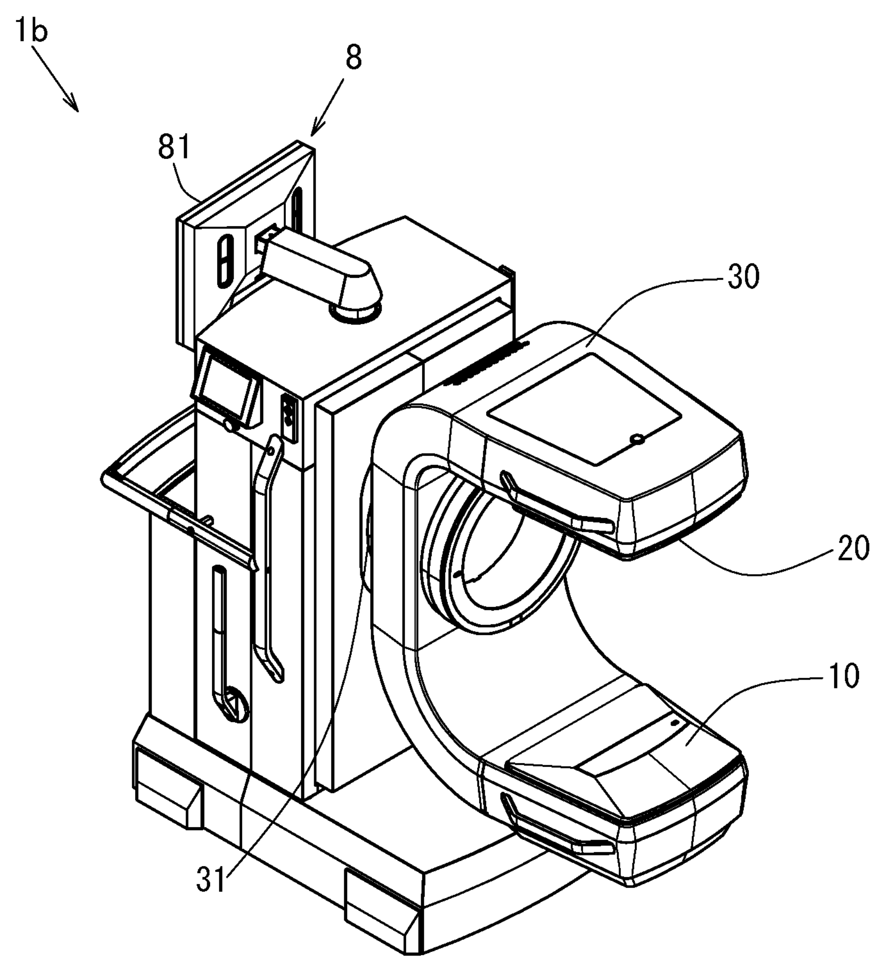
FIG. 33 is a schematic perspective view of a third X-ray CT scanner.

Alternatively, for example, as shown in FIG. 33, the revolution arm 30 may be supported by the upper frame 41 standing in the Z-axis direction and may be revolved about one axis in the horizontal direction (Y-axis) as the revolution axis, and the subject M1 may be located in the horizontal direction with respect to the revolution arm 30. In this case, the revolution arm 30 or the subject M1 is movable in the horizontal direction, and the subject M1 and the revolution shaft of the revolution arm 30 are movable with respect to each other.

The structure of offsetting the imaging mechanism 3 with respect to the imaging center (center of the imaging region) OA, namely, the structure of moving the irradiation direction of the X-ray cone beam Bx with respect to the imaging center OA, may be real zed by lacing and offsetting the revolution shaft 31 by the revolution shaft moving mechanism 34. Alternatively, the structure may be realized by displacing and offsetting the subject holder 42H with respect to the imaging center OA. In this case, even if the revolution shaft 31 is secured in the XY plane the subject holder 42H is displaced and offset with respect to the revolution shaft 31. Still alternatively, both of the revolution shaft 31 and the subject holder 42H may be displaced to realize the structure.

Alternatively, for example, the chair 5 in FIG. 31 and FIG. 32 acts as the subject holder 42H, and includes the subject holder driver 424 in a base portion thereof. The subject holder driver 424 has substantially the same structure as that of the revolution shaft moving mechanism 34, and drives and displaces, in the XY horizontal plane, a portion of the chair 5 on which the patient is to sit, instead of driving the revolution shaft 31. The subject holder driver 424 may be used to offset the head MH of the subject with respect to the center of the imaging region. (During the offset X-ray CT imaging, the head MH secured by the portion of the chair 5 on which the patient is sit is moved on a circular track with respect to the imaging center OA.)

The above-described irradiation direction is moved with respect to the imaging center OA of the imaging region by controlling the XY table to revolve the revolution arm 30 while moving the position of the revolution shaft 31 of the revolution arm 30 with respect to the imaging center OA of the imaging region CA. Alternatively, the irradiation direction may be moved with respect to the imaging center OA of the imaging region by, for example, the structure of changing the irradiation direction of the X-ray cone beam Bx directed from the X-ray generator 10 while securing the revolution arm 30 and the subject M1, by the structure of changing the irradiation direction of the X-ray cone beam Bx directed from the X-ray generator 10 while moving at least one of the revolution arm 30 and the subject M1, by the structure of revolving the secured revolution arm 30 while moving the subject M1, or by the structure of moving both of the revolution arm 30 and the subject M1.

The structure of changing the irradiation direction of the X-ray cone beam Bx refers to moving the left lateral direction blocking plate 15*a* and the right lateral direction blocking plate 15*b* under the control of the X-ray irradiation range restrictor drivers 16 and thus changing the irradiation direction D of the X-ray cone beam. Bx. This may offset the irradiation direction D of the X-ray cone beam Bx from the imaging center OA of the imaging region CA.

As described above, the revolution arm 30 is revolved around the subject M1 about the revolution shaft 31 as the revolution center Sc in the state where the X-ray cone beam Bx is offset from the imaging center OA. Thus, the offset CT imaging of the region of interest may be performed.

In other words, the length direction blocking plates 14 change the irradiation direction of the X-ray cone beam Bx in the axial direction with respect to the revolution arm 30. Thus, the irradiation direction of the X-ray cone beam Bx directed from the X-ray generator 10 is moved without moving the revolution arm 30 supporting the X-ray generator 10 and the X-ray detector 20. In this manner, the target of irradiation may be changed from the first imaging region R1 to the second imaging region R2. Therefore, the CT imaging may be performed without imposing any oppressive feeling on the patient as the subject M1.

The axial direction changing mechanism 43 or the length direction blocking plates 14 may be, for example, configured to change the region as the target of the imaging in the Z-axis direction by moving the revolution arm 30 supporting the x-ray generator 10 and the X-ray detector 20 in the Z-axis direction, may be configured to change the region as the target of the imaging in the Z-axis direction by moving only the X-ray generator 10 and the X-ray detector 20 provided on the revolution arm 30 in the state where the revolution arm 30 is secured, may be configured to change the region as the target of the imaging in the Z-axis direction by controlling a collimator (X-ray irradiation range restrictor drivers 16) changing the irradiation direction or the irradiation position of the X-ray cone beam Bx directed from the X-ray generator 10, may be configured to change the region as the target of the imaging in the Z-axis direction by moving the subject M1 in the axial direction, or may be configured to change the region as the target of the imaging in the Z-axis direction by a combination thereof.

The first CT imaging information I1 and the second CT imaging information I2, based on which the stich image information is generated, may each include the offset CT imaging information Io, and the pieces of the offset CT imaging information Io may be offset by different distances from the center of the imaging region CA in a reference plane. Thus, the stitch imaging information Is may be generated by joining the pieces of the offset CT imaging information Io having different radii.

Figure 23:
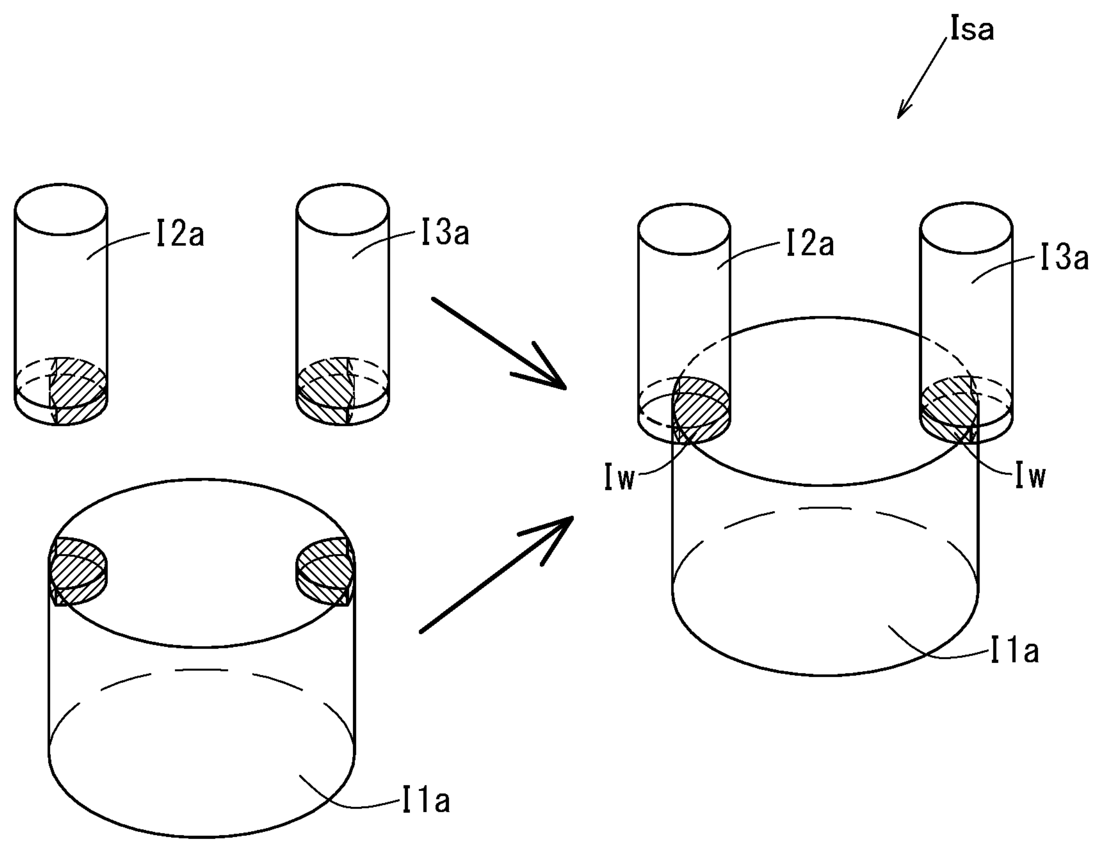
FIG. 23 illustrates the joining of normal CT imaging information and the offset CT imaging information.

As shown in FIG. 23, the first CT imaging information I1 and the second CT imaging information I2 having a cylindrical shape and partially overlapping each other in the axial direction may have the same radius as each other or different radii from each other. The centers thereof may be located at different positions.

In this embodiment, it is determined whether the X-ray CT imaging is physically possible or not because there may be a case where the revolution arm 30 and the subject M1 possibly physically contact each other and thus the imaging is not possible. Alternatively, it may be detected that the imaging region CA may possibly include a high sensitivity site H highly sensitive to the X-ray or that the high sensitivity site H may possibly be included in the range overlapping the imaging region CA, and it may be determined whether the X-ray CT imaging is possible or not.

The averaging is performed by weighting the CT imaging information I in accordance with each of the positions, in the Z-axis direction, in the CT imaging information I acquired as a result of the joining in the Z-axis direction. Alternatively, the averaging may be simply performed with no consideration of the overlapping position. Still alternatively, the weighting may be performed in accordance with the difference in the amount of information such as, for example, the resolution or the like.

As described above, according to this application, the irradiation of the imaging region with the X-ray cone beam Bx is performed by directing the X-ray cone beam toward the imaging region while revolving the revolution arm 30. The revolution accompanied by the irradiation of the imaging region with the X-ray cone beam is defined as “irradiation revolution”, and the amount of the angle of irradiation revolution is defined as “irradiation revolution angle”.

In the above description, the expressions that “revolved at 180 degrees”, “revolved at 360 degrees” and the like used regarding the revolution performed while the X-ray is directed toward the imaging region are used for the “irradiation revolution”.

According to this application, in order to perform the offset X-ray CT imaging, it is preferred that the irradiation revolution angle of the X-ray cone beam toward the imaging region is 360 degrees. The irradiation revolution angle may exceed 360 degrees. However, the irradiation revolution angle of 360 degrees fulfills the conditions under which the projection data of 180 degrees or greater is acquired at any point in the imaging region, and also suppresses the subject M1 from being exposed to the X-ray. Therefore, the irradiation revolution angle of 360 degrees is preferred for the reconstruction of the CT image and the restriction on the b exposure of the subject M1 to the X-ray. In actuality, the irradiation revolution angle does not need to be exactly 360 degrees, but there is a range in which there is no problem regarding the reconstruction of the image and the exposure to the X-ray. Thus, the angle of 360 degrees may be considered as about 360 degrees.

It is preferred that the irradiation revolution angle in the normal X-ray CT imaging is the sum of 180 degrees and the fan angle of the X-ray cone beam. It is known that in fact, the projection data required for the diagnosis is acquired even if the irradiation revolution angle is 180 degrees. Therefore, the irradiation revolution angle of 180 degrees or greater and less than the sum of 180 degrees and the fan angle fulfills the conditions under which the projection data of generally 180 degrees or greater is acquired at any point in the imaging region, and also suppresses the subject M1 from being exposed to the X-ray. Therefore, the irradiation revolution angle of 180 degrees or greater and less than the sum of 180 degrees and the fan angle is preferred for the reconstruction of the CT image and the restriction on the exposure of the subject M1 to the X-ray. Preferably, the irradiation revolution angle is the sum of 180 degrees and the fan angle because such an angle fulfills the conditions under which the projection data of 180 degrees or greater is acquired at any point in the imaging region, and also suppresses the subject M1 from being exposed to the X-ray. Therefore, such an angle is preferred for the reconstruction of the CT image and the restriction on the exposure of the subject M1 to the X-ray.

In order to improve the quality of the CT image, the irradiation revolution angle in the normal X-ray CT imaging may be 360 degrees. For the CT image reconstruction of generating a high quality CT image, it is preferred to acquire the projection data in one direction and the projection data in an opposite direction thereto at all the points in the imaging region. The irradiation revolution angle may exceed 360 degrees. However, the irradiation revolution angle of 360 degrees fulfills the conditions under which the projection data of 360 degrees is acquired at any point in the imaging region, and suppresses the subject M1 from being exposed to the X-ray while achieving the purpose of acquiring a high quality CT image. Therefore, the irradiation revolution angle of 360 degrees is preferred for the reconstruction of the high quality CT image and the restriction on the exposure of the subject M1 to the X-ray. In actuality, the irradiation revolution angle does not need to be exactly 360 degrees, but there is a range in which there is no problem regarding the reconstruction of the image and the exposure to the X-ray. Thus, the angle of 360 degrees may be considered as about 360 degrees. Needless to say, the irradiation revolution angle may be set to greater than the sum of 180 degrees and the fan angle and 360 degrees or less.

As described above, the irradiation revolution angle in the normal X-ray CT imaging may be preferably 180 degrees or greater and 360 degrees or less.

In order to realize the X-ray irradiation at the set irradiation revolution angle, there may be a preparation period or a driving period for avoiding the braking impact for the revolution arm 30 before and after the X-ray irradiation. The revolution arm 30 may move so as to allow the subject M1 to enter or exit. Therefore, the revolution arm 30 may revolve at an angle exceeding the irradiation revolution angle.

The irradiation revolution is started or finished by, for example, turning on or off the X-ray generation of the X-ray generator 10, by opening or closing a shutter, which is the beam shaping mechanism 13 or some X-ray blocking member, or by allowing the irradiation revolution to be performed only at the set irradiation revolution angle. The X-ray generation may be turned on or off by the X-ray generator driving controller 60*i*.

As described above, in the case where the radius of the first imaging region R1 is long and the radius of another imaging region is short, or in the case where the first imaging region R1 is large and another imaging, region is small, the offset X-ray CT imaging may be performed on the first imaging region R1 whereas the normal X-ray CT imaging may be performed on the another imaging region. Alternatively, the offset X-ray CT imaging may be performed with a long radius on the first imaging region R1 whereas the offset X-ray CT imaging may be performed with a short radius on the another imaging region.

REFERENCE SIGNS LIST

10 X-ray generator
14 length direction blocking plates
16 X-ray irradiation range restrictor drivers
15 lateral direction blocking plates
20 X-ray detector
30 revolution arm
31 revolution shaft
35 XY table
43 axial direction changing mechanism
60 main body controller
61*a* imaging mode selection screen
60*l* setting information control display
60*m* high sensitivity site determiner
634 overlapping amount setter
8 information processing device
81 display
862 image constructor
822 cursor
861*b* stitch image information generator
862*c* cross-section image constructor
90 notifier
Bx X-ray cone beam
CA imaging region
I CT imaging Information
Io offset CT imaging information
I1 first CT imaging information
I1*a* first CT imaging information
Is stitch image information
M1 subject
R1 first imaging region
R2 second imaging region.
R3 third imaging region

The invention claimed is:

1. An X-ray CT scanner performing X-ray CT imaging of an imaging region in a subject to generate an X-ray imaging information of said imaging region by detecting an X-ray cone beam irradiated from an X-ray generator with an X-ray detector, the X-ray CT scanner comprising:

a supporter locating the X-ray generator and the X-ray detector such that the X-ray generator and the X-ray detector face each other while having the subject therebetween;

an offset mechanism relatively moving an irradiation direction of the X-ray cone beam irradiated from the X-ray generator, with respect to a center of the imaging region such that the irradiation direction is offset from the center of the imaging region in a reference plane vertical to an imaging central axis of the imaging region;

an axial direction changing mechanism changing as the imaging region from a first imaging region to which the X-ray CT imaging is executed first by the X-ray generator and the X-ray detector to a second imaging region to which the X-ray CT imaging is executed after the first imaging region in an axial direction of the imaging central axis, said imaging region comprising the first imaging region and the second imaging region, and changing the position of the supporter in a direction away from the subject after the X-ray CT imaging of the first imaging region is performed;

an imaging controller controlling the X-ray CT imaging to revolve the supporter with respect to the subject to generate the X-ray imaging information; and an image information generator generating stitch image information acquired as a result of joining first X-ray imaging information on the first imaging region and second X-ray imaging information on the second imaging region in the axial direction, the first X-ray imaging information and the second X-ray imaging information partially overlapping each other in the axial direction, the X-ray CT scanner being configured to be capable of executing:

control on offset CT imaging of controlling the offset mechanism such that the X-ray cone beam is always directed toward a part of the imaging region throughout the imaging, and control on the axial direction changing mechanism to generate the first X-ray imaging information and the second X-ray imaging information partially overlapping each other in the axial direction, and at least one of the first X-ray imaging information and the second X-ray imaging information being offset CT imaging information acquired by the offset CT imaging, wherein the supporter is returned to a start position by rotating in the opposite direction that it rotated in during the X-ray CT imaging of the first imaging region, and wherein the supporter rotates in the same direction during the X-ray CT imaging of both the first and second imaging regions.

2. The X-ray CT scanner according to claim 1, the offset mechanism including a rotation center moving mechanism moving a revolution center of the supporter in a circular track about a central axis of the imaging region in the reference plane.

3. The X-ray CT scanner according to claim 1, the axial direction changing mechanism being configured to move at least one of the supporter and the subject in a revolution center direction along a revolution axis center of the supporter with respect to the other of the supporter and the subject.

4. The X-ray CT scanner according to claim 1, the axial direction changing mechanism including an axial direction irradiation angle adjusting mechanism changing the irradiation direction of the X-ray cone beam in the axial direction with respect to the supporter.

5. The X-ray CT scanner according to claim 1, the imaging controller including an adjustment controller adjusting an overlapping amount of the first imaging region and the second imaging region.

6. The X-ray CT scanner according to claim 1, an imaging mode in which the center of the imaging region matches a revolution center of the supporter during revolution and the X-ray cone beam always passing the entirety of the imaging region on the reference plane throughout the imaging being a normal imaging mode, an imaging mode in which the offset CT imaging is performed being an offset imaging mode, an imaging mode in which at least one offset CT imaging information and an X-ray imaging information of an imaging region that is different from the imaging region to which the X-ray CT imaging is executed for said offset CT imaging information are combined and integrated being an offset stitch imaging mode, and the X-ray CT scanner including an imaging mode selector selecting any one of these imaging modes.

7. The X-ray CT scanner according to claim 1, including a display displaying a stitch image based on the stitch image information generated by the image information generator.

8. The X-ray CT scanner according to claim 1, including:

a determiner determining whether the X-ray CT imaging of the imaging region changed in the axial direction under the control of the axial direction changing mechanism is possible or not; and a notifier performing notification based on determination results of the determiner.

9. The X-ray CT scanner according to claim 1, the imaging controller executing continuously first imaging control of controlling the X-ray CT imaging of the first imaging region and second imaging control of controlling the X-ray CT imaging of the second imaging region.

10. The X-ray CT scanner according to claim 1, including:

an X-ray restrictor forming the X-ray cone beam directed toward the imaging region;

an imaging mechanism driver revolving the supporter around the subject; and a panorama imaging controller controlling at least the X-ray restrictor and the imaging mechanism driver, a direction perpendicular to the axial direction being a lateral direction, the X-ray restrictor including a lateral direction X-ray blocker blocking an irradiation range in the lateral direction of the X-ray cone beam to the imaging region such that the X-ray cone beam is allowed to be changed to an X-ray thin beam, and the panorama imaging controller being configured to direct the X-ray thin beam formed by changing a restriction range restricted by the X-ray restrictor, to revolve the supporter, thus to control the imaging mechanism driver such that the directed X-ray thin beam forms a panorama X-ray imaging track locus, and to perform a panorama imaging with the X-ray thin beam.

11. The X-ray CT scanner according to claim 1, wherein the supporter returns to the start position by rotating in an upward spiral track in the opposite direction from the direction that the supporter is rotated for the X-ray CT imaging of the first imaging region.

12. An X-ray image processor generating X-ray imaging information on an imaging region of a subject to which X-ray CT imaging is executed, the X-ray image processor comprising:

an image information generator generating stitch image information by joining first X-ray imaging information on a first imaging region to which the X-ray CT imaging is executed first and second X-ray imaging information on a second imaging region to which the X-ray CT imaging is executed after the first imaging region, the first imaging region and the second imaging region being partially overlapping each other along an axial direction of an imaging central axis of the imaging region, at least one of the first X-ray imaging information and the second X-ray imaging information, based on which the stitch imaging information is generated, being offset CT imaging information on the imaging region to which the offset CT imaging is executed, and an overlapping portion, in the stitch image information, of the first X-ray imaging information and the second X-ray imaging information joined with each other being averaged.

13. The X-ray image processor according to claim 12, the first X-ray imaging information and the second X-ray imaging information, based on which the stitch imaging information is generated, each consisting of the offset CT imaging information, and a distance of offset from a center of the imaging region in a reference plane vertical to the imaging central axis in each of said first and second X-ray imaging information is different from other.

14. The X-ray image processor according to claim 12, one of the first X-ray imaging information or the second X-ray imaging information, based on which the stitch imaging information is generated, consisting of X-ray imaging information on an imaging region having a radius, on a reference plane, different from that of an imaging region of other X-ray imaging information.

15. The X-ray image processor according to claim 12, including an X-ray image generator generating, based on the first X-ray imaging information and the second X-ray imaging information, an X-ray image of each of the imaging regions.

16. An X-ray image display, comprising:

the X-ray image processor according to claim 12; and an image display displaying a stitch image generated based on the stitch image information generated by the image information generator.

17. The X-ray image display according to claim 16, including:

a designation operation interface designating a desired position on three dimensional axes perpendicular to each other on the image display; and a sectional image information processor generating sectional image information corresponding the position designated by the designation operation interface.

18. An X-ray CT scanner performing X-ray CT imaging of an imaging region in a subject to generate an X-ray imaging information of said imaging region by detecting an X-ray cone beam irradiated from an X-ray generator with an X-ray detector, the X-ray CT scanner comprising:

a supporter locating the X-ray generator and the X-ray detector such that the X-ray generator and the X-ray detector face each other while having the subject therebetween;

an offset mechanism relatively moving an irradiation direction of the X-ray cone beam irradiated from the X-ray generator, with respect to a center of the imaging region such that the irradiation direction is offset from the center of the imaging region in a reference plane vertical to an imaging central axis of the imaging region;

an axial direction changing mechanism changing as the imaging region from a first imaging region to which the X-ray CT imaging is executed first by the X-ray generator and the X-ray detector to a second imaging region to which the X-ray CT imaging is executed after the first imaging region in an axial direction of the imaging central axis, said imaging region comprising the first imaging region and the second imaging region, and changing the position of the supporter in a direction away from the subject after the X-ray CT imaging of the first imaging region is performed;

an imaging controller controlling the X-ray CT imaging to revolve the supporter with respect to the subject to generate the X-ray imaging information; and an image information generator generating stitch image information acquired as a result of joining first X-ray imaging information on the first imaging region and second X-ray imaging information on the second imaging region in the axial direction, the first X-ray imaging information and the second X-ray imaging information partially overlapping each other in the axial direction, the X-ray CT scanner being configured to be capable of executing:

control on offset CT imaging of controlling the offset mechanism such that the X-ray cone beam is always directed toward a part of the imaging region throughout the imaging, and control on the axial direction changing mechanism to generate the first X-ray imaging information and the second X-ray imaging information partially overlapping each other in the axial direction, and at least one of the first X-ray imaging information and the second X-ray imaging information being offset CT imaging information acquired by the offset CT imaging, wherein the supporter is returned to a start position by rotating in the opposite direction that it rotated in during the X-ray CT imaging of the first imaging region, and wherein the supporter rotates in the opposite direction during the X-ray CT imaging of the second imaging region as it rotated in during the X-ray CT imaging of the first imaging region.

* * * * *